(12) United States Patent
Nomura et al.

(10) Patent No.: US 8,247,575 B2
(45) Date of Patent: Aug. 21, 2012

(54) CARBAZOLE DERIVATIVE WITH HETEROAROMATIC RING, AND LIGHT-EMITTING ELEMENT, LIGHT-EMITTING DEVICE, AND ELECTRONIC DEVICE USING CARBAZOLE DERIVATIVE WITH HETEROAROMATIC RING

(75) Inventors: Hiroko Nomura, Fukuoka (JP); Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 149 days.

(21) Appl. No.: 12/725,696

(22) Filed: Mar. 17, 2010

(65) Prior Publication Data
US 2010/0237339 A1    Sep. 23, 2010

(30) Foreign Application Priority Data

Mar. 20, 2009 (JP) ................................ 2009-069177

(51) Int. Cl.
*C07D 271/10* (2006.01)
*B32B 9/00* (2006.01)
*H01J 1/62* (2006.01)

(52) U.S. Cl. ........ 548/143; 548/125; 313/504; 313/506; 428/690; 428/917

(58) Field of Classification Search .................. 548/125, 548/143; 313/504, 506; 315/169.3; 428/690, 428/917
See application file for complete search history.

(56) References Cited

U.S. PATENT DOCUMENTS

| 6,406,804 | B1 | 6/2002 | Higashi et al. | |
| 7,901,791 | B2 * | 3/2011 | Nakashima et al. | 428/690 |
| 2007/0149784 | A1 | 6/2007 | Murata et al. | |
| 2007/0222376 | A1 | 9/2007 | Ohsawa et al. | |
| 2009/0072718 | A1 | 3/2009 | Nomura et al. | |

FOREIGN PATENT DOCUMENTS

| JP | 8-245954 | 9/1996 |
| JP | 8-311051 | 11/1996 |
| JP | 11-204262 | 7/1999 |
| JP | 2002-352957 | 12/2002 |
| JP | 2003-7467 | 1/2003 |
| JP | 2003-86381 | 3/2003 |
| JP | 2004-71500 | 3/2004 |
| WO | WO 2006/072470 A1 | 7/2006 |

OTHER PUBLICATIONS

Thomas, K.R.J. et al., "Green and Yellow Electroluminescent Dipolar Carbazole Derivatives: Features and Benefits of Electron-Withdrawing Segments," Chemistry of Materials, vol. 14, No. 9, 2002, pp. 3852-3859.
Guan, M. et al, "High-Performance Blue Electroluminescent Devices Based on 2-(4-Biphenylyl)-5-(4-Carbazole-9-yl)Phenyl-1,3,4-Oxadiazole," Chemical Communications, the Royal Society of Chemistry, 2003, pp. 2708-2709.
Thomas, K.R.J. et al, "New Carbazole-Oxadiazole Dyads for Electroluminescent Devices: Influence of Acceptor Substituents on Luminescent and Thermal Properties," Chemistry of Materials, vol. 16, No. 25, 2004, pp. 5437-5444.
Leung, M.-K. et al, "The Unusual Electrochemical and Photophysical Behavior of 2,2'-Bis(1,3,4-Oxadiazol-2-yl)Biphenyls, Effective Electron Transport Hosts for Phosphorescent Organic Light Emitting Diodes," Organic Letters, vol. 9, No. 2, 2007, pp. 235-238.
Baldo, M.A. et al, "Very High-Efficiency Green Organic Light-Emitting Devices Based on Electrophosphorescence," Applied Physics Letters, vol. 75, No. 1, Jul. 5, 1999, pp. 4-6.

* cited by examiner

*Primary Examiner* — Golam M M Shameem
(74) *Attorney, Agent, or Firm* — Husch Blackwell LLP

(57) ABSTRACT

Disclosed is a carbazole derivative and a light-emitting element, a light-emitting device, and an electronic device using thereof. The carbazole derivative possesses an oxadiazole moiety or a quinoxaline moiety as a heteroaromatic ring having an electron-transporting property and a carbazole moiety having a hole-transporting property. The ability of the carbazole derivative to transport both electrons and holes and its large excitation energy larger than a triplet excitation energy of a phosphorescent compound allow the formation of a phosphorescent light-emitting element having well-controlled carrier balance, which contributes to the formation of light-emitting devices and electronic devices that are capable of being driven at a low voltage, have a long lifetime, and consume low power. The detailed structure of the carbazole derivative is defined in the specification.

19 Claims, 28 Drawing Sheets

Highest occupied molecular orbital
(HOMO)

Lowest unoccupied molecular orbital
(LUMO)

Highest occupied molecular orbital
(HOMO)

Lowest unoccupied molecular orbital
(LUMO)

CARBAZOLE DERIVATIVE WITH HETEROAROMATIC RING, AND LIGHT-EMITTING ELEMENT, LIGHT-EMITTING DEVICE, AND ELECTRONIC DEVICE USING CARBAZOLE DERIVATIVE WITH HETEROAROMATIC RING

BACKGROUND OF THE INVENTION

1. Field of the Invention

The present invention relates to a carbazole derivative having a heteroaromatic ring and to a light-emitting element, a light-emitting device, and an electronic device using the same.

2. Description of the Related Art

In recent years, intensive research and development have been made on a light-emitting element utilizing electroluminescence. A basic structure of the light-emitting element is a structure in which a layer containing a light-emitting substance is interposed between a pair of electrodes. Application of a voltage to the light-emitting element provides light emission from the light-emitting substance.

Since the light-emitting element is a self-emitting type element requiring no backlight and possesses advantages such as higher pixel visibility than a liquid crystal display, the light-emitting element has been considered to be suitable for not only the application to a lighting device but also to a flat panel display. In addition, it is also a great advantage that the light-emitting element can be manufactured as a thin and lightweight device. Further, extremely high response speed is also a feature of the light-emitting element.

Since the light-emitting element can be formed in a film shape, light emission from a flat surface with a large area can be readily obtained. Such a feature is difficult to be obtained by point light sources typified by an incandescent lamp and an LED or linear light sources typified by a fluorescent lamp. Accordingly, the light-emitting element is significantly effective for use as a surface light source applicable to lighting device and the like.

The light-emitting element utilizing electroluminescence can be roughly classified according to whether the light-emitting substance is an organic compound or an inorganic compound. When an organic compound is used as the light-emitting substance, by application of a voltage to the light-emitting element, electrons and holes are injected from a pair of electrodes into a layer including the light-emitting organic compound, whereby a current flows. The carriers (electrons and holes) are recombined to allow the light-emitting organic compound to be excited, and light is emitted when the excited state relaxes to the ground state of the light-emitting organic compound.

Resulting from the above-mentioned mechanism, such a light-emitting element is called a current-excitation light-emitting element. Note that an excited state of an organic compound can be a singlet excited state and a triplet excited state. Luminescence from the singlet excited state (S*) is referred to as fluorescence, and luminescence from the triplet excited state (T*) is referred to as phosphorescence. It is considered that the generation ratio of these two excited states in a light-emitting element is statistically S*:T*=1:3, that is, the generation ratio of the singlet excited state is 25%, while that of the triplet excited state is 75%.

A compound capable of emitting light from a singlet excited state (hereinafter, referred to as a fluorescent compound) generally does not emit light from its triplet excited state (phosphorescence) at room temperature and exhibits only luminescence (fluorescence) from the singlet excited state. Therefore, it is believed that the theoretical maximum of the internal quantum efficiency (ratio of generated photon to injected carriers) of a light-emitting element utilizing a fluorescent compound is 25% since the generation ratio of the singlet excited state in a light-emitting element is 25%.

On the other hand, the generation ratio of the triplet excited state in a light-emitting element reaches 75%, and some organic molecules existing in the singlet excited state are able to convert to the triplet excited state. Therefore, the use of a compound capable of emitting light from the triplet excited state (hereinafter, referred to as a phosphorescent compound) theoretically allows the internal quantum efficiency of a light-emitting element to be improved up to 75% to 100%, and luminous efficiency which is 3 times to 4 times as high as that using a fluorescent compound can be obtained. For these reasons, in order to achieve a light-emitting element with high efficiency, a light-emitting element using a phosphorescent compound has been intensively developed recently (Patent Document 1 and Non-Patent Document 1).

When a light-emitting layer of a light-emitting element is formed using the aforementioned phosphorescent compound, the phosphorescent compound is dispersed in a matrix formed of another material in most cases in order to suppress the concentration quenching of the phosphorescent compound and the triplet-triplet annihilation. In these cases, the material used to form the matrix is called a host material, and the material dispersed in the matrix like the phosphorescent material is called a guest material.

In the case where the phosphorescent compound is used as a guest material, the host material is required to have larger triplet excitation energy (a difference in energy between the ground state and the triplet excited state) than the phosphorescent compound. It is well know that CBP used as the host material in Non-Patent Document 1 has larger triplet excitation energy than the phosphorescent compound that emits light of green to red colors. Therefore, it is widely used as the host material for the phosphorescent compound.

However, although CBP has high triplet excitation energy, its insufficient ability to accept holes and electrons causes a problem in that driving voltage of the light-emitting element is increased. Therefore, a substance that has high triplet excitation energy and also can readily accept and transport both holes and electrons (i.e. a bipolar substance) is required as the host material for the phosphorescent compound.

In addition, since singlet excitation energy (an energy difference between the ground state and the singlet excited state) is larger than triplet excitation energy, a substance having high triplet excitation energy also possesses high singlet excitation energy. Therefore, the aforementioned substance, which has a bipolar property in addition to high triplet excitation energy, is effective in a light-emitting element using a fluorescent compound as the light-emitting substance.

REFERENCES

Patent Document

[Patent Document 1]
Japanese Patent Laid-Open No. 2002-352957

Non-Patent Document

[Non-Patent Document 1]
M. A. Baldo, et al., *Applied Physics Letters*, vol. 75, No. 1, pp. 4-6 (1999).

SUMMARY OF THE INVENTION

An object of an embodiment of the present invention is to provide a substance having large excitation energy, especially, a compound having an energy gap larger than triplet excitation energy of a phosphorescent compound that emits visible light. Further, another object is to provide a bipolar compound. Still another object is to improve performance of a light-emitting element. Yet another object is to provide a light-emitting device and an electronic device which consume low power and can be driven at a low voltage.

Specifically, provided is a carbazole derivative having a heteroaromatic ring where the carbazole derivative possesses an oxadiazole moiety or a quinoxaline moiety as the heteroaromatic ring having an electron-transporting property and a carbazole moiety having a hole-transporting property in the same molecule. Furthermore, a light-emitting element is provided in which the aforementioned carbazole derivative having the heteroaromatic ring is used in the light-emitting layer or carrier-transporting layer thereof. Moreover, a light-emitting device and an electronic device to which the aforementioned light-emitting element is applied are provided.

One embodiment of the present invention is a carbazole derivative having a heteroaromatic ring represented by the following general formula (G1).

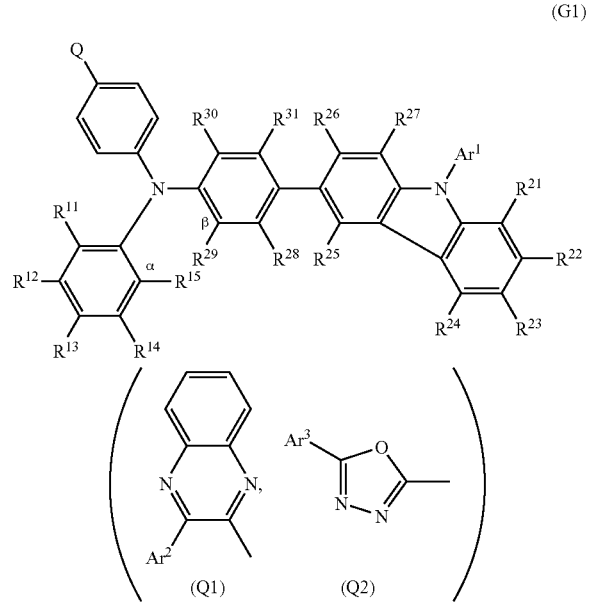

(G1)

(In the formula, Q is a substituent represented by the general formula Q1 or Q2; $Ar^1$ to $Ar^3$ each are an aryl group having 6 to 10 carbon atoms in a ring; and the aryl group optionally has a substituent. $R^{28}$ to $R^{31}$ each are a hydrogen atom or an alkyl group having 1 to 4 carbon atoms. $R^{11}$ to $R^{15}$ and $R^{21}$ to $R^{27}$ each are a hydrogen atom, an alkyl group having 1 to 4 carbon atoms, or an aryl group having 6 to 10 carbon atoms in a ring, and the aryl group optionally has a substituent. Note that the carbon at the α position and the carbon at the β position may be directly bonded to each other to form a carbazole ring.)

Another embodiment of the invention disclosed is a carbazole derivative having a heteroaromatic ring represented by the following general formula (G2).

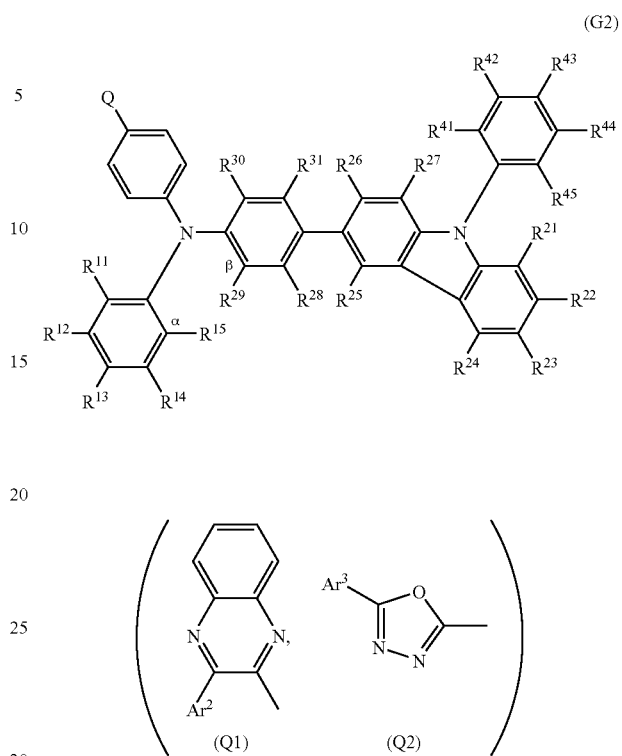

(G2)

(In the formula, Q is a substituent represented by the general formula Q1 or Q2; $Ar^2$ and $Ar^3$ each are an aryl group having 6 to 10 carbon atoms in a ring; and the aryl group optionally has a substituent. $R^{28}$ to $R^{31}$ each are a hydrogen atom or an alkyl group having 1 to 4 carbon atoms. $R^{11}$ to $R^{15}$, $R^{21}$ to $R^{27}$, and $R^{41}$ to $R^{45}$ each are a hydrogen atom, an alkyl group having 1 to 4 carbon atoms, or an aryl group having 6 to 10 carbon atoms in a ring, and the aryl group optionally has a substituent. Note that the carbon at the α position and the carbon at the β position may be directly bonded to each other to form a carbazole ring.)

Still another embodiment of the invention disclosed is a carbazole derivative having a heteroaromatic ring represented by the following general formula (G3).

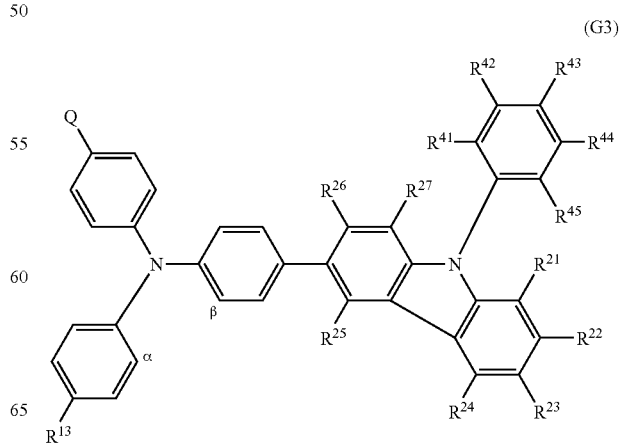

(G3)

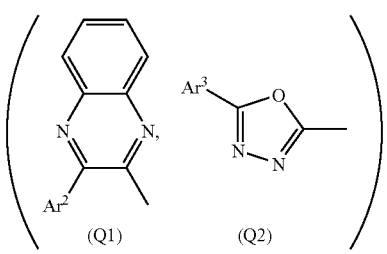

(In the formula, Q is a substituent represented by the general formula Q1 or Q2; $Ar^2$ and $Ar^3$ each are an aryl group having 6 to 10 carbon atoms in a ring; and the aryl group optionally has a substituent. $R^{13}$, $R^{21}$ to $R^{27}$, and $R^{41}$ to $R^{45}$ each are a hydrogen atom, an alkyl group having 1 to 4 carbon atoms, or an aryl group having 6 to 10 carbon atoms in a ring, and the aryl group optionally has a substituent. Note that the carbon at the α position and the carbon at the β position may be directly bonded to each other to form a carbazole ring.)

Yet another embodiment of the invention disclosed is a carbazole derivative having a heteroaromatic ring represented by the following general formula (G4).

(G4)

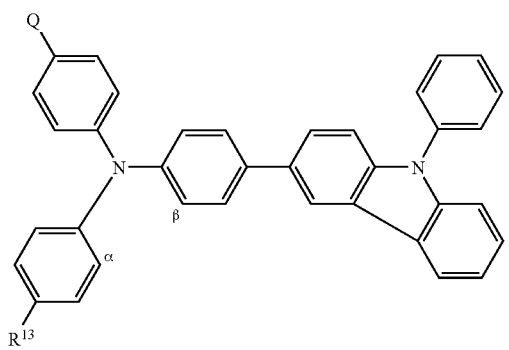

(In the formula, Q is a substituent represented by the general formula Q1 or Q2; $Ar^2$ and $Ar^3$ each are an aryl group having 6 to 10 carbon atoms in a ring; and the aryl group optionally has a substituent. $R^{13}$ is a hydrogen atom, an alkyl group having 1 to 4 carbon atoms, or an aryl group having 6 to 10 carbon atoms in a ring, and the aryl group optionally has a substituent. Note that the carbon at the α position and the carbon at the β position may be directly bonded to each other to form a carbazole ring.)

Furthermore, an embodiment of the invention disclosed is a carbazole derivative having a heteroaromatic ring represented by the following general formula (G5).

(G5)

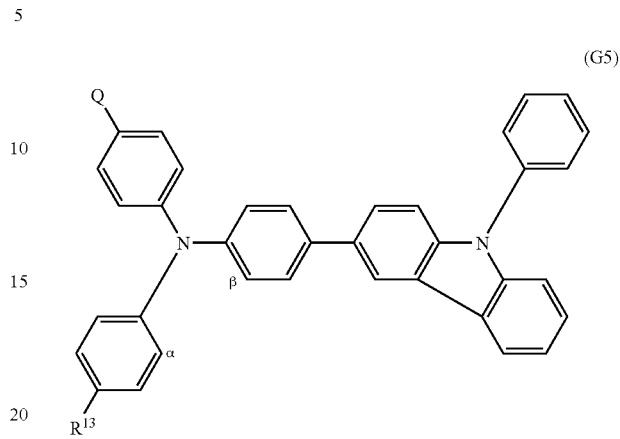

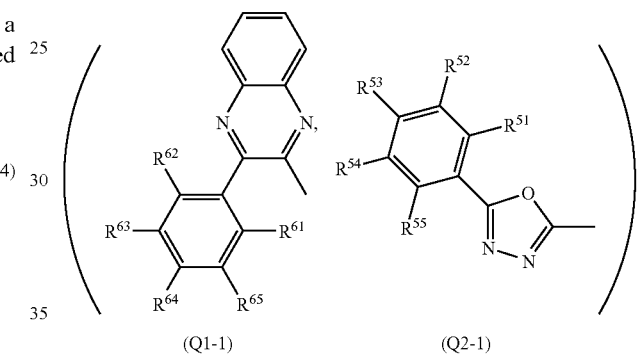

(In the formula, Q is a substituent represented by the general formula Q1-1 or Q2-1; $R^{13}$, $R^{51}$ to $R^{55}$, and $R^{61}$ to $R^{65}$ each are a hydrogen atom, an alkyl group having 1 to 4 carbon atoms, or an aryl group having 6 to 10 carbon atoms in a ring, and the aryl group optionally has a substituent. Note that the carbon at the α position and the carbon at the β position may be directly bonded to each other to form a carbazole ring.)

Another embodiment of the invention disclosed is a carbazole derivative having a heteroaromatic ring represented by the following general formula (G6).

(G6)

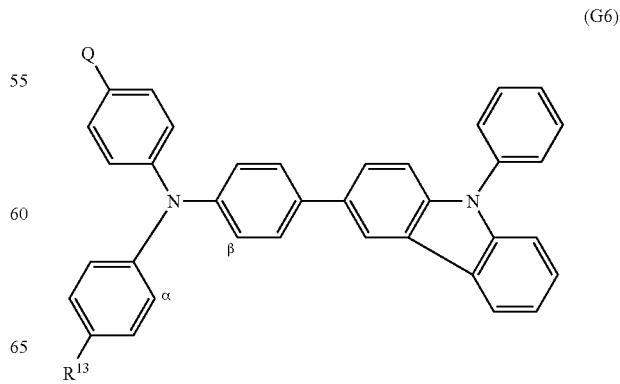

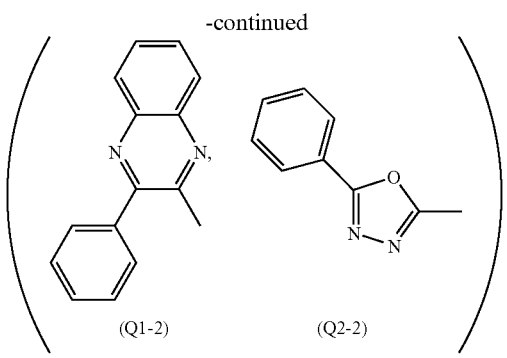

(Q1-2)  (Q2-2)

(In the formula, Q is a substituent represented by the structural formula Q1-2 or Q2-2; $R^{13}$ is a hydrogen atom, an alkyl group having 1 to 4 carbon atoms, or an aryl group having 6 to 10 carbon atoms in a ring, and the aryl group optionally has a substituent. Note that the carbon at the α position and the carbon at the β position may be directly bonded to each other to form a carbazole ring.)

Another embodiment of the invention disclosed is a light-emitting element which comprises at least one of the carbazole derivatives having the heteroaromatic ring represented by the aforementioned general formulae (G1), (G2), (G3), (G4), (G5), and (G6) between a pair of electrodes.

Still another embodiment of the invention disclosed is a light-emitting element which comprises a light-emitting layer between a pair of electrodes, where the light-emitting layer comprises: at least one of the carbazole derivatives having the heteroaromatic ring represented by the aforementioned general formulae (G1), (G2), (G3), (G4), (G5), and (G6); and a light-emitting substance.

Yet another embodiment of the invention disclosed is a light-emitting element which comprises a light-emitting layer between a pair of electrodes, where the light-emitting layer comprises: at least one of the carbazole derivatives having the heteroaromatic ring represented by the aforementioned general formulae (G1), (G2), (G3), (G4), (G5), and (G6); and a phosphorescent substance.

Another embodiment of the invention disclosed is a light-emitting device and an electronic device which comprise a light-emitting element having a light-emitting layer between a pair of electrodes, where the light-emitting layer comprises: at least one of the carbazole derivatives having the heteroaromatic ring represented by the aforementioned general formulae (G1), (G2), (G3), (G4), (G5), and (G6); and a light-emitting substance.

Note that the category of a light-emitting device in this specification includes an image display device or a light-emitting device using a light-emitting element. Further, the category of the light-emitting device of the present invention includes a module including a substrate provided with a light-emitting element, to which a connector such as a tape automated bonding (TAB) tape such as an anisotropic conductive film or a tape carrier package (TCP) is attached; a module in which an end of a connector is provided with a printed wiring board; and a module in which an integrated circuit (IC) is directly mounted on a substrate provided with a light-emitting element by a chip on glass (COG) method.

The light-emitting element of an embodiment of the present invention is characterized in having a layer between a pair of electrodes, where the layer comprises the carbazole derivative having the heteroaromatic ring of an embodiment of the present invention.

The light-emitting device of an embodiment of the present invention is characterized in having the aforementioned light-emitting element and a control means which controls the light emission from the light-emitting element. The electronic device of an embodiment of the present invention is characterized in having a display portion which includes the light-emitting element and the control means for the light emission from the light-emitting element.

Since the light emission with high efficiency can be realized by the light-emitting element of an embodiment of the present invention, the light-emitting device utilizing the light-emitting element can achieve low power-consumption. Thus, an embodiment of the present invention also includes the light-emitting device and an electronic device each of which uses the light-emitting element.

Note that the substituent, which is bonded to the aryl group having 6 to 10 carbon atoms in a ring, is an alkyl group having 1 to 4 carbon atoms or an aryl group having 6 to 10 carbon atoms in a ring, and the aryl group of the substituent optionally has an alkyl group having 1 to 4 carbon atoms.

The present invention is able to provide a novel carbazole derivative having a heteroaromatic ring which has a larger energy gap than a phosphorescent compound emitting visible light and can be used as an electron-transporting layer and as a host material of a light-emitting layer of a light-emitting element. Furthermore, it is possible to provide a light-emitting element with high luminous efficiency by using the novel carbazole derivative having the heteroaromatic ring. Moreover, a light-emitting device and an electronic device with reduced power consumption can be provided.

DETAILED DESCRIPTION OF THE INVENTION

Figure 1A:
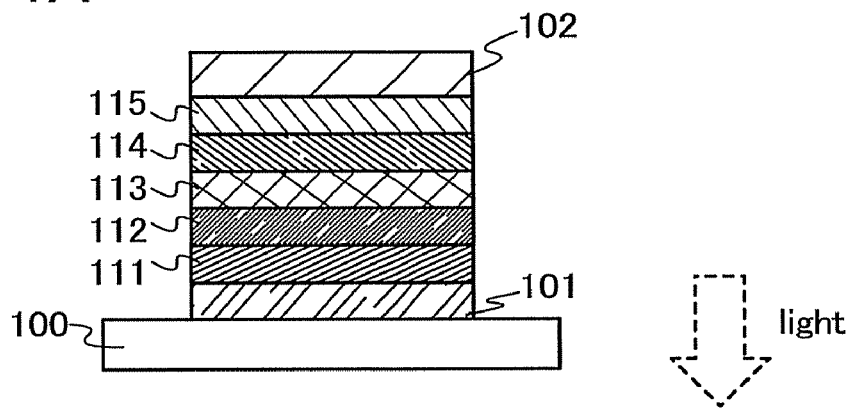
FIGS. 1A to 1C each illustrate a light-emitting element according to an embodiment of the present invention.

Hereinafter, embodiments of the present invention will be described in detail with reference to the accompanying drawings. Note that the present invention is not limited to the description below, and it is easily understood by those skilled in the art that a variety of changes and modifications can be made without departing from the spirit and scope of the present invention. Therefore, the present invention should not be limited to the descriptions of the embodiment modes and the embodiment below.

Embodiment 1

This embodiment explains a carbazole derivative having a heteroaromatic ring of an embodiment of the present invention.

The general formula (G1) of the carbazole derivative having the heteroaromatic ring of the present embodiment is shown below.

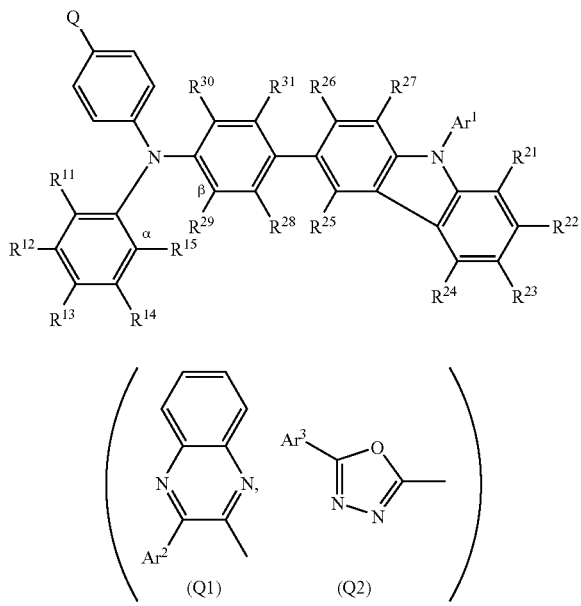

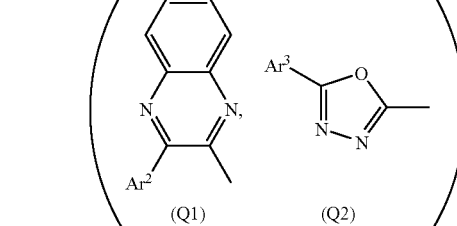

(In the formula, Q is a substituent represented by the general formula Q1 or Q2; $Ar^1$ to $Ar^3$ each are an aryl group having 6 to 10 carbon atoms in a ring; and the aryl group optionally has a substituent. $R^{28}$ to $R^{31}$ each are a hydrogen atom or an alkyl group having 1 to 4 carbon atoms. $R^{11}$ to $R^{15}$ and $R^{21}$ to $R^{27}$ each are a hydrogen atom, an alkyl group having 1 to 4 carbon atoms, or an aryl group having 6 to 10 carbon atoms which form a ring, and the aryl group optionally has a substituent. Note that the carbon at the α position and the carbon at the β position may be directly bonded to each other to form a carbazole ring.) Introduction of the alkyl group improves the solubility of the carbazole derivative having the heteroaromatic ring of an embodiment of the present invention In the general formula (G1), $Ar^1$ to $Ar^3$ each are an aryl group having 6 to 10 carbon atoms in a ring, and the aryl group optionally has a substituent. Specifically, the substituents represented by the structural formulae S-1 to S-17 can be exemplified as $Ar^1$ to $Ar^3$.

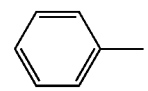

(S-1)

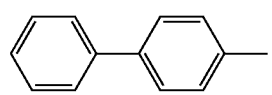

(S-2)

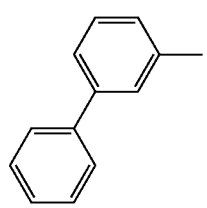

(S-3)

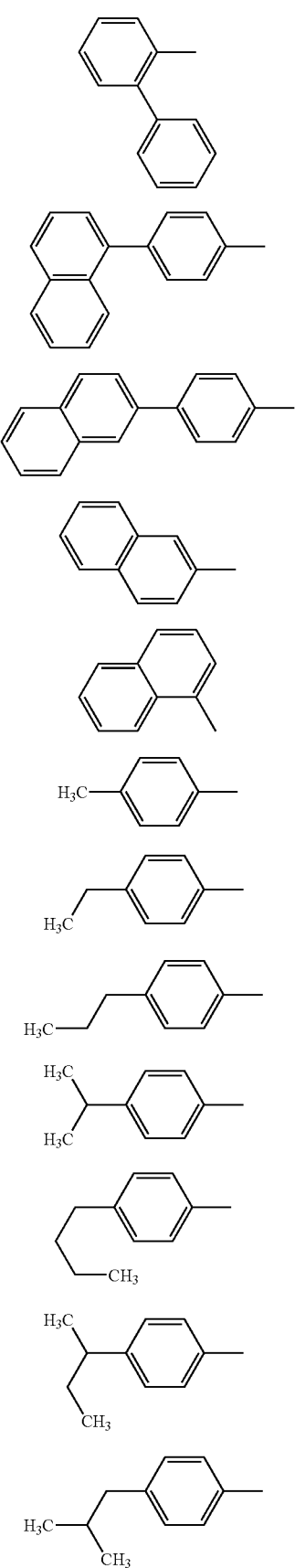

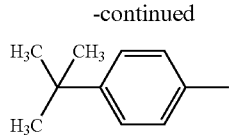

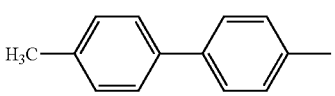

In the general formula (G1), $R^{28}$ to $R^{31}$ each are a hydrogen atom or an alkyl group having 1 to 4 carbon atoms. Specifically, the substituents represented by the structural formulae S-18 to S-26 can be exemplified as $R^{28}$ to $R^{31}$.

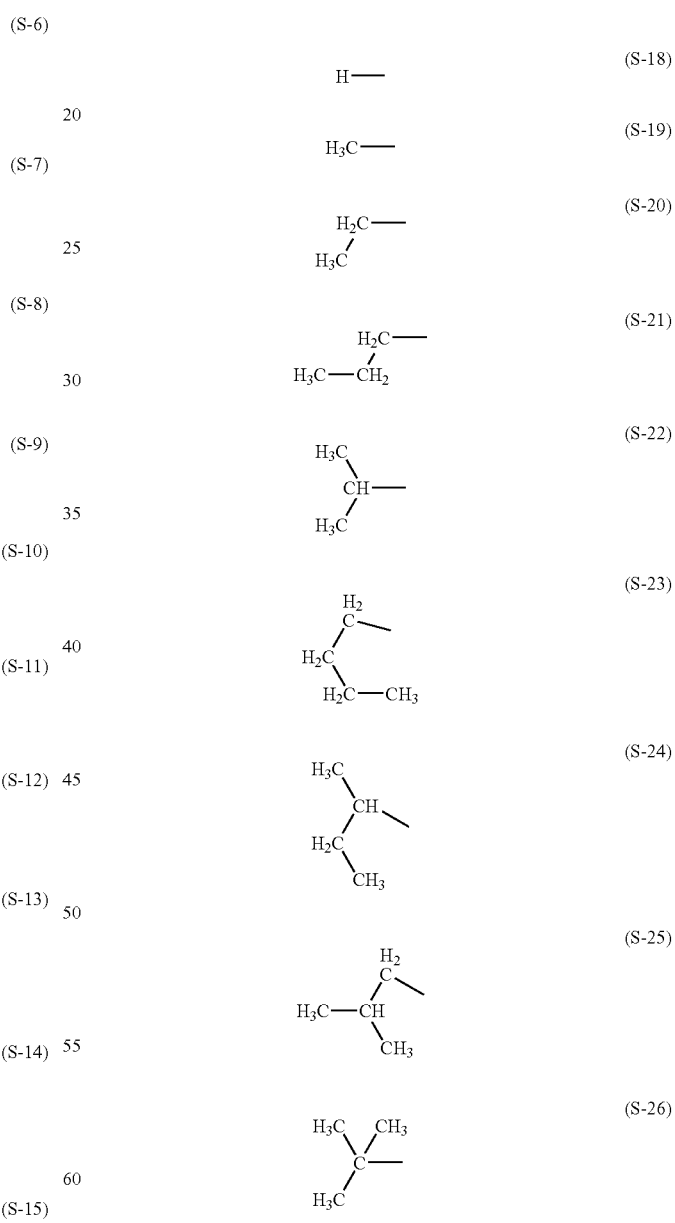

In the general formula (G1), $R^{11}$ to $R^{15}$ and $R^{21}$ to $R^{27}$ each are a hydrogen atom, an alkyl group having 1 to 4 carbon atoms, or an aryl group having 6 to 10 carbon atoms in a ring, and the aryl group optionally has a substituent. The substituents represented by the structural formulae S-1 to S-26 are given as the specific examples of $R^{11}$ to $R^{15}$ and $R^{21}$ to $R^{27}$.

Note that, in the general formula (G1), the carbon at the α position and the carbon at the β position may be directly bonded to each other to form a carbazole ring.

It is preferred that $Ar^1$ in the general formula (G1) is a phenyl group because the synthesis of the carbazole derivative is facilitated and the starting materials for the synthesis are available at small cost. In that case, the carbazole derivative having the heteroaromatic ring of an embodiment of the present invention is represented by the following general formula (G2).

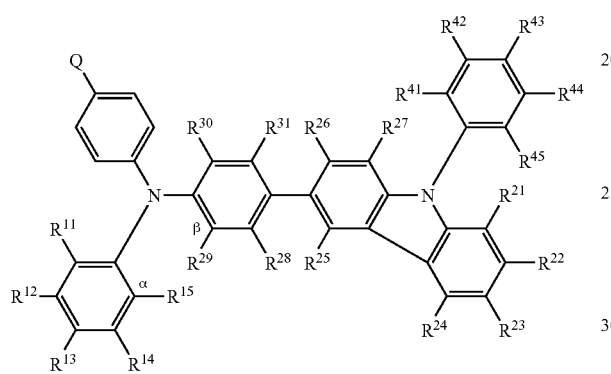

(G2)

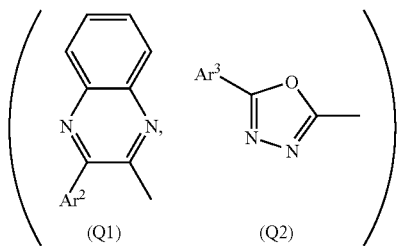

(In the formula, Q is a substituent represented by the general formula Q1 or Q2; $Ar^2$ and $Ar^3$ each are an aryl group having 6 to 10 carbon atoms in a ring; and the aryl group optionally has a substituent. $R^{28}$ to $R^{31}$ each are a hydrogen atom or an alkyl group having 1 to 4 carbon atoms. $R^{11}$ to $R^{15}$, $R^{21}$ to $R^{27}$, and $R^{41}$ to $R^{45}$ each are a hydrogen atom, an alkyl group having 1 to 4 carbon atoms, or an aryl group having 6 to 10 carbon atoms in a ring, and the aryl group optionally has a substituent. Note that the carbon at the α position and the carbon at the β position may be directly bonded to each other to form a carbazole ring.)

It is preferred that $R^{11}$, $R^{12}$, $R^{14}$, $R^{15}$, and $R^{28}$ to $R^{31}$ in the general formula (G2) each are a hydrogen atom since no large steric hindrance is caused and the synthesis of the carbazole derivative is facilitated. In that case, the carbazole derivative having the heteroaromatic ring of an embodiment of the present invention is represented by the following general formula (G3).

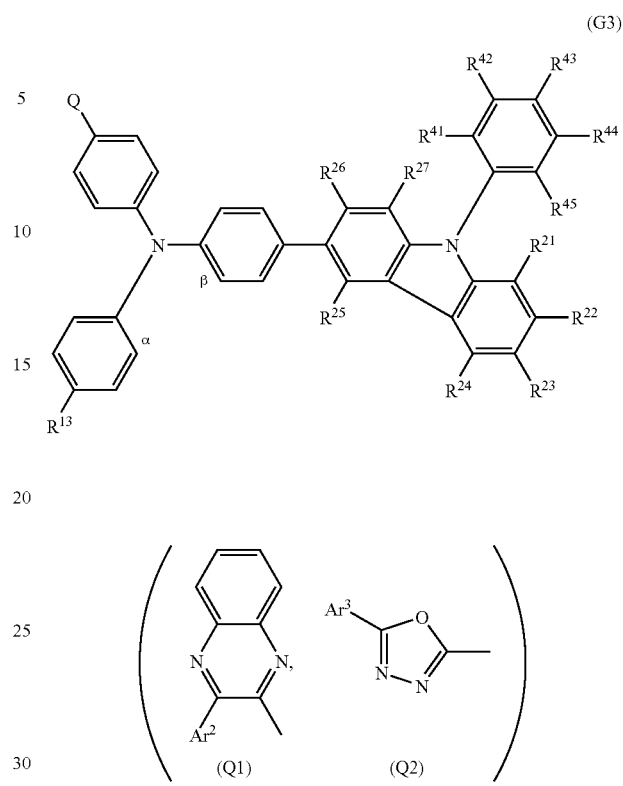

(G3)

(In the formula, Q is a substituent represented by the general formula Q1 or Q2; $Ar^2$ and $Ar^3$ each are an aryl group having 6 to 10 carbon atoms in a ring; and the aryl group optionally has a substituent. $R^{13}$, $R^{21}$ to $R^{27}$, and $R^{41}$ to $R^{45}$ each are a hydrogen atom, an alkyl group having 1 to 4 carbon atoms, or an aryl group having 6 to 10 carbon atoms in a ring, and the aryl group optionally has a substituent. Note that the carbon at the α position and the carbon at the β position may be directly bonded to each other to form a carbazole ring.)

It is preferred that $R^{41}$ to $R^{45}$ and $R^{21}$ to $R^{27}$ in the general formula (G3) each are a hydrogen atom since the triplet excitation energy of the carbazole derivative becomes larger. In that case, the carbazole derivative having the heteroaromatic ring of an embodiment of the present invention is represented by the following general formula (G4).

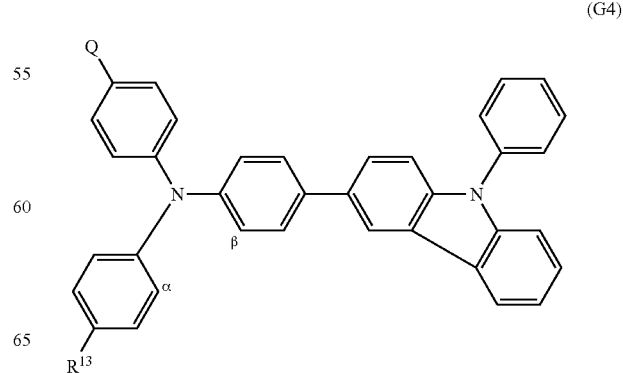

(G4)

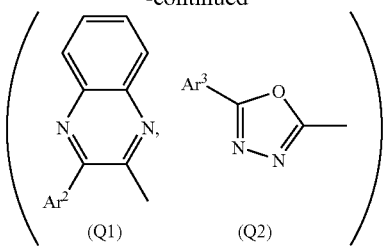

(In the formula, Q is a substituent represented by the general formula Q1 or Q2; $Ar^2$ and $Ar^3$ each are an aryl group having 6 to 10 carbon atoms in a ring; and the aryl group optionally has a substituent. $R^{13}$ is a hydrogen atom, an alkyl group having 1 to 4 carbon atoms, or an aryl group having 6 to 10 carbon atoms in a ring, and the aryl group optionally has a substituent. Note that the carbon at the α position and the carbon at the β position may be directly bonded to each other to form a carbazole ring.)

It is preferred that $Ar^2$ and $Ar^3$ in the general formula (G4) each are a phenyl group since the triplet excitation energy becomes larger. In that case, the carbazole derivative having the heteroaromatic ring of an embodiment of the present invention is represented by the following general formula (G5).

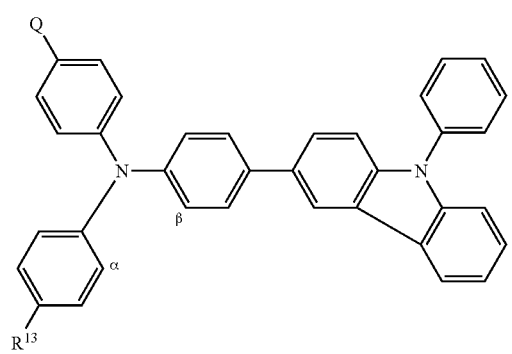

(G5)

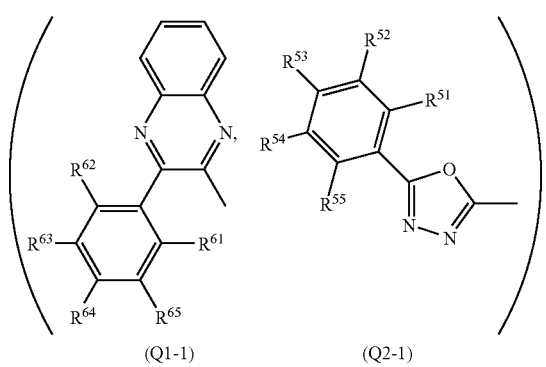

(In the formula, Q is a substituent represented by the general formula Q1-1 or Q2-1; $R^{13}$, $R^{51}$ to $R^{55}$, and $R^{61}$ to $R^{65}$ each are a hydrogen atom, an alkyl group having 1 to 4 carbon atoms, or an aryl group having 6 to 10 carbon atoms in a ring, and the aryl group optionally has a substituent. Note that the carbon at the α position and the carbon at the β position may be directly bonded to each other to form a carbazole ring.)

It is preferred that $R^{51}$ to $R^{55}$ and $R^{61}$ to $R^{65}$ in the general formula (G5) each are a hydrogen atom since the triplet excitation energy becomes larger. In that case, the carbazole derivative having the heteroaromatic ring of an embodiment of the present invention is represented by the following general formula (G6).

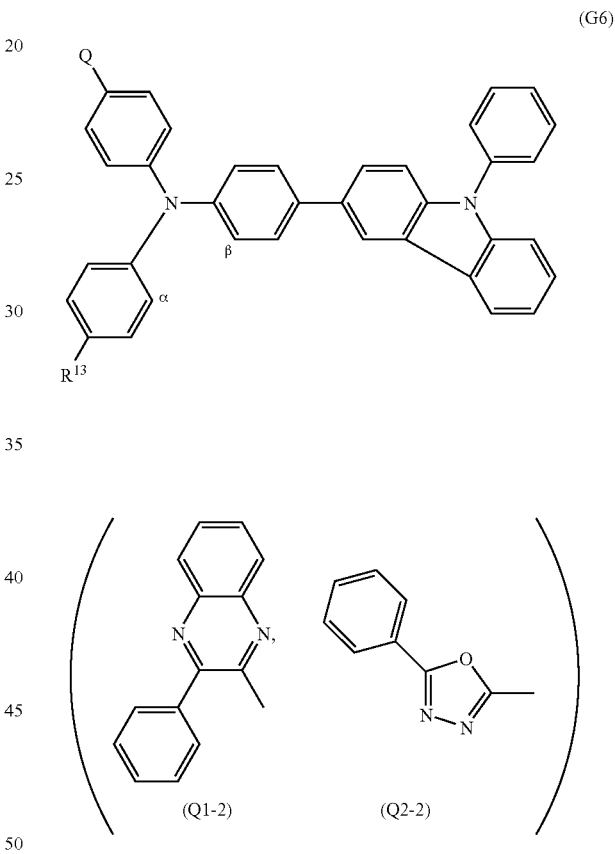

(In the formula, Q is a substituent represented by the structural formula Q1-2 or Q2-2; $R^{13}$ is a hydrogen atom, an alkyl group having 1 to 4 carbon atoms, or an aryl group having 6 to 10 carbon atoms in a ring, and the aryl group optionally has a substituent. Note that the carbon at the α position and the carbon at the β position may be directly bonded to each other to form a carbazole ring.)

As specific examples of the carbazole derivative having the heteroaromatic ring, the compounds represented by the structural formulae (1) to (128) can be given. However, the present invention is not limited to the following compounds.

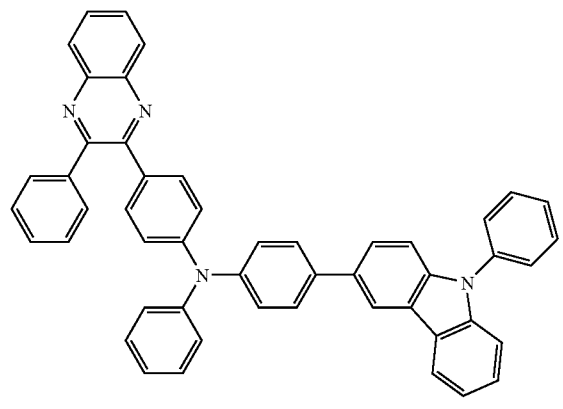
(1)
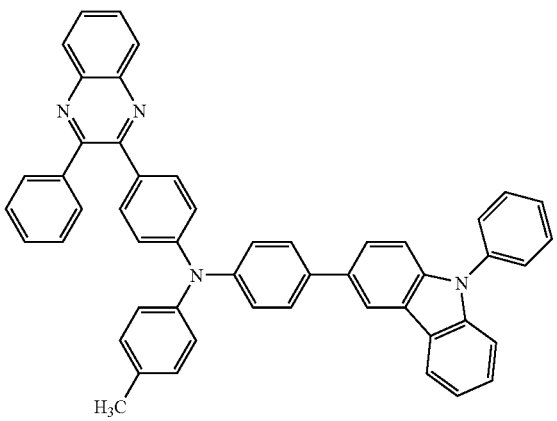
(2)
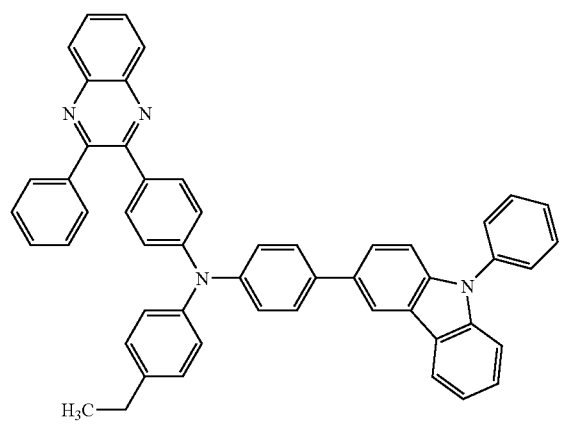
(3)
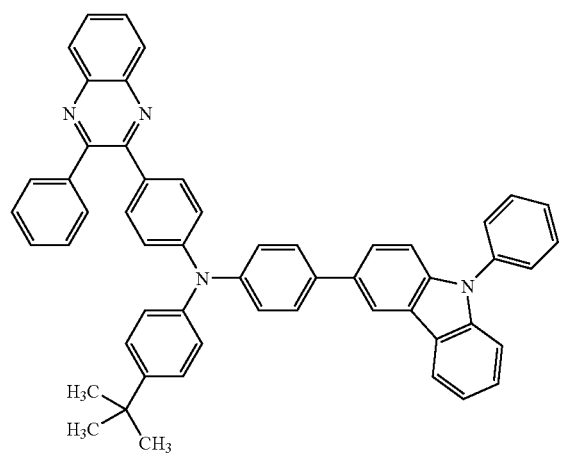
(4)
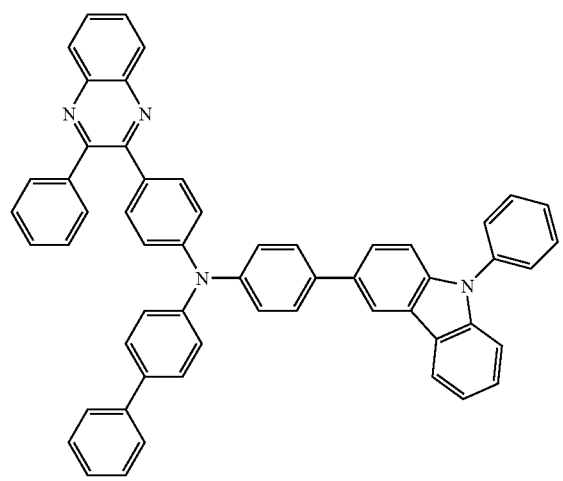
(5)
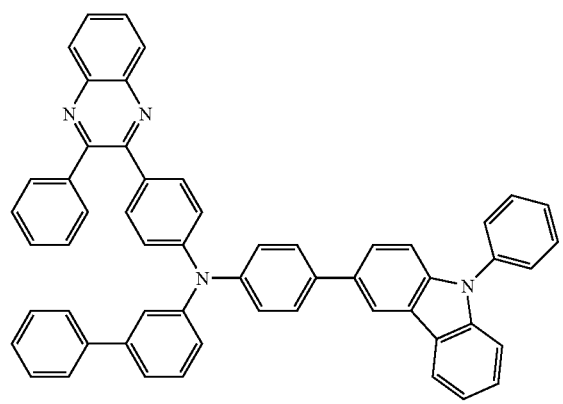
(6)

-continued
(7)
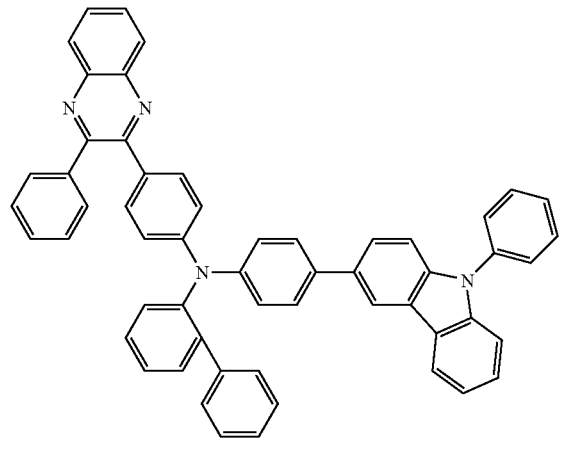
(8)
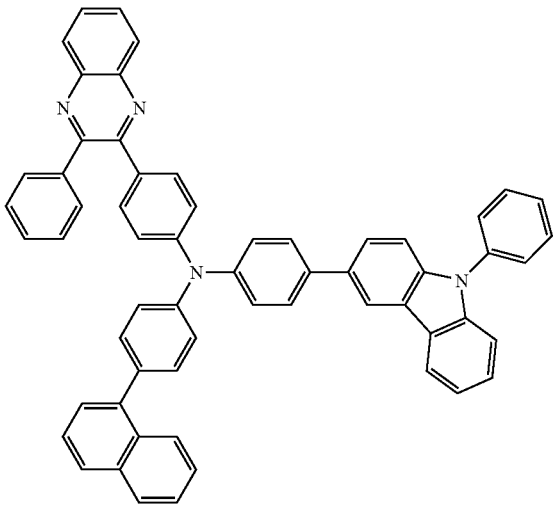
(9)
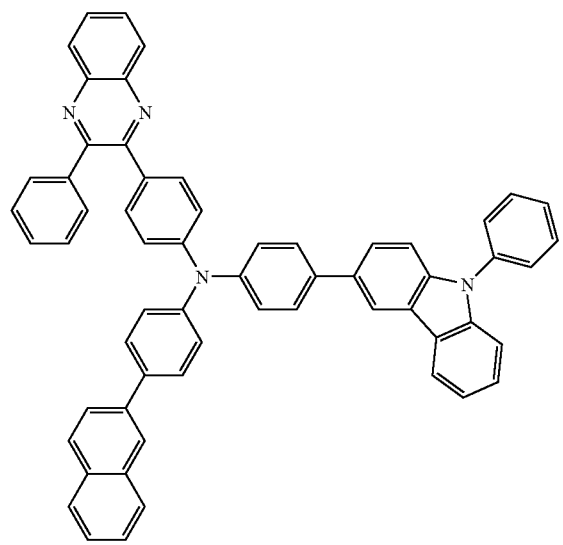
(10)
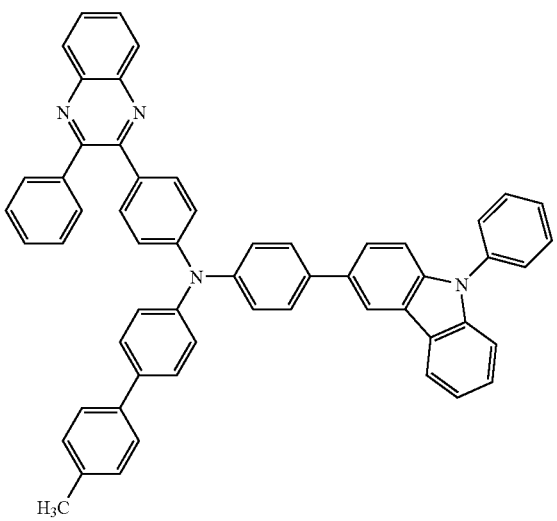
(11)
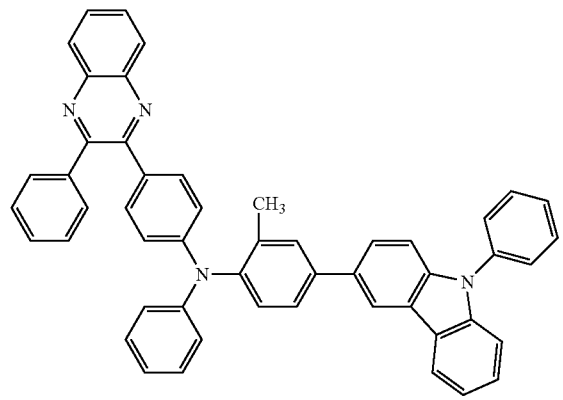
(12)
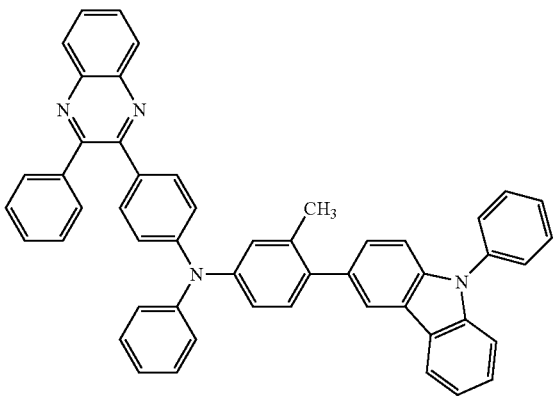

-continued
(13)
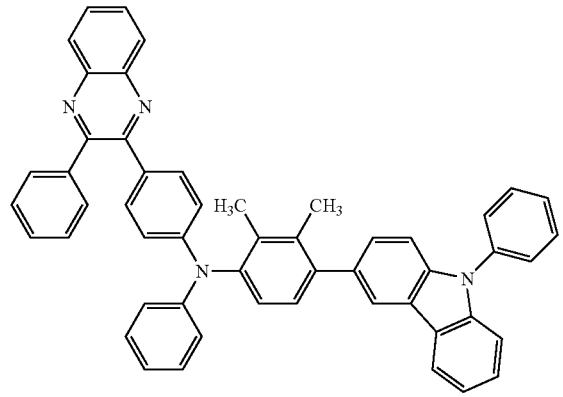
(14)
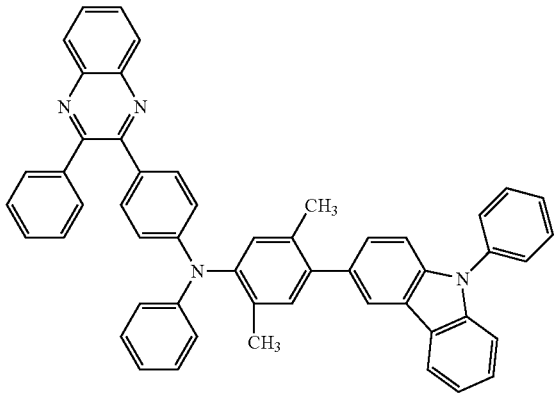
(15)
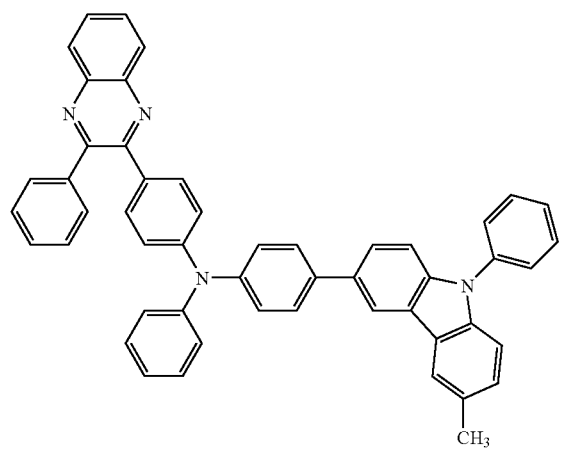
(16)
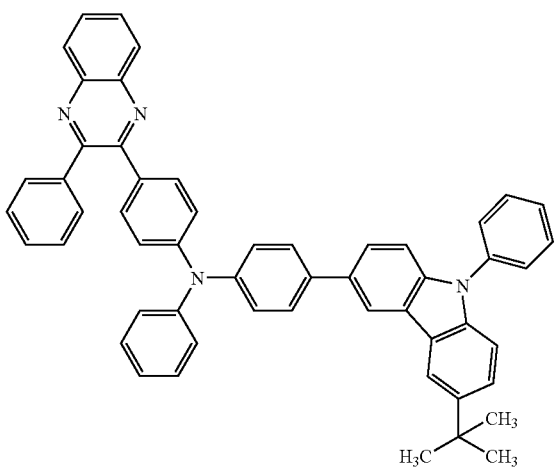
(17)
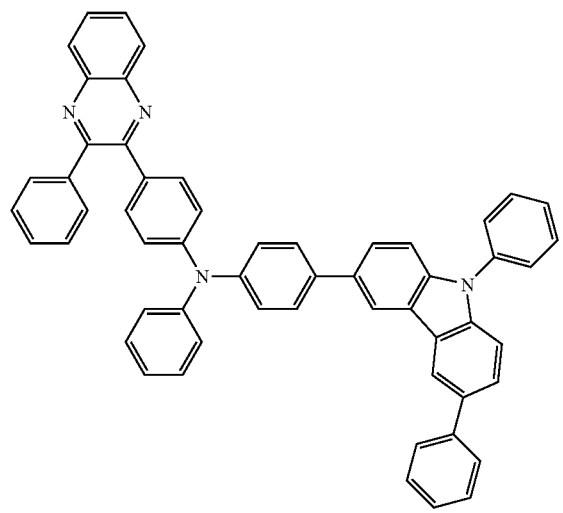
(18)
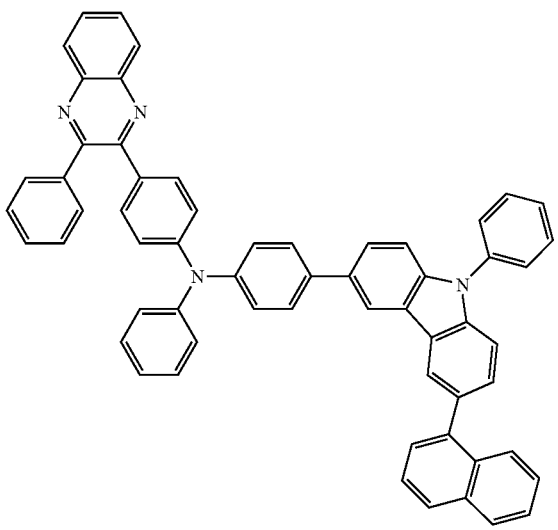

-continued
(19)
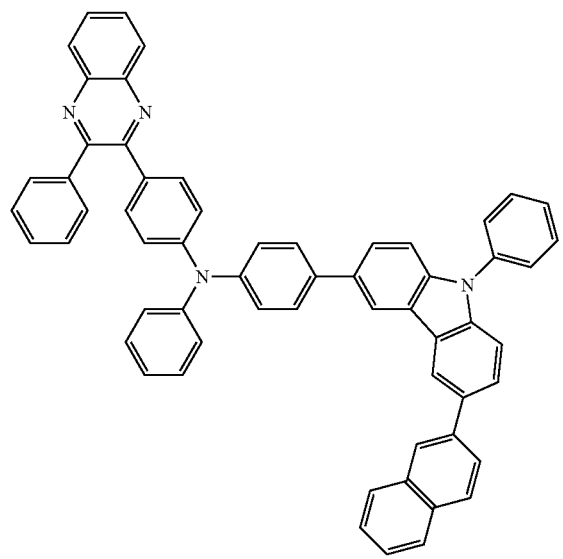
(20)
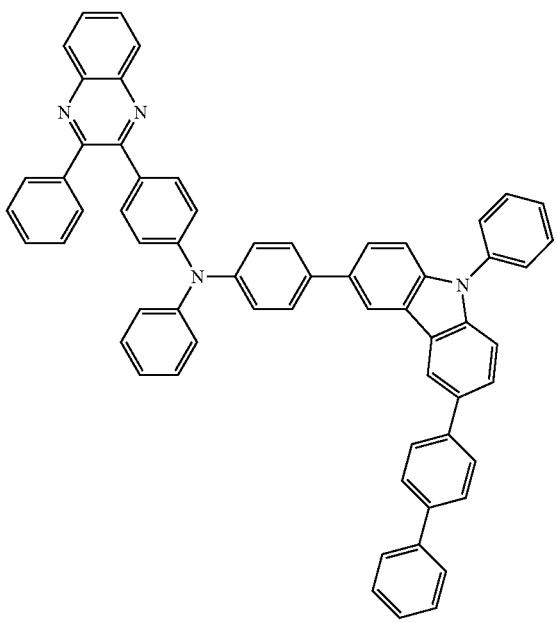
(21)
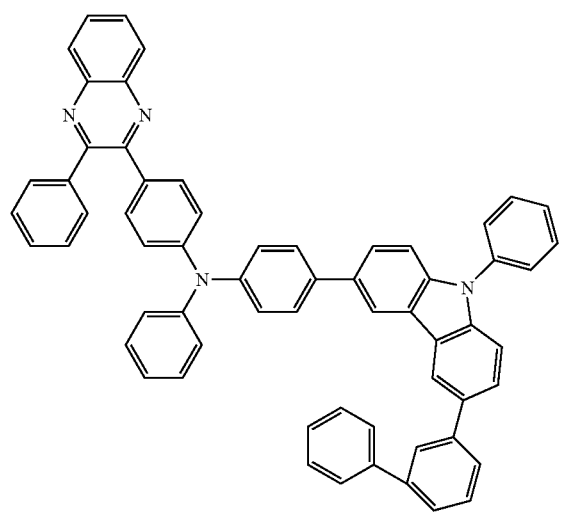
(22)
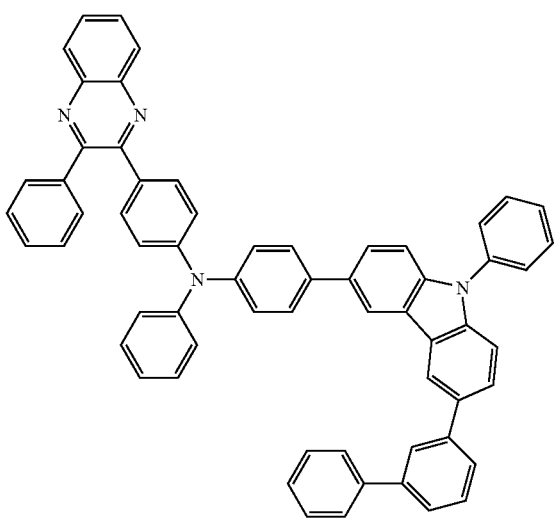

-continued
(23)
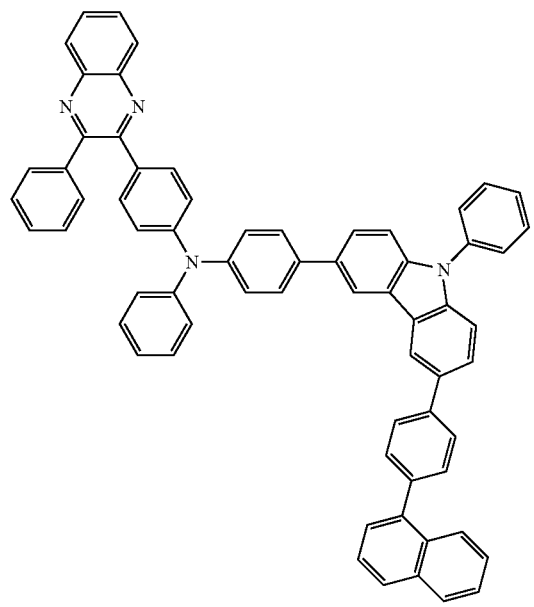
(24)
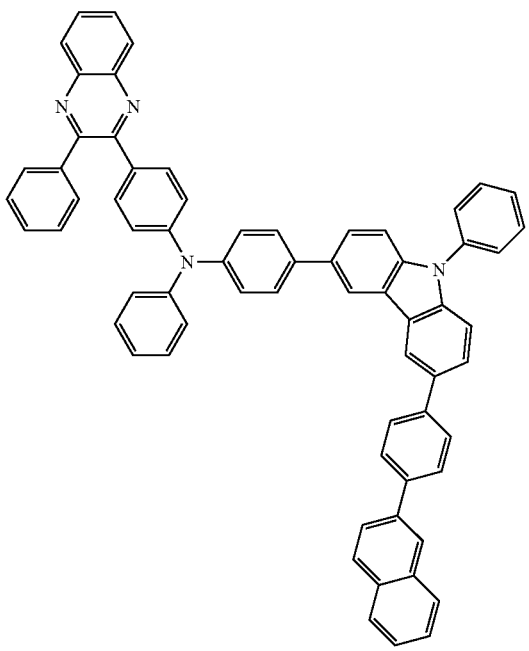
(25)
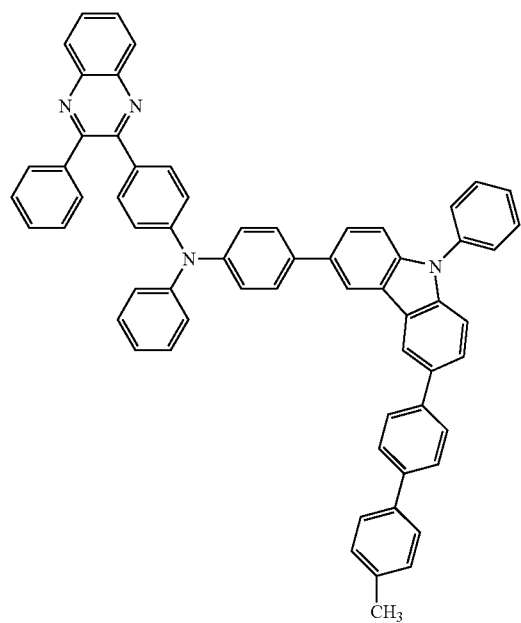
(26)
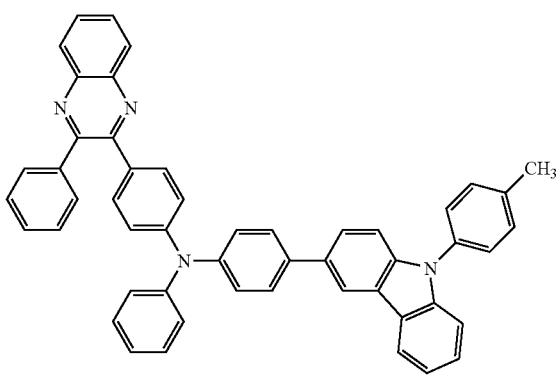
(27)
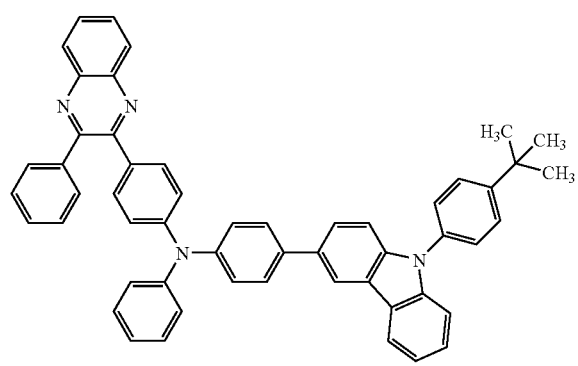
(28)
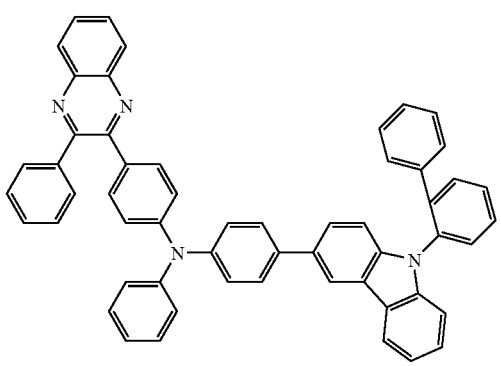

-continued
(29)
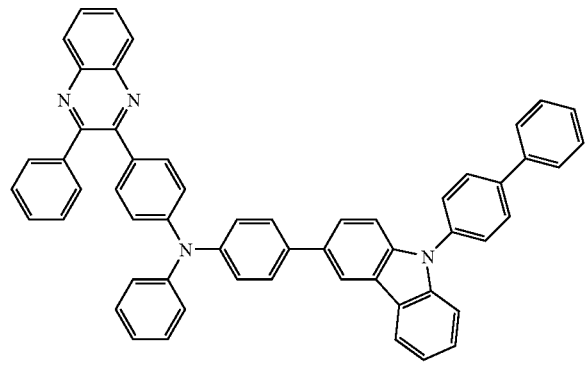
(30)
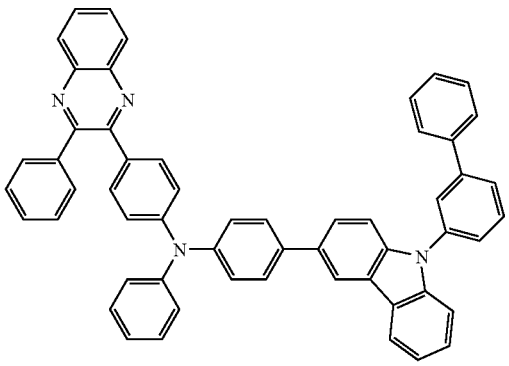
(31)
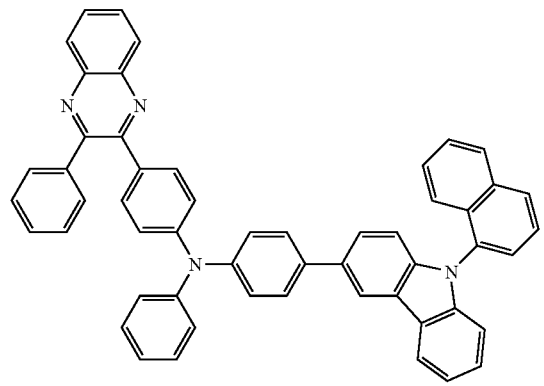
(32)
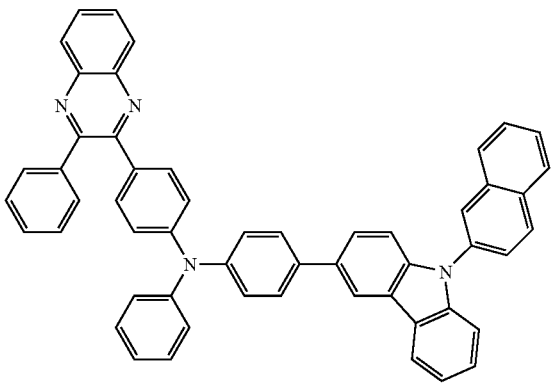
(33)
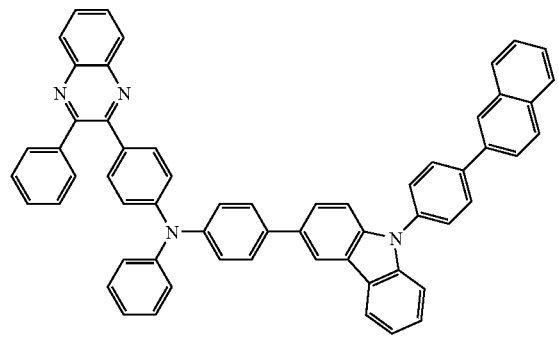
(34)
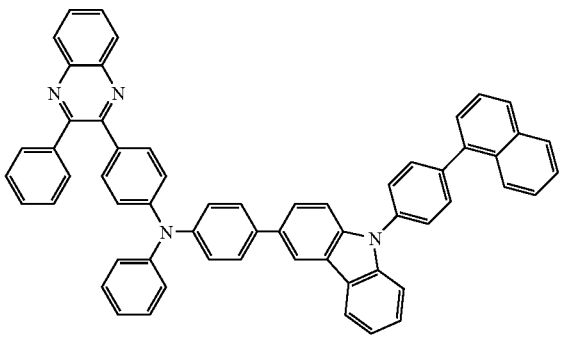
(35)
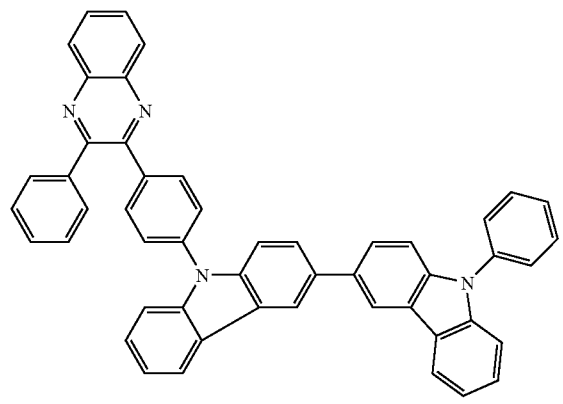
(36)
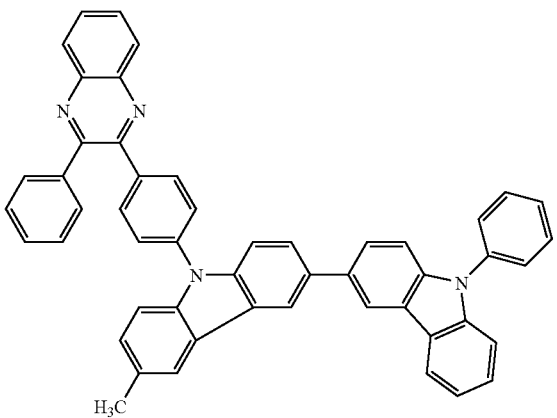

-continued
(37)
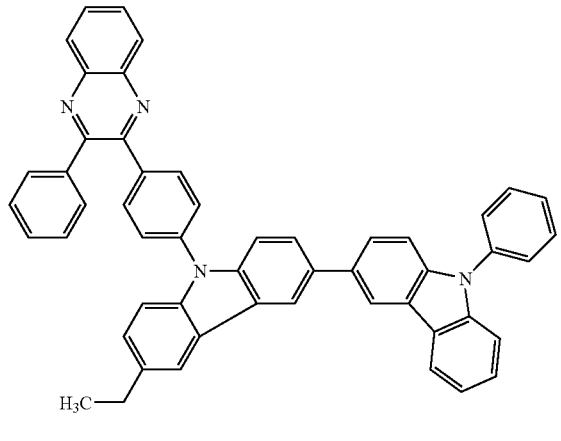
(38)
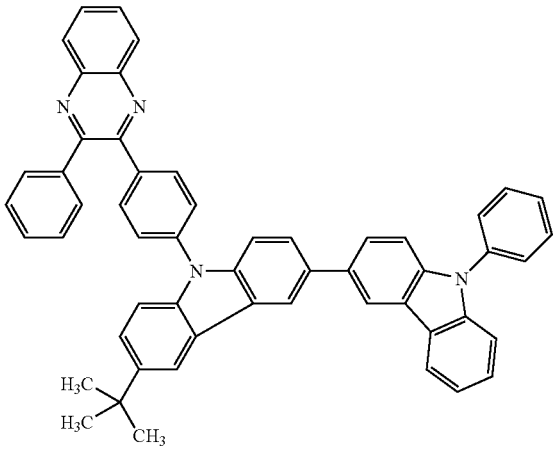
(39)
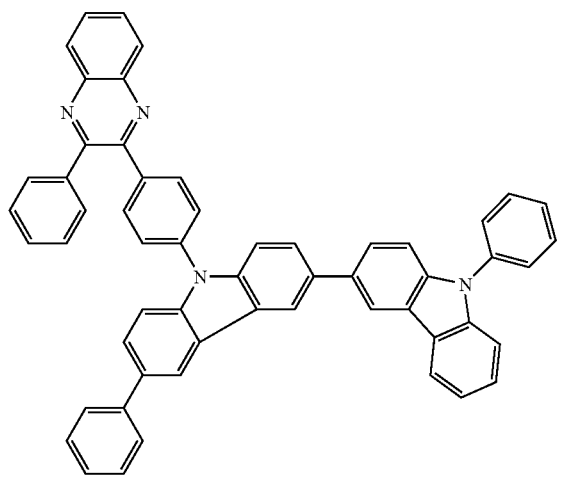
(40)
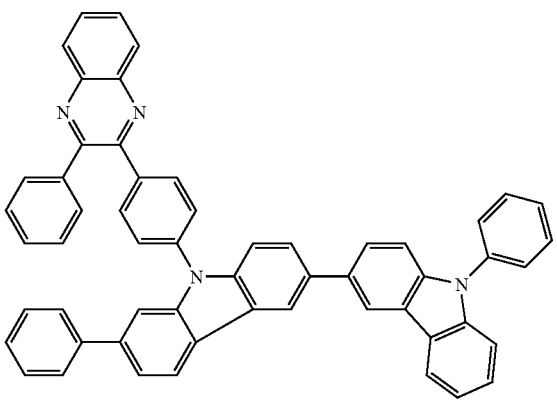
(41)
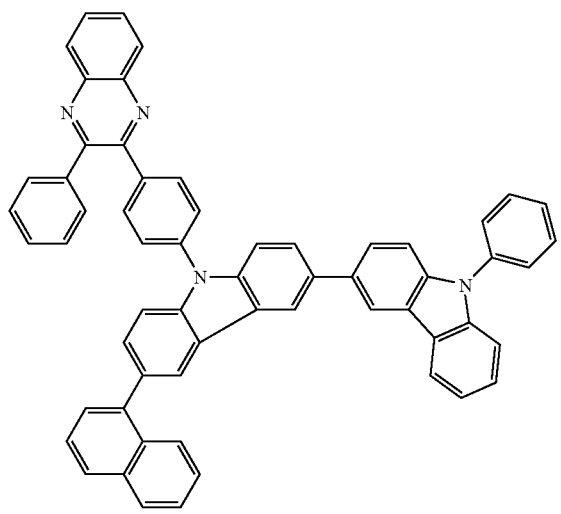
(42)
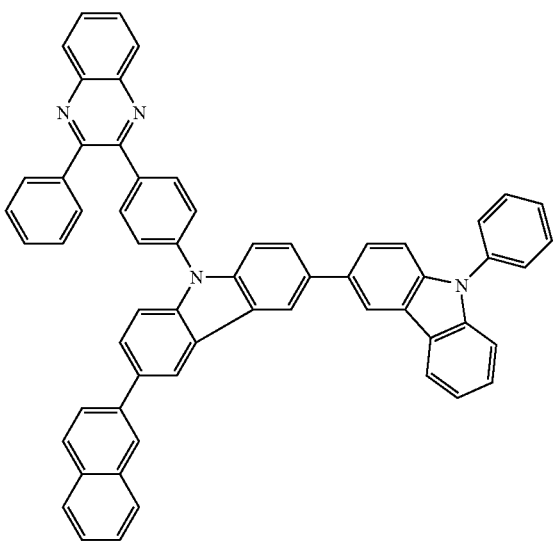

-continued
(43)
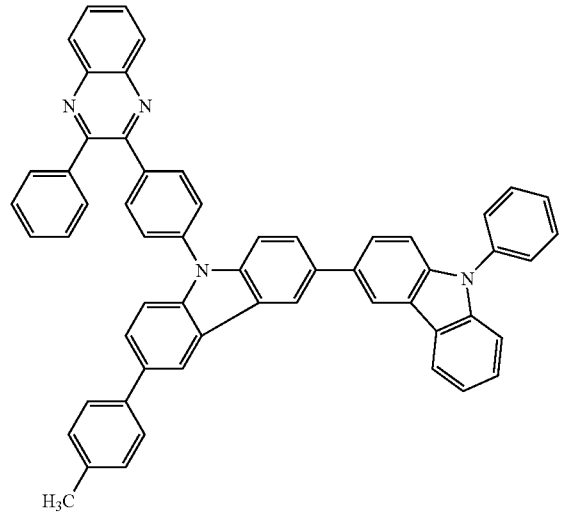
(44)
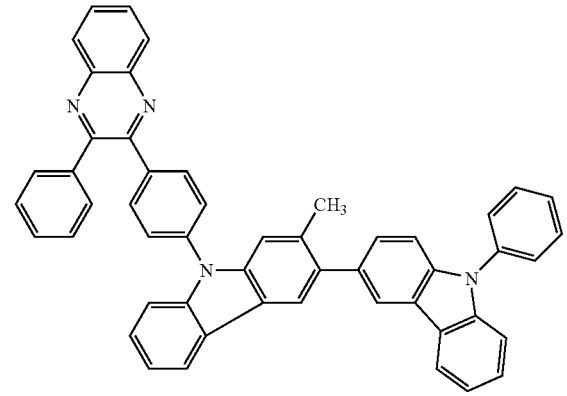
(45)
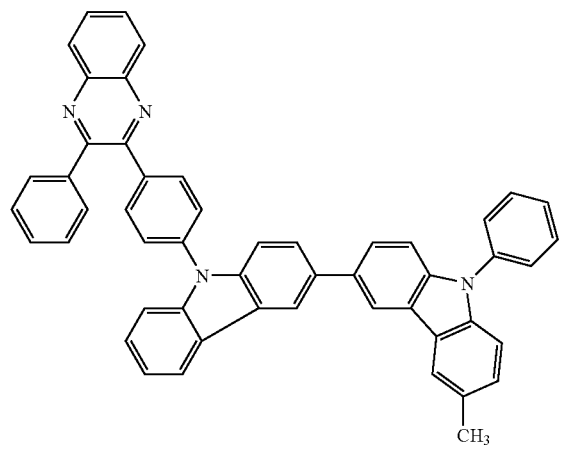
(46)
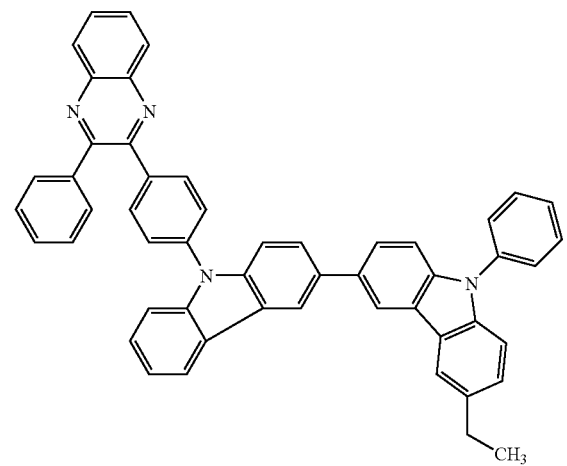
(47)
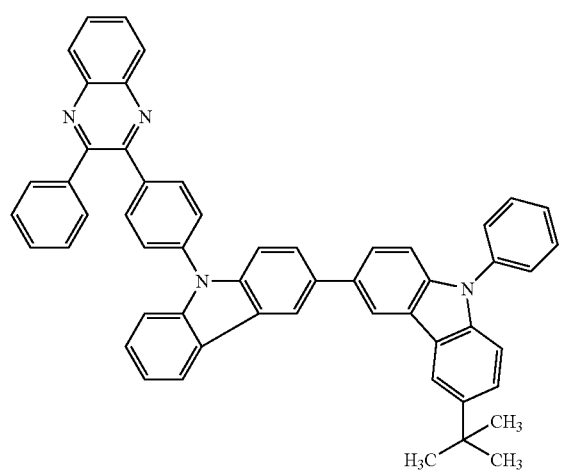
(48)
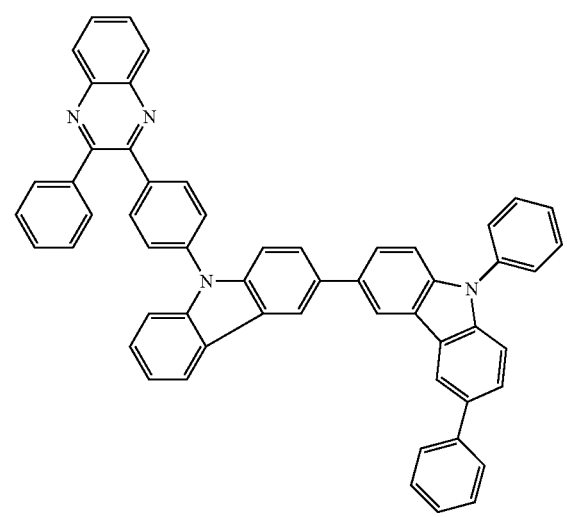

-continued
(49)
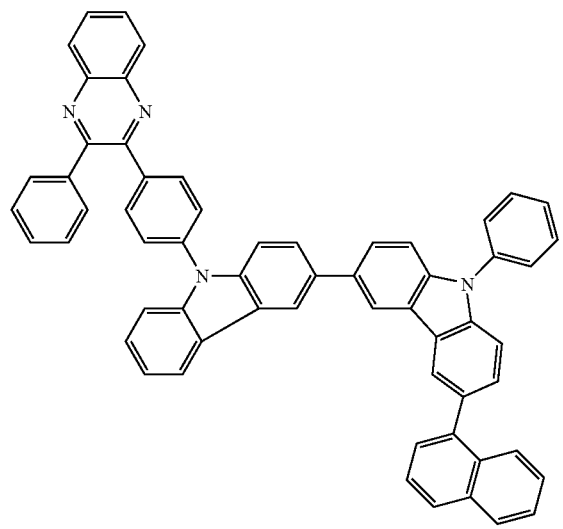
(50)
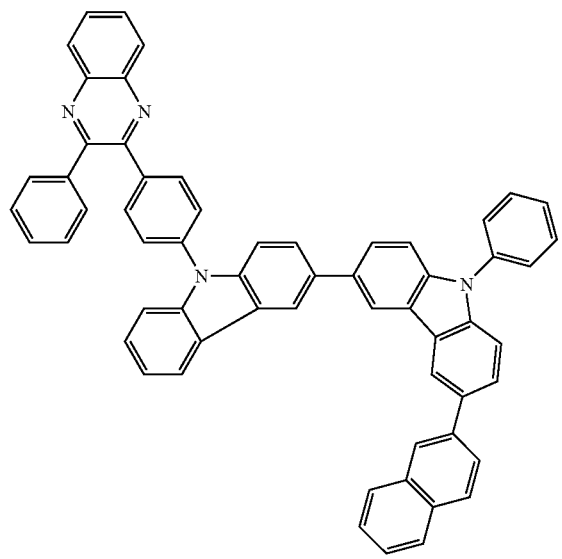
(51)
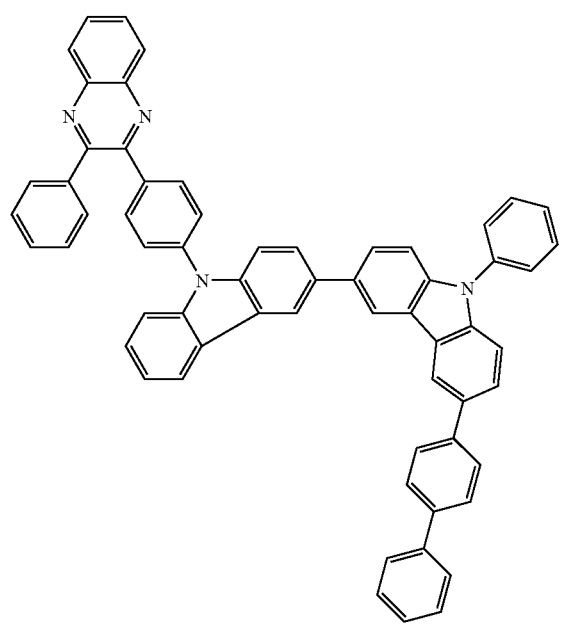
(52)
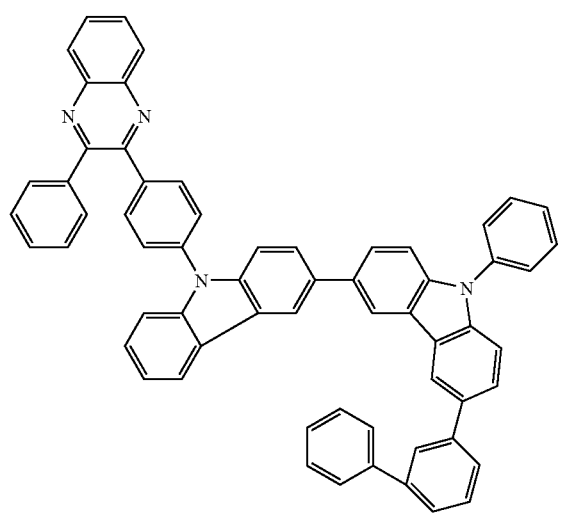

-continued
(53)
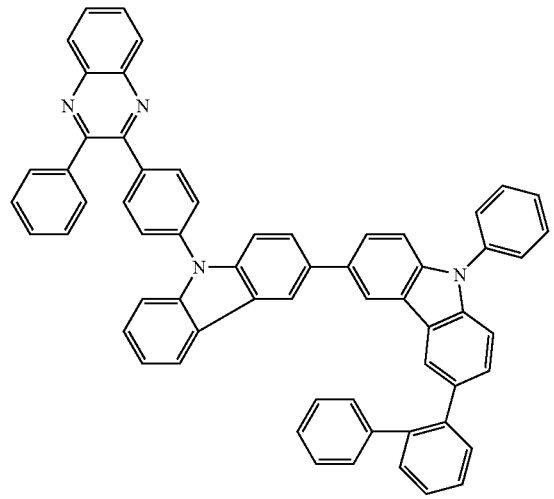
(54)
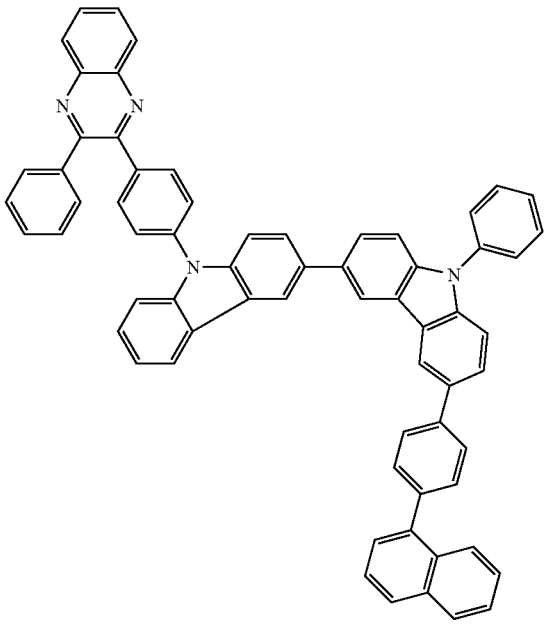
(55)
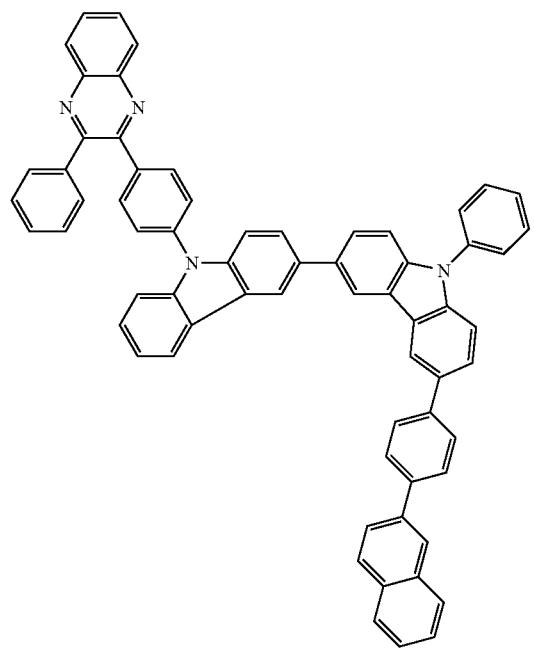
(56)
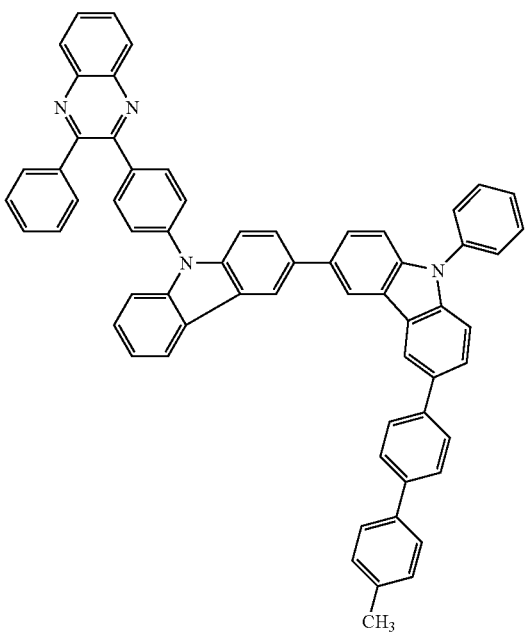
(57)
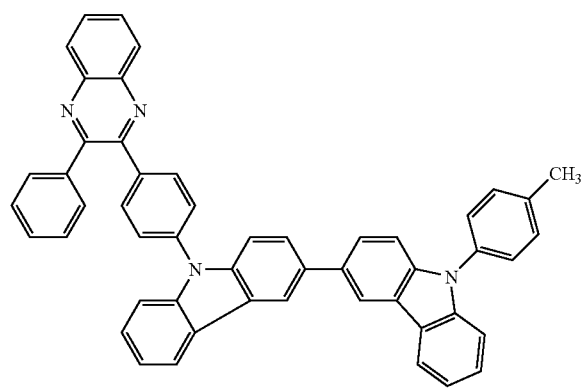
(58)
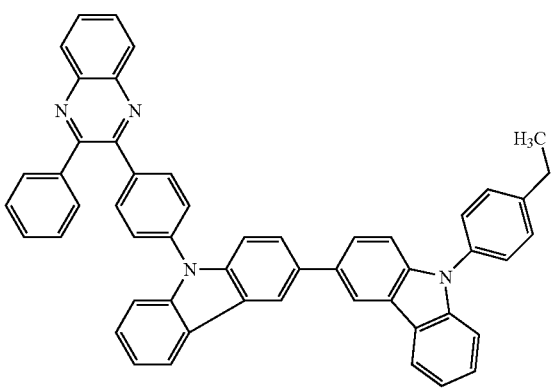

-continued
(59)
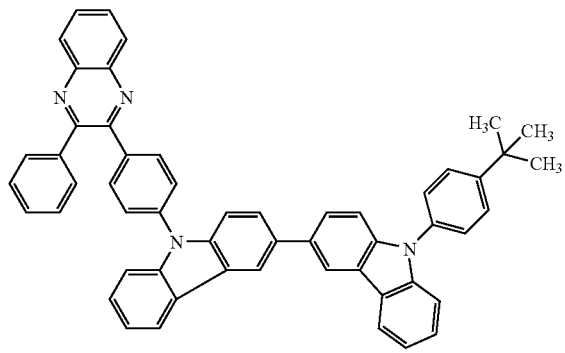
(60)
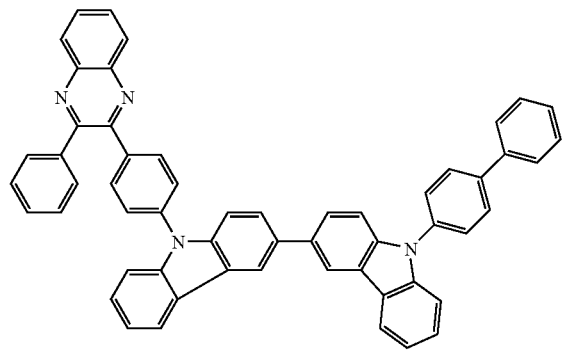
(61)
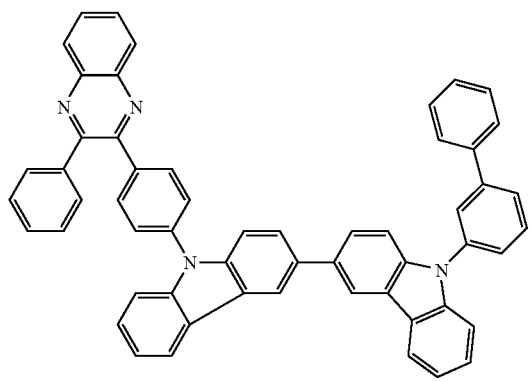
(62)
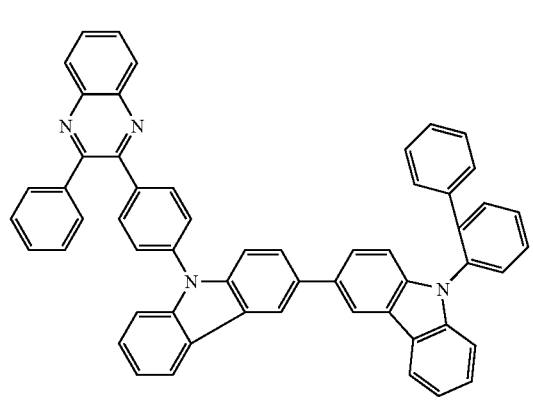
(63)
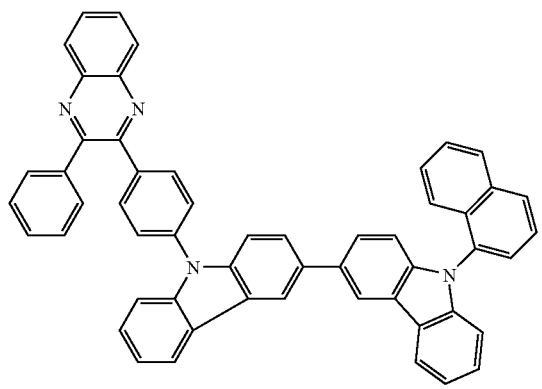
(64)
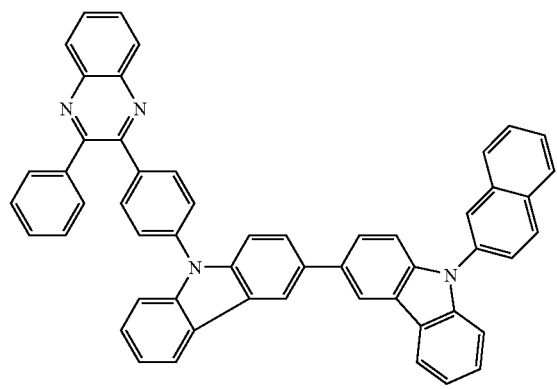
(65)
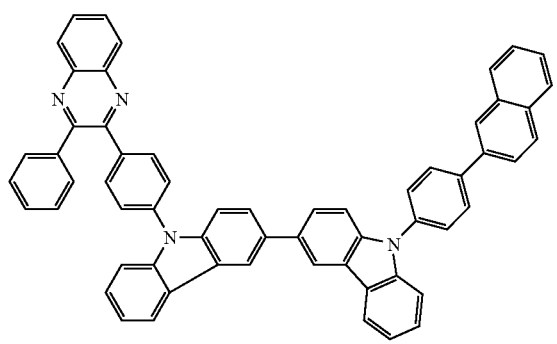
(66)
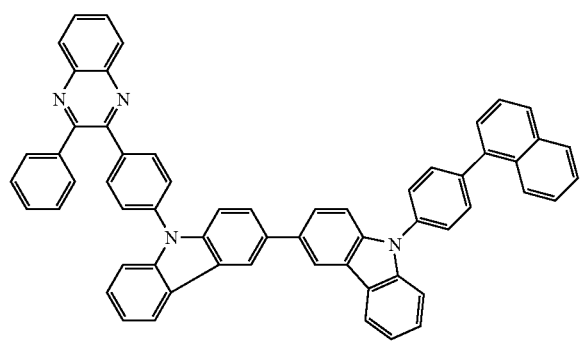

-continued
(67)
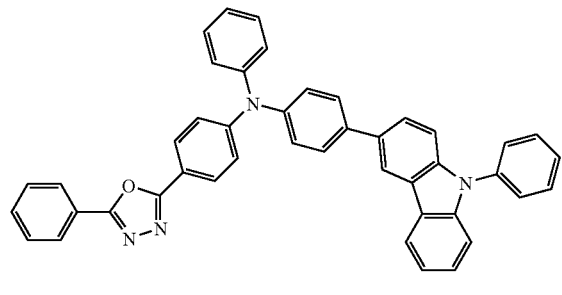
(68)
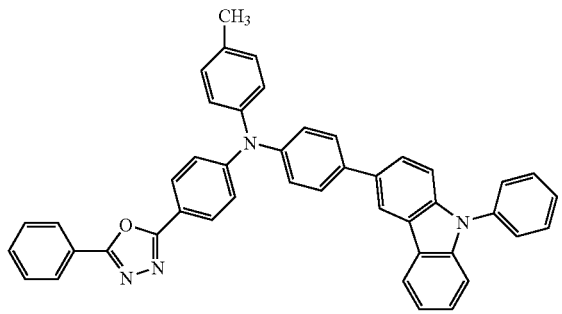
(69)
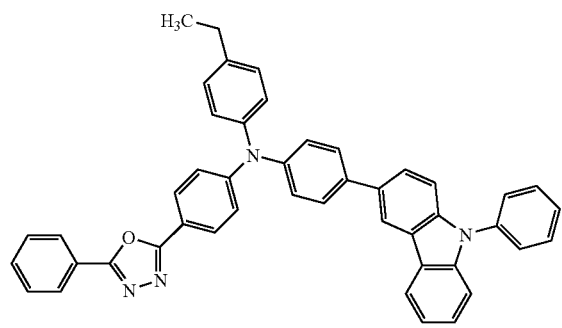
(70)
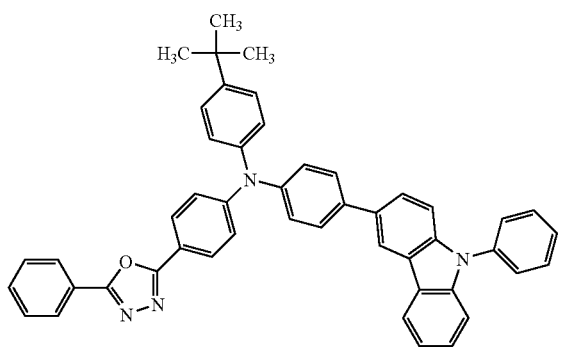
(71)
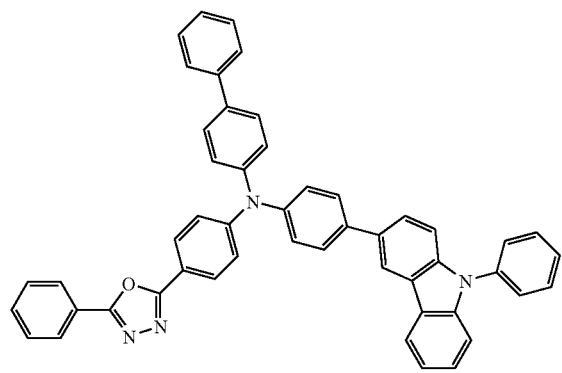
(72)
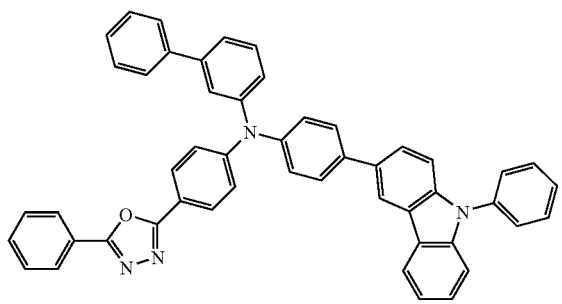
(73)
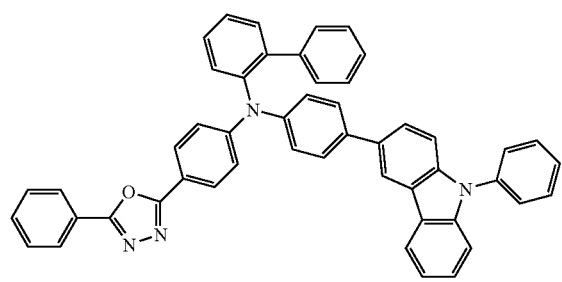
(74)
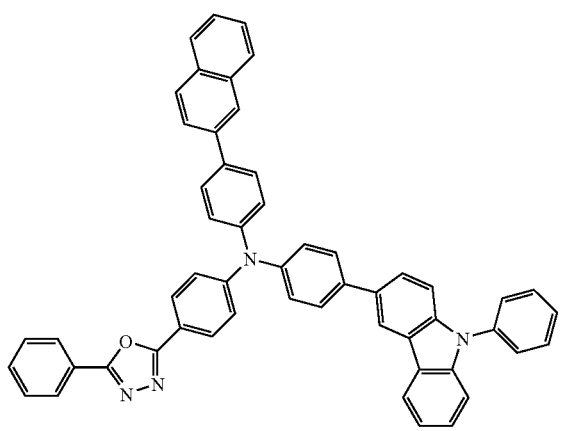

-continued
(75)
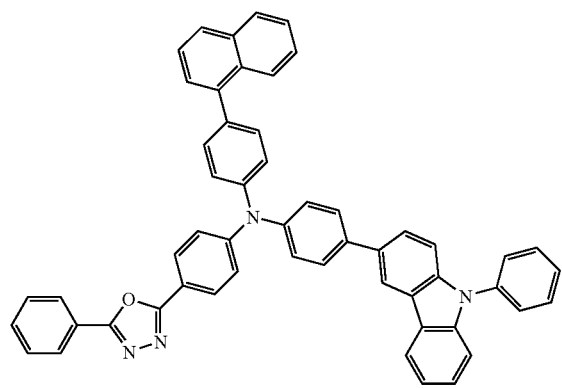
(76)
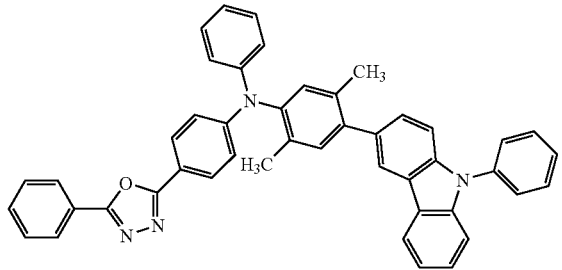
(77)
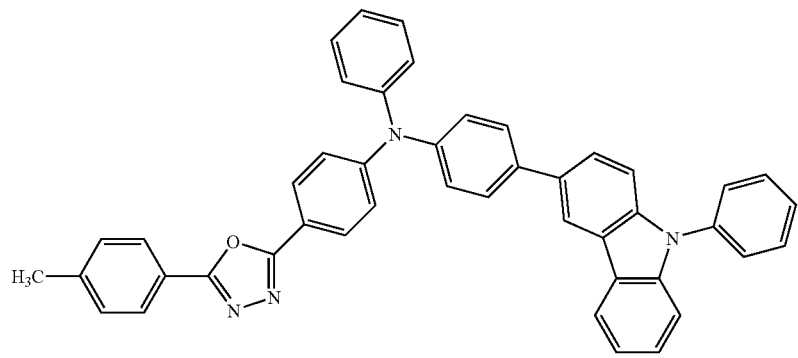
(78)
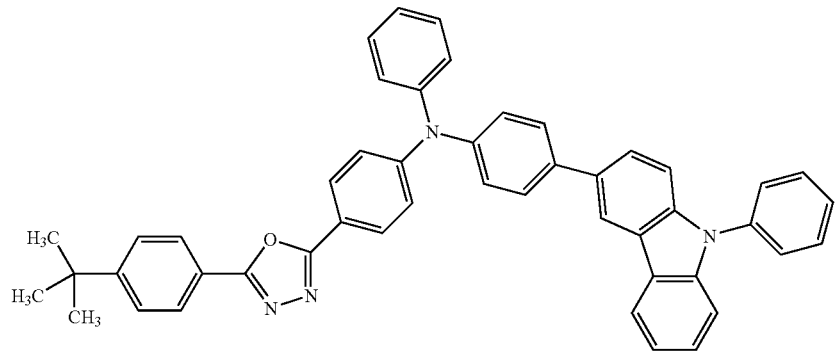
(79)
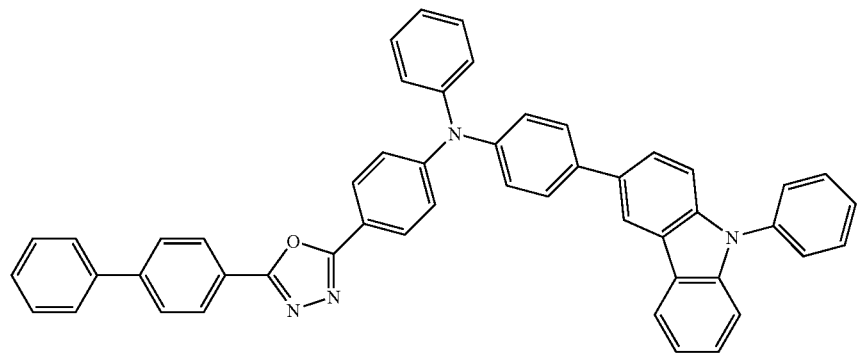

-continued
(80)
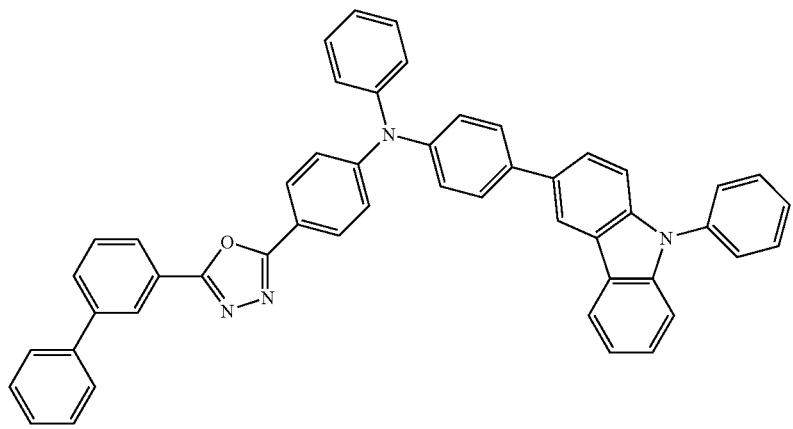
(81)
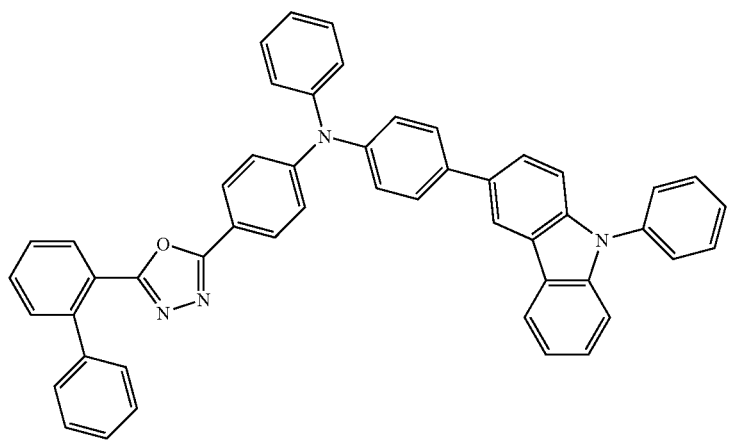
(82)
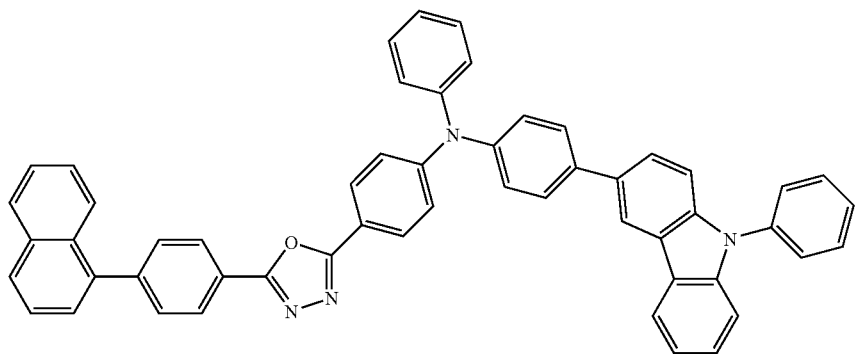
(83)
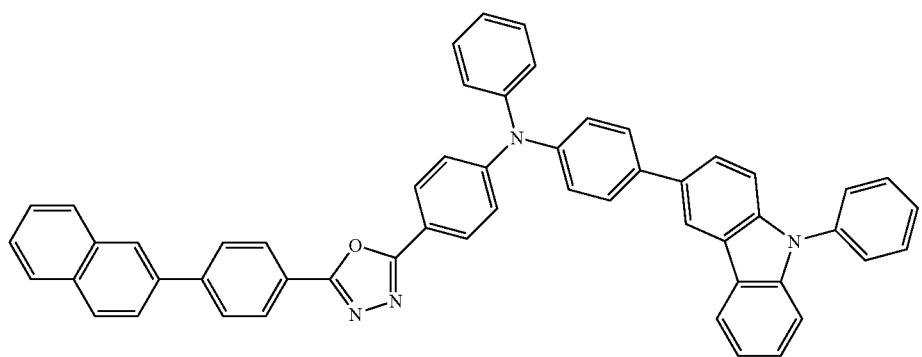

(84)
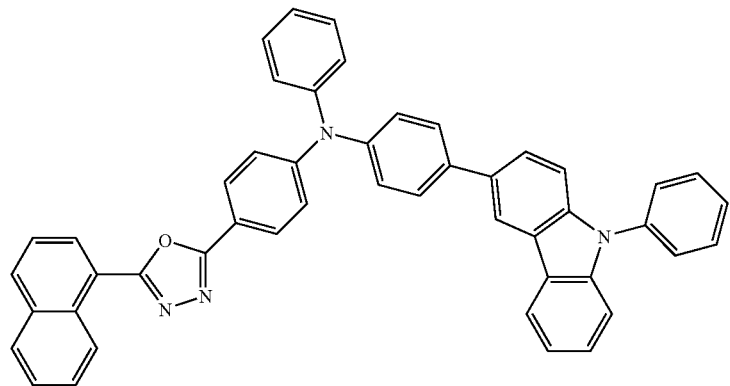
(85)
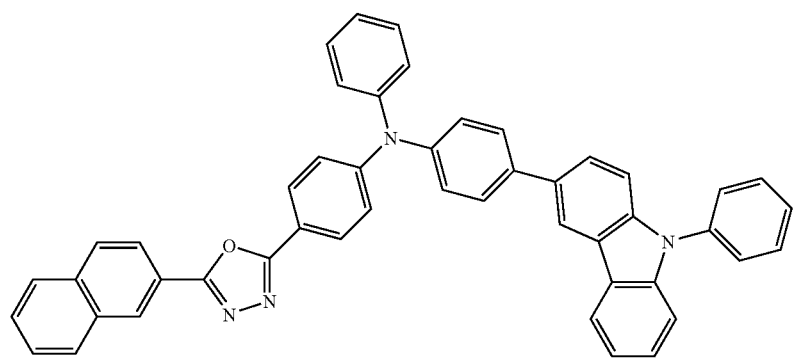
(86)
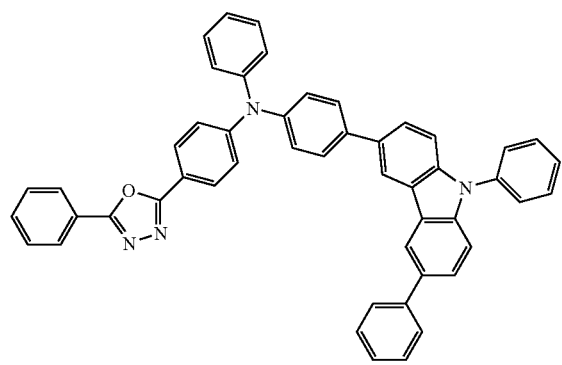
(87)
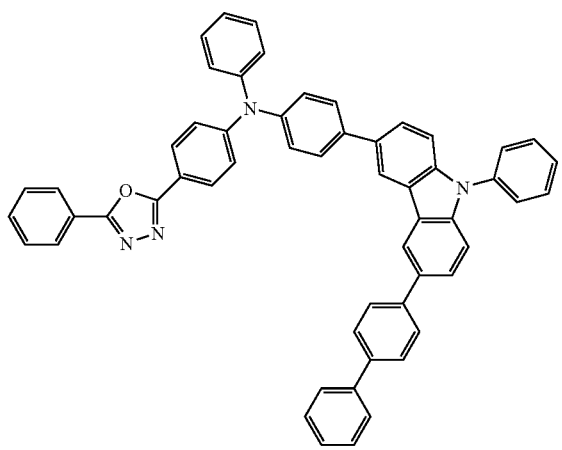

-continued
(88)
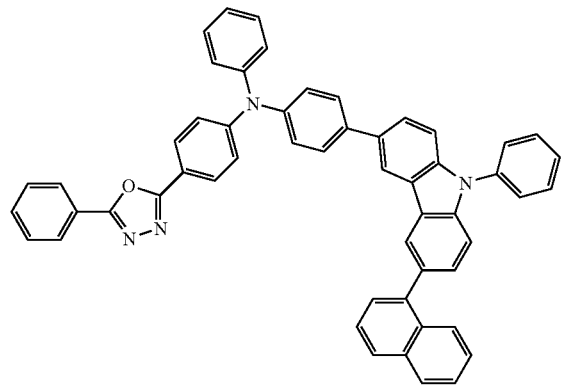
(89)
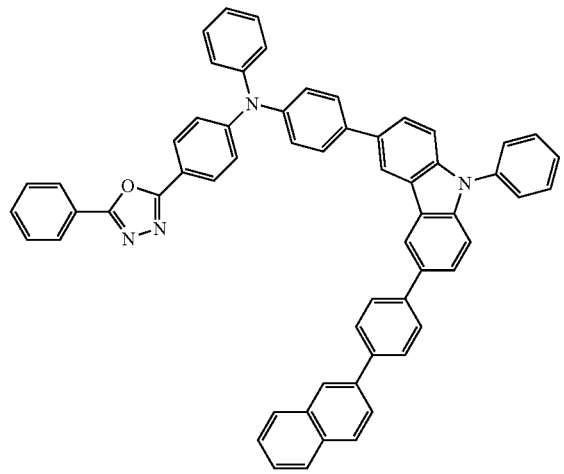
(90)
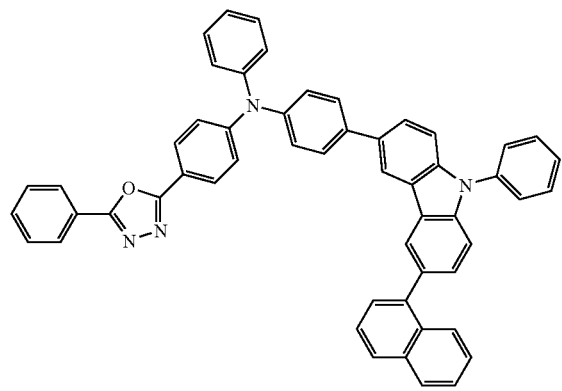
(91)
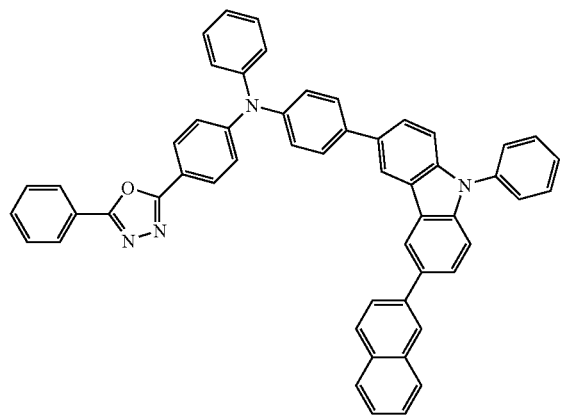
(92)
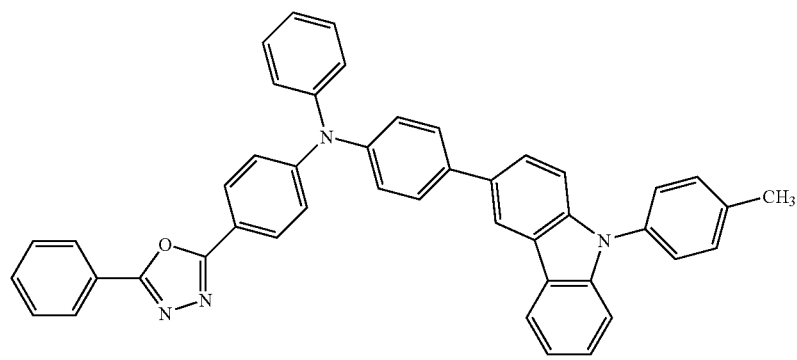
(93)
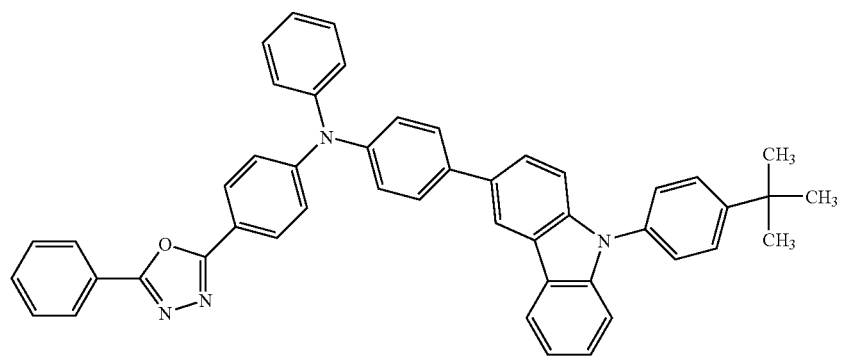

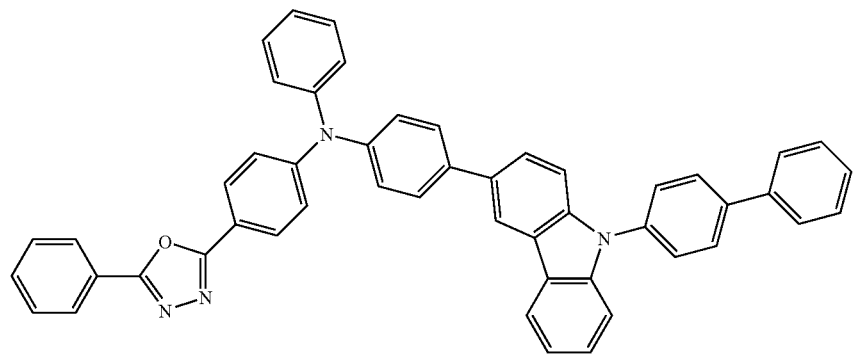
(94)
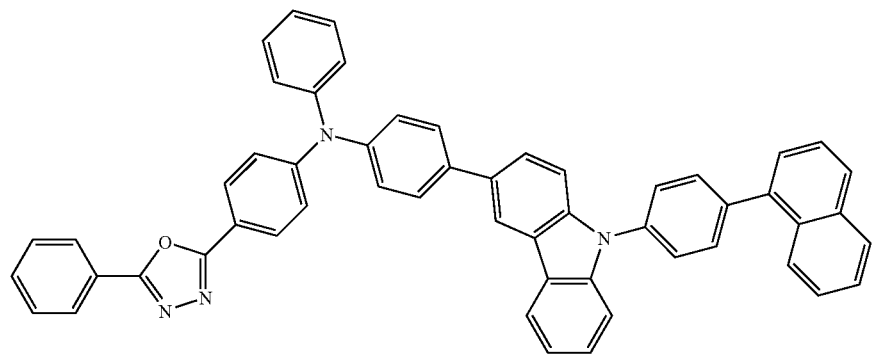
(95)
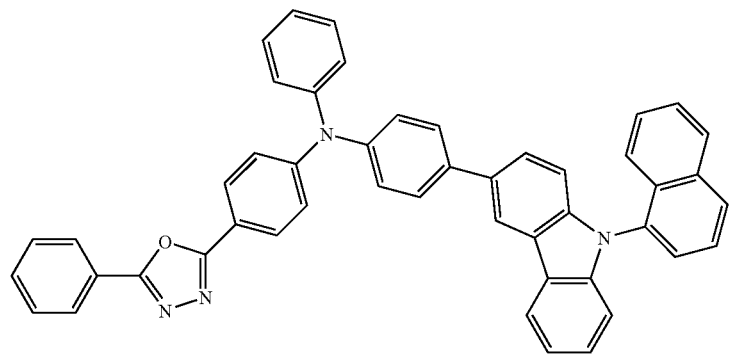
(96)
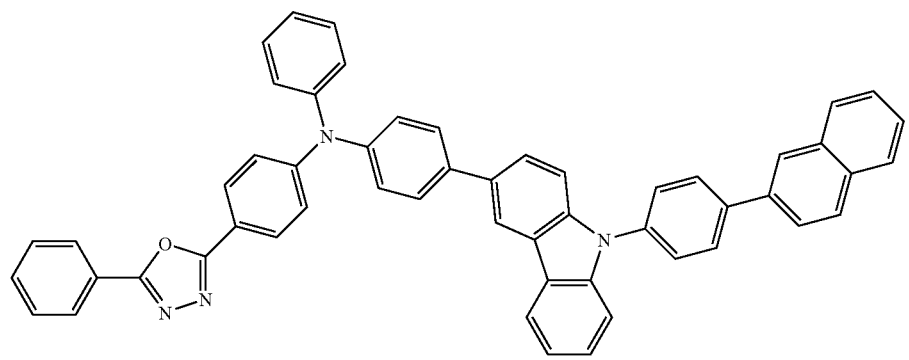
(97)

(98)
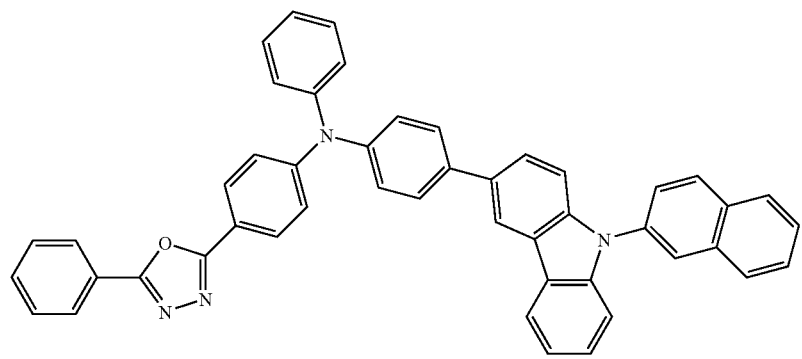
(99) (100)
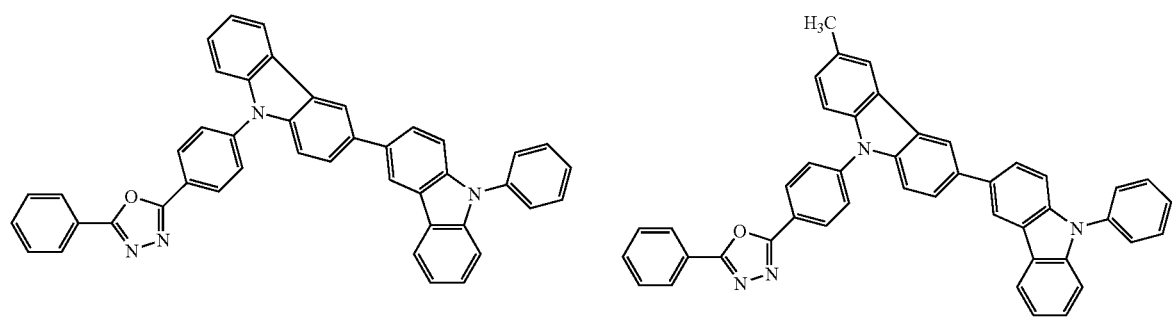
(101) (102)
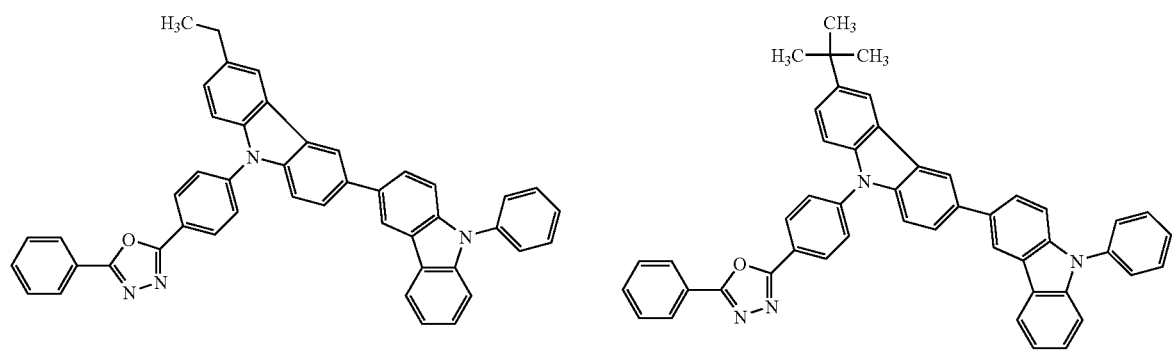
(103) (104)
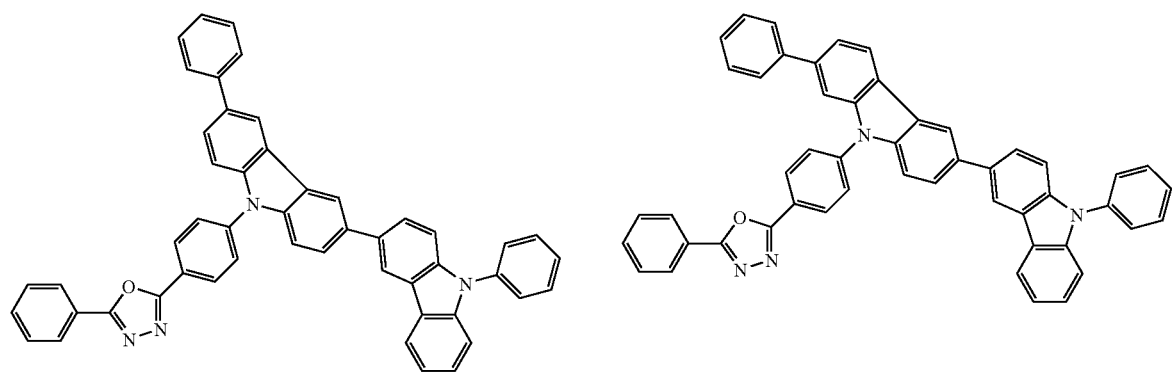

(105)
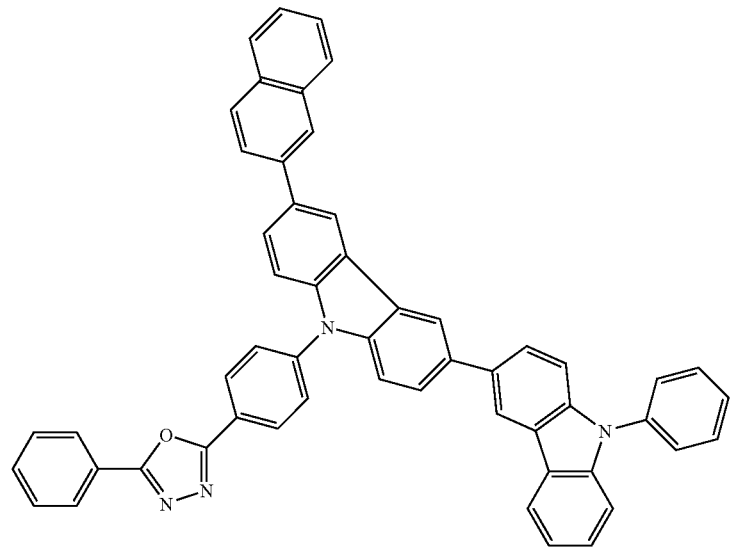
(106)
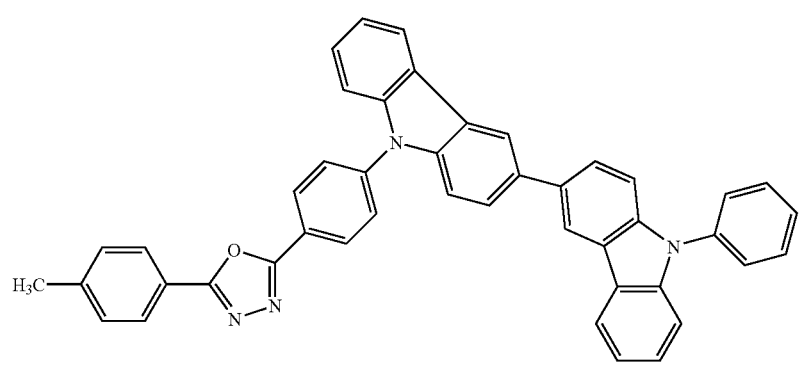
(107)
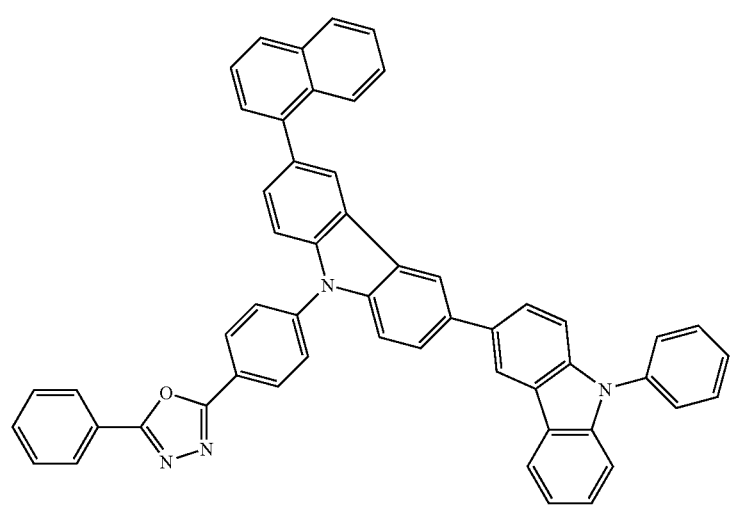

-continued
(108)
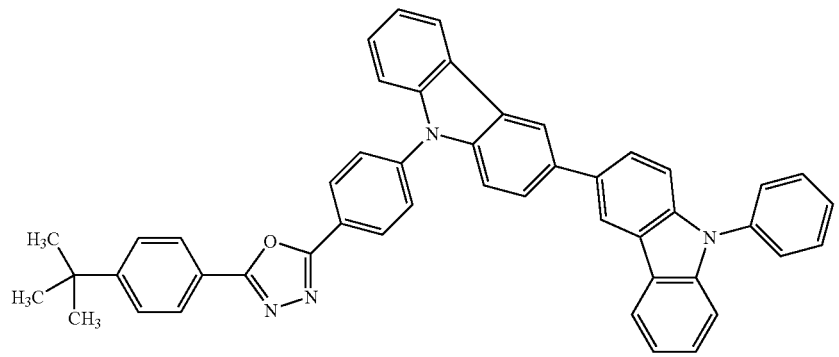
(109)
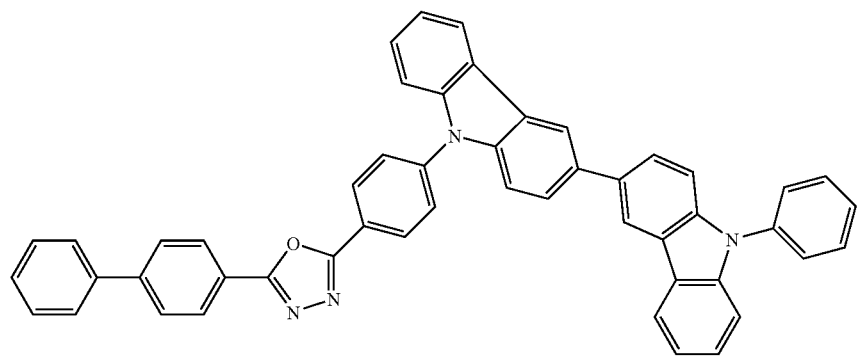
(110)
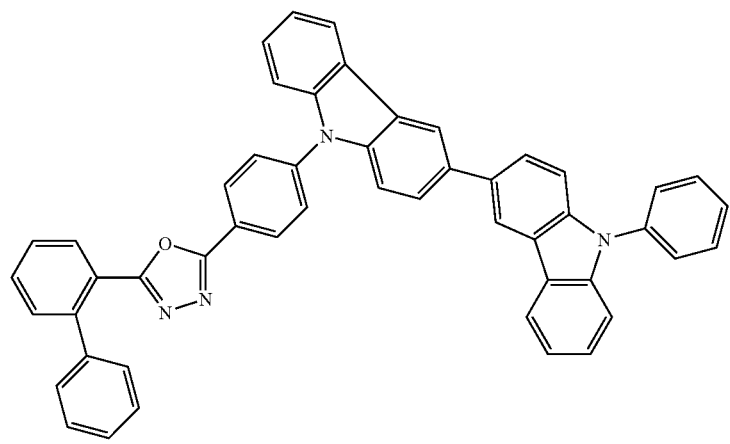
(111)
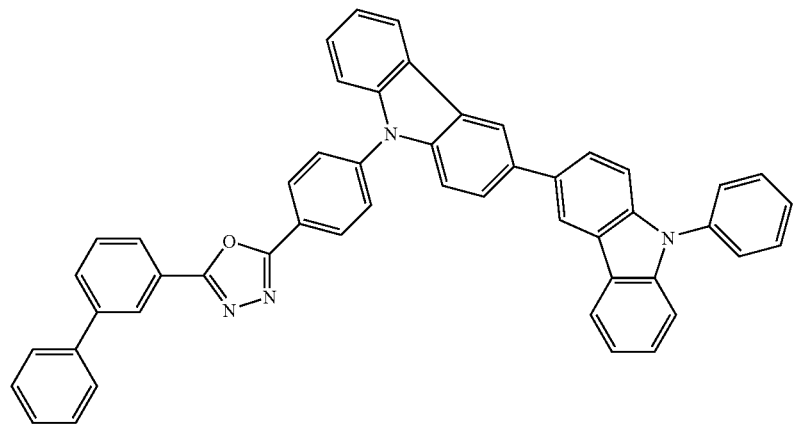

-continued
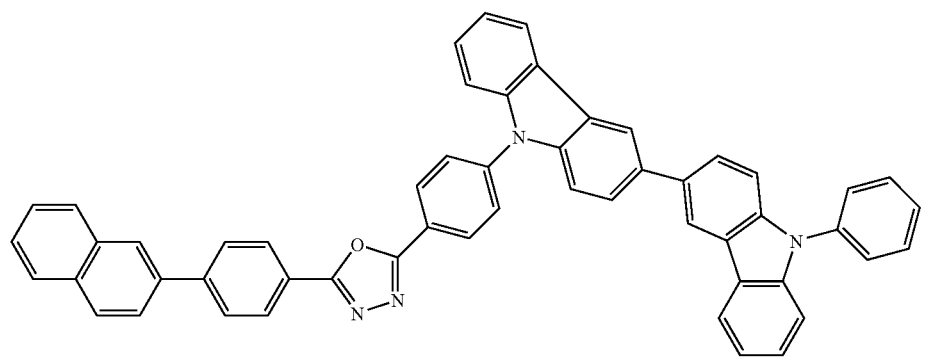
(112)
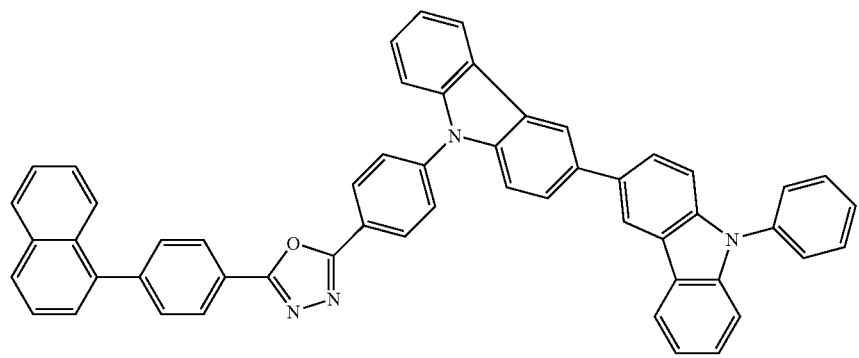
(113)
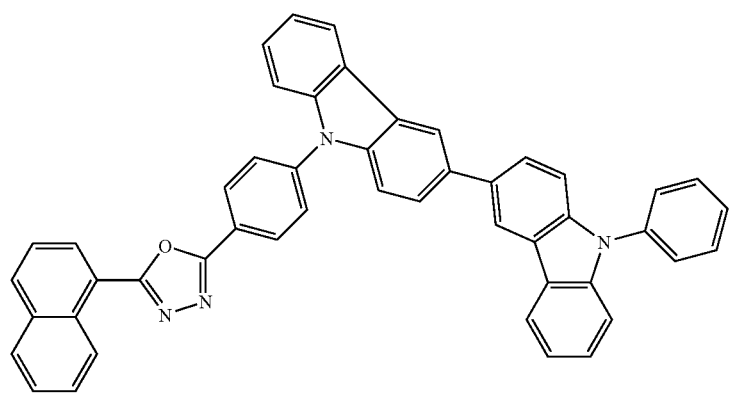
(114)
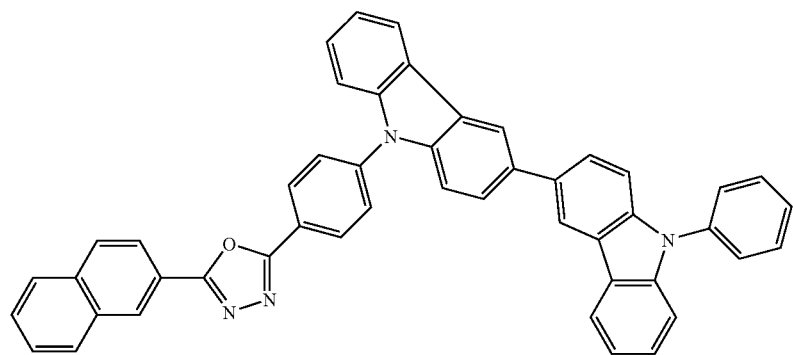
(115)

-continued
(116)
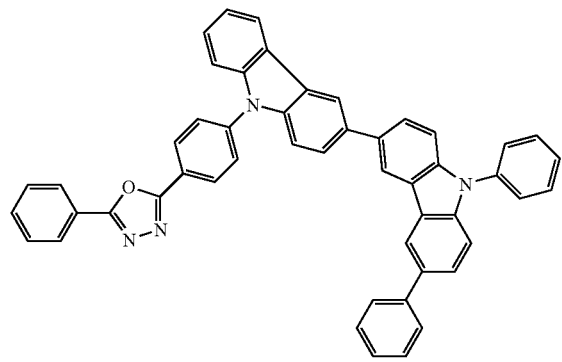
(117)
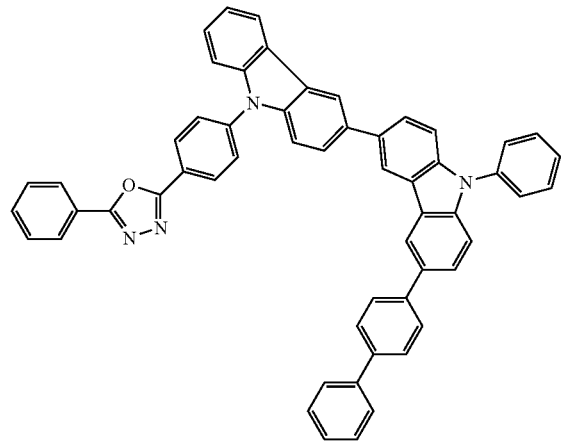
(118)
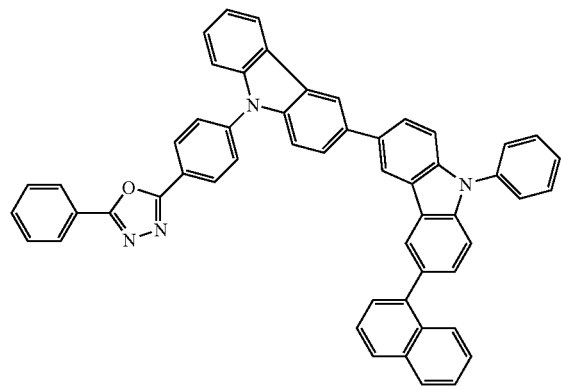
(119)
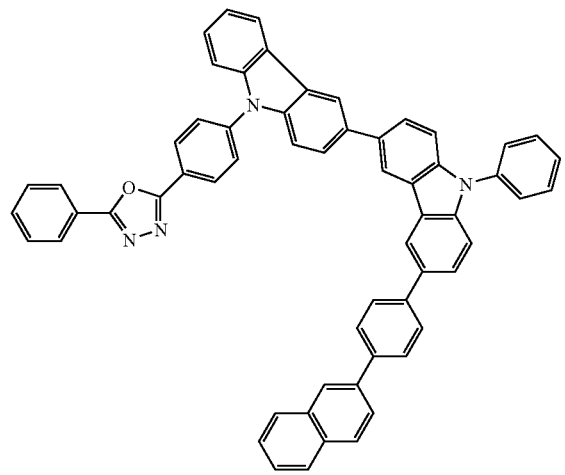
(120)
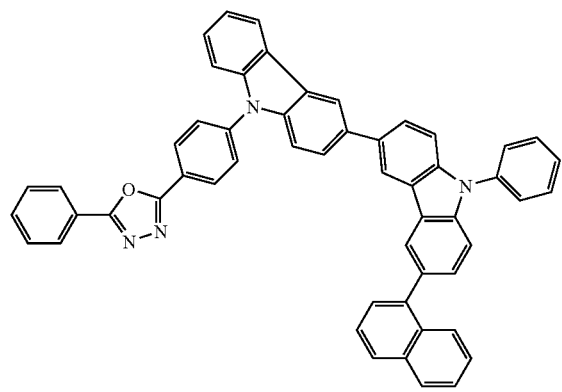
(121)
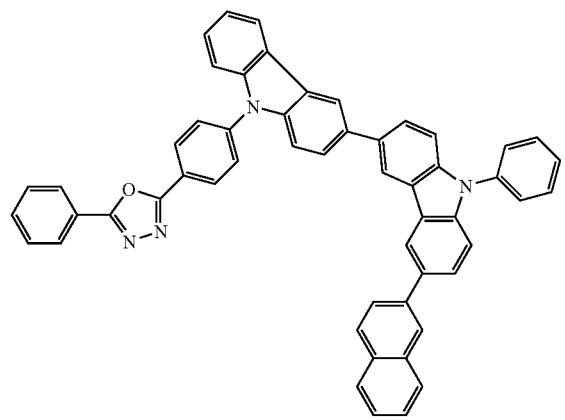

(122)
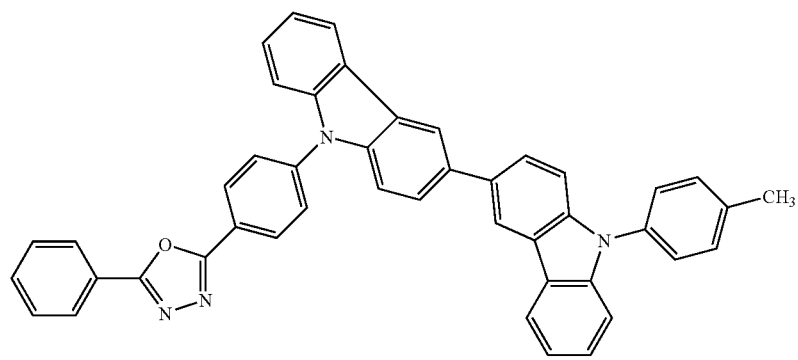
(123)
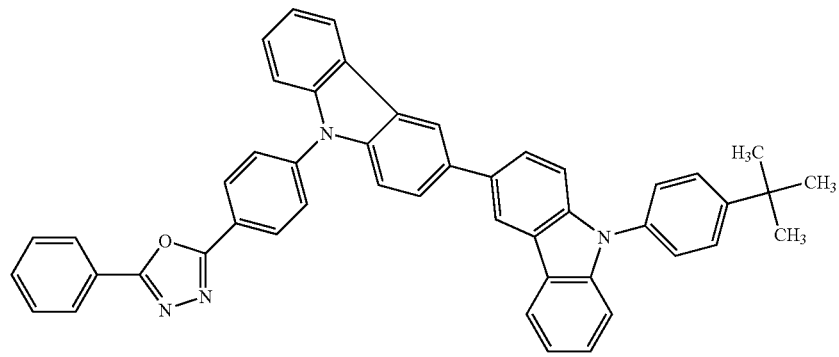
(124)
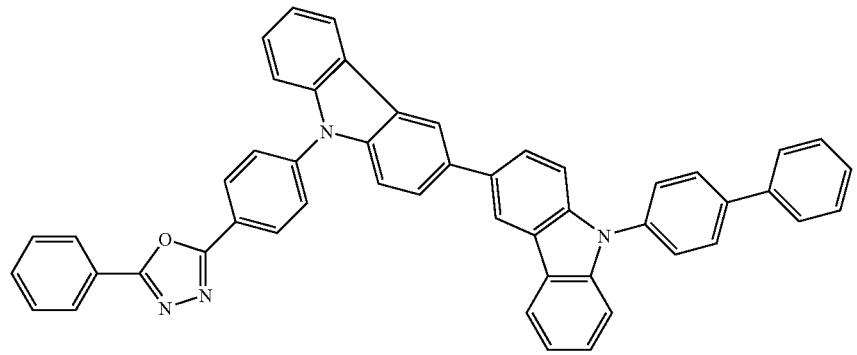
(125)
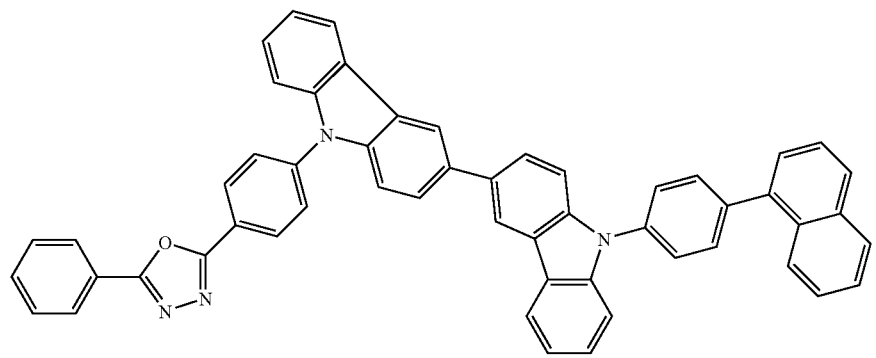

-continued (126)
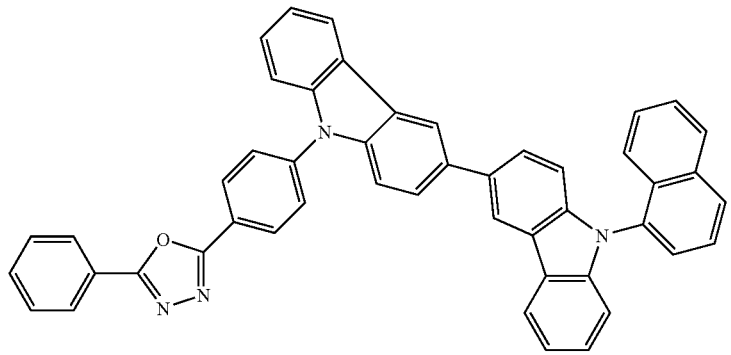

(127)
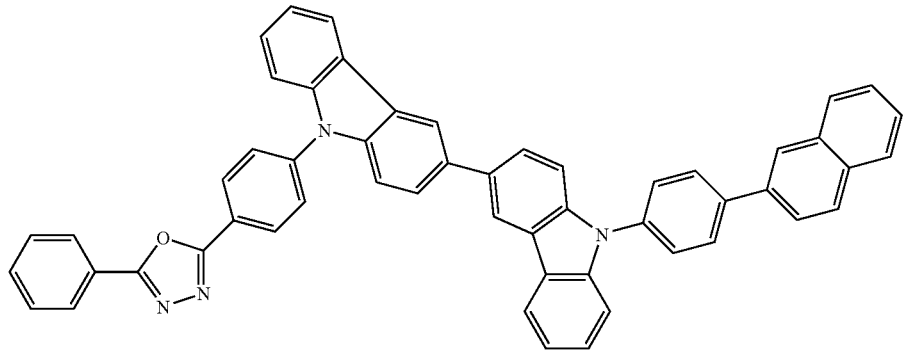

(128)
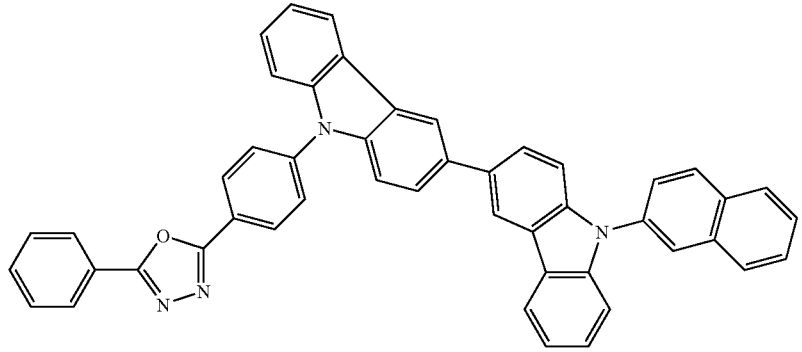

Next, an example of a synthetic method of the carbazole derivative having the heteroaromatic ring of an embodiment of the present invention will be described.

The carbazole derivative having the heteroaromatic ring represented by the general formula (G1) can be synthesized by the reaction of the carbazole derivative (A1) with the halogenated compound having a heteroaromatic ring (B1) as shown below.

(A1)
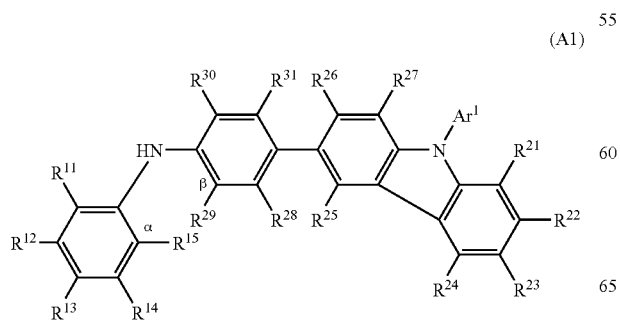

-continued (B1)
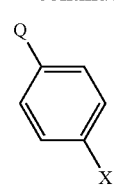
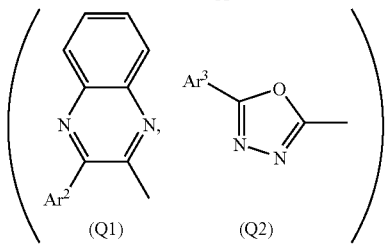

(In the formula, Q is a substituent represented by the general formula Q1 or Q2; X is a halogen atom; $Ar^1$ to $Ar^3$ each are an aryl group having 6 to 10 carbon atoms in a ring; and the aryl group optionally has a substituent. $R^{28}$ to $R^{31}$ each are a hydrogen atom or an alkyl group having 1 to 4 carbon atoms. $R^{11}$ to $R^{15}$ and $R^{21}$ to $R^{27}$ each are a hydrogen atom, an alkyl group having 1 to 4 carbon atoms, or an aryl group having 6 to 10 carbon atoms in a ring, and the aryl group optionally has a substituent. Note that the carbon at the α position and the carbon at the β position may be directly bonded to each other to form a carbazole ring.)

The synthetic scheme (M1) of the carbazole derivative having the heteroaromatic ring exemplified in the present embodiment is shown below.

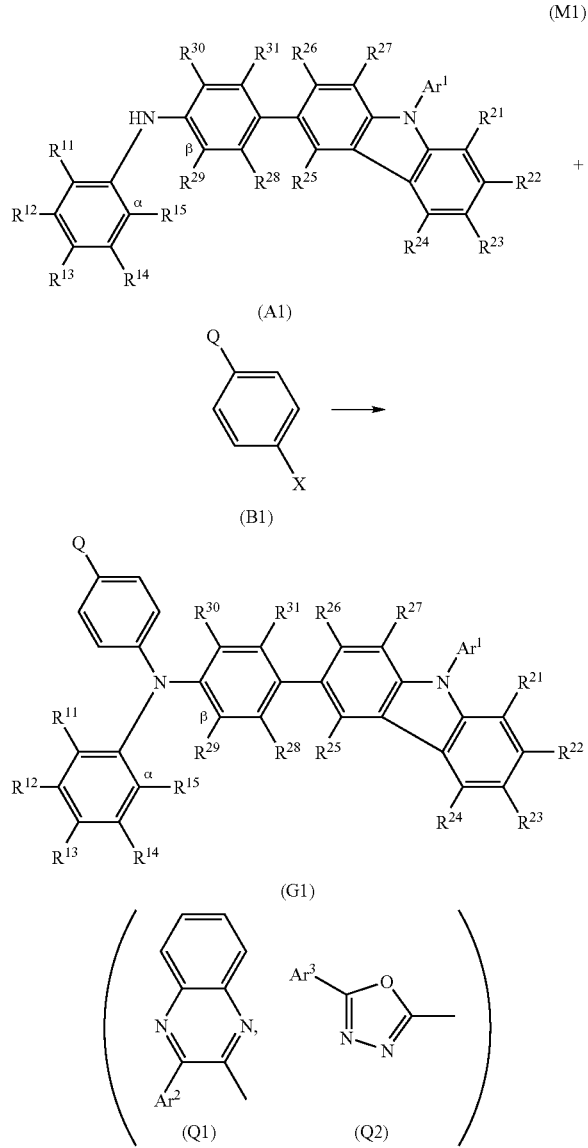

The substituent X in the halogenated compound (B1) having the heteroaromatic ring represents a halogen atom and is preferably iodine or bromine in the synthetic scheme (M1).

In the synthetic scheme (M1), the carbazole derivative (G1) having the heteroaromatic ring can be obtained by the coupling of the carbazole derivative (A1) with the halogenated compound (B1) having the heteroaromatic ring. The reaction shown in the synthetic scheme (M1) smoothly proceeds by applying the palladium catalyzed Hartwig-Buchwald reaction in the presence of a base, the Ullmann reaction using copper or a copper compound, or the like.

In the case of performing the Hartwig-Buchwald reaction, bis(dibenzylideneacetone)palladium(0), palladium(II)acetate, and the like can be given as the palladium catalyst. As a ligand of the palladium catalyst, tri(tert-butyl)phosphine, tri (n-hexyl)phosphine, tricyclohexylphosphine, and the like can be used. An organic base such as sodium tert-butoxide and an inorganic base such as potassium carbonate can be used as the base. As a solvent, toluene, xylene, benzene, tetrahydrofuran, and the like can be used.

In the case of performing the Ullmann reaction, copper can be used in addition to a copper compound such as copper(I) iodide and copper(II)acetate. An inorganic base such as potassium carbonate and the like can be used as the base. As a solvent, 1,3-dimethyl-3,4,5,6-tetrahydro-2(1H)-pyrimidinone (DMPU), toluene, xylene, benzene, and the like can be employed. DMPU or xylene which has a high boiling point is preferably used as the solvent because, in the case of the Ullmann reaction, an object can be obtained in a shorter time and in a higher yield when the reaction temperature is higher than or equal to 100° C. DMPU is more preferable since the reaction temperature equal to or higher than 150° C. is more preferred.

As mentioned above, although explanation is made using the reaction scheme (M1) as a synthetic example, the carbazole derivative (G1) having the heteroaromatic ring of an embodiment of the present invention may be synthesized by any other synthetic methods.

The aforementioned carbazole derivative having the heteroaromatic ring of an embodiment of the present invention possesses both an oxadiazole moiety or a quinoxaline moiety as the heteroaromatic ring having an electron-transporting property and a carbazole moiety having a hole-transporting property. Thus, it is a bipolar material having a high ability to transport electrons and holes. Additionally, it has a wide energy gap. As a result, the use of the carbazole derivative having the heteroaromatic ring of an embodiment of the present invention in a light-emitting layer or an electron-transporting layer enables the formation of a light-emitting element with excellent carrier balance.

Embodiment 2

In the present embodiment, a light-emitting element will be described with reference to FIGS. 1A to 1C, in which the carbazole derivative having the heteroaromatic ring of an embodiment of the present invention is used as a host material of a phosphorescent compound.

Figure 1B:
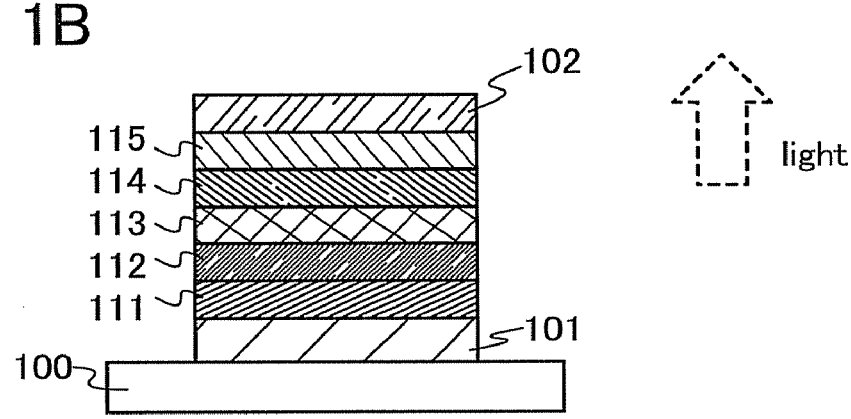
Figure 1C:
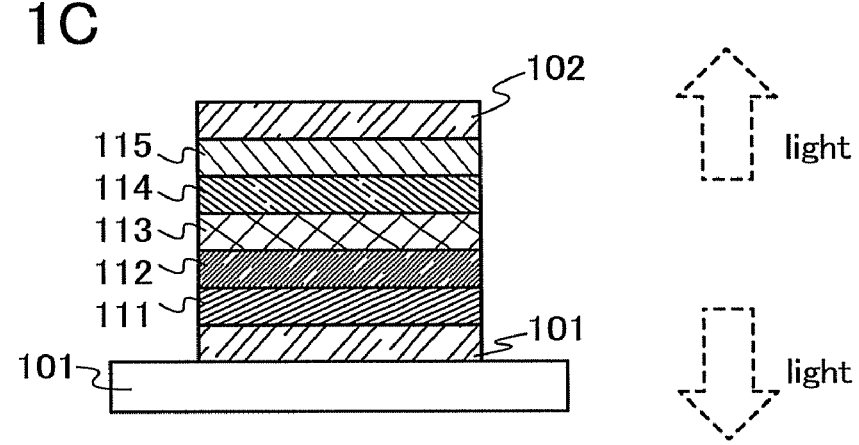

FIGS. 1A to 1C each illustrate a light-emitting element including a light-emitting layer 113 between a first electrode 101 and a second electrode 102. The light-emitting layer 113 includes, as the host material, the carbazole derivative having the heteroaromatic ring exemplified in the aforementioned Embodiment 1.

To the light-emitting element explained in the present embodiment, voltage is applied using the first electrode 101 and the second electrode 102 as an anode and a cathode, respectively. The holes injected from the first electrode 101 and the electrons injected from the second electrode 102 are transported to the light-emitting layer 113 including the carbazole derivative having the heteroaromatic ring. The holes and electrons are recombined in the light-emitting layer 113 to excite the phosphorescent compound used as the light-emitting substance. The phosphorescent compound in the excited state relaxes to the ground state to emit light, which allows the light-emitting element to function. The carbazole derivative having the heteroaromatic ring of an embodiment of the present invention can be used as the host material in the light-emitting layer, a hole-transporting material, an electron-transporting material, or the like of such a light-emitting (electroluminescence) element.

The light-emitting layer 113 of the present embodiment includes the carbazole derivative having the heteroaromatic ring of an embodiment of the present invention. Since the carbazole derivative having the heteroaromatic ring of an embodiment of the present invention has large excitation energy, it is suitable as the host material for the light-emitting substance. Note that the carbazole derivative having the heteroaromatic ring can be used alone as the light-emitting substance.

The light-emitting layer 113 is foamed by dispersing the light-emitting substance in the carbazole derivative having the heteroaromatic ring as the host material. Considering luminous efficiency, it is particularly preferred that the phosphorescent compound is dispersed as the light-emitting substance in the light-emitting layer 113. Dispersion of the phosphorescent compound in the host material can prevent quenching of light emission from the phosphorescent compound due to the increased concentration thereof.

In the case of using the phosphorescent material as the light-emitting substance, the triplet excitation energy thereof is required to be larger than that of the host material. Note that the triplet excitation energy is an energy difference between the triplet excited state and the ground state, and the singlet excitation energy is an energy difference between the singlet excited state and the ground state.

The carbazole derivative having the heteroaromatic ring of an embodiment of the present invention has large triplet excitation energy. Therefore, the light-emitting layer 113 can be formed, for example, by using the carbazole derivative having the heteroaromatic ring as the host material and dispersing a phosphorescent compound which emits red or green light as the light-emitting substance. The use of such a light-emitting layer 113 enables the formation of a light-emitting element with high luminous efficiency.

Organometallic complexes described below can be given as examples of the phosphorescent compound which can be used in the light-emitting layer 113 together with the carbazole derivative having the heteroaromatic ring of an embodiment of the present invention. Note that the phosphorescent compound used with the host material should be selected from the phosphorescent compounds having the triplet excitation energy smaller than that of the host material.

For example, as a light-emitting substance which exhibits green or green-tinged light emission, the following can be given: tris(2-phenylpyridinato-N,$C^{2'}$)iridium(III) (abbreviation: Ir(ppy)$_3$), bis[2-phenylpyridinato-N,$C^{2'}$]iridium(III) acetylacetonate (abbreviation: Ir(ppy)$_2$(acac)), bis(1,2-diphenyl-1H-benzimidazolato)iridium(III)acetylacetonate (abbreviation: Ir(pbi)$_2$(acac)), bis(benzo[h]quinolinato)iridium(III)acetylacetonate (abbreviation: Ir(bzq)$_2$(acac)), and the like.

As a light-emitting substance which exhibits yellow or yellow-tinged light emission, the following can be given: bis(2,4-diphenyl-1,3-oxazolato-N,$C^{2'}$)iridium(III)acetylacetonate (abbreviation: Ir(dpo)$_2$(acac)), bis{2-[4'-(perfluorophenylphenyl)pyridinato-N,$C^{2'}$]iridium(III)acetylacetonate (abbreviation: Ir(p-PF-ph)$_2$(acac)), bis(2-phenylbenzothiazolato-N,$C^{2'}$)iridium(III)acetylacetonate (abbreviation: Ir(bt)$_2$(acac)), and the like.

As a light-emitting substance which exhibits orange or orange-tinged light emission, the following can be given: tris(2-phenylquinolinato-N,$C^{2'}$)iridium(III) (abbreviation: Ir(pq)$_3$), bis(2-phenylquinolinato-N,$C^{2'}$)iridium(III)acetylacetonate (abbreviation: Ir(pq)$_2$(acac)), and the like.

As a light-emitting substance which exhibits red or red-tinged light emission, the following can be given: bis[2-(2'-benzo[4,5-a]thienyl)pyridinato-N,$C^{3'}$)iridium(III)acetylacetonate (abbreviation: Ir(btp)$_2$(acac)), bis(1-phenylisoquinolinato-N,$C^{2'}$)iridium(III)acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (2,3,7,8,12,13,17,18-octaethyl-21H,23H-porphyrinato)platinum(II) (abbreviation: PtOEP), and the like.

In addition, a rare earth metal complex such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), or tris[1-(2-thenoyl)-3,3,3-trifluoroacetonato](monophenanthroline)europium(III) (abbreviation: Eu(TTA)$_3$(Phen)) performs light emission (electron transition between different multiplicities) from a rare earth metal ion; therefore, such a rare earth metal complex can be used as a phosphorescent compound.

The carbazole derivative having the heteroaromatic ring of an embodiment of the present invention also possesses large singlet excitation energy. Therefore, the light-emitting layer 113 can be formed by using the carbazole derivative having the heteroaromatic ring as the host material and dispersing a variety of fluorescent compounds as the light-emitting substance. Compounds described below can be given as examples of the fluorescent compound which can be used in the light-emitting layer 113 together with the carbazole derivative having the heteroaromatic ring of an embodiment of the present invention.

For example, as a light-emitting substance which exhibits blue or blue-tinged light emission, the following can be given: 2,5,8,11-tetra(tert-butyl)perylene (abbreviation: TBP), 4,4'-bis(2,2-diphenylvinyl)biphenyl (abbreviation: DPVBi), 4,4'-bis[2-(9-ethylcarbazol-3-yl)vinyl]biphenyl (abbreviation: BCzVBi), bis(2-methyl-8-quinolinolato)(4-phenylphenolate)aluminum (abbreviation: BAlq), bis(2-methyl-8-quinolinolato)gallium chloride (abbreviation: Gamq$_2$Cl), N,N'-bis[4-(9H-carbazol-9-yl)phenyl]-N,N-diphenylstylbene-4,4'-diamine (abbreviation: YGA2S),4-(9H-carbazol-9-yl)-4'-(10-phenyl-9-anthryl)triphenylamine (abbreviation: YGAPA), and the like.

As a light-emitting substance which exhibits green or green-tinged light emission, the following can be given:
N-(9,10-diphenyl-2-anthryl)-N,9-diphenyl-9H-carbazol-3-amine (abbreviation: 2PCAPA),
N-[9,10-bis(1,1'-biphenyl-2-yl)-2-anthryl]-N,9-diphenyl-9H-carbazol-3-amine (abbreviation: 2PCABPhA),
N-(9,10-diphenyl-2-anthryl)-N,N',N'-triphenyl-1,4-phenylenediamine (abbreviation: 2DPAPA),
N-[9,10-bis(1,1'-biphenyl-2-yl)-2-anthryl]-N,N',N'-triphenyl-1,4-phenylenediamine (abbreviation: 2DPABPhA),
N-[9,10-bis(1,1'-biphenyl-2-yl)]-N-[4-(9H-carbazol-9-yl)phenyl]-N-phenylanthracen-2-amine (abbreviation: 2YGABPhA); N,N,9-triphenylanthracen-9-amine (abbreviation: DPhAPhA), and the like.

As a light-emitting substance which exhibits yellow or yellow-tinged light emission, 5,12-bis(1,1'-biphenyl-4-yl)-6,11-diphenyltetracene (abbreviation: BPT), and the like can be given.

As a light-emitting substance which exhibits red or red-tinged light emission, the following can be given: N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), and the like.

The carbazole derivative having the heteroaromatic ring of an embodiment of the present invention possesses both an oxadiazole moiety or a quinoxaline moiety as the heteroaromatic ring having an electron-transporting property and a carbazole moiety having a hole-transporting property. Thus, it is a bipolar material having a high ability to transport electrons and holes. The carbazole derivative having the heteroaromatic ring of an embodiment of the present invention can, therefore, be used alone as the host material to which the light-emitting substance is dispersed.

Furthermore, the carbazole derivative having the heteroaromatic ring of an embodiment of the present invention may be mixed with another material, and the mixture may be used as the host material to which the light-emitting substance is dispersed. For example, a material in which the carbazole derivative having the heteroaromatic ring of an embodiment of the present invention and an organic compound having a hole-transporting property or an electron-transporting property are mixed can be used as the host material.

Using a material, as a host, in which an organic compound having a hole-transporting property and an organic compound having an electron-transporting property are mixed is particularly effective as a method to obtain optimal carrier balance. Further, since the light-emitting region is expanded, it can be expected that luminous efficiency and reliability of the light-emitting element are increased.

As an organic compound having a hole-transporting property which can be used as a host material by being mixed together with the carbazole derivative having the heteroaromatic ring of an embodiment of the present invention, the following can be used: an aromatic amine compound such as 4,4'-bis[N-(1-naphtyl)-N-phenylamino]biphenyl (abbreviation: NPB), 4,4'-bis[N-(9-phenanthryl)-N-phenylamino]biphenyl (abbreviation: PPB), 4,4'-bis[N-(3-methylphenyl)-N-phenylamino]biphenyl (abbreviation: TPD), 4,4'-bis[N-(9,9-dimethylfluoren-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: m-MTDATA), 4,4',4''-tri(N-carbazolyl)triphenylamine (abbreviation: TCTA), 1,1-bis[4-(diphenylamino)phenyl]cyclohexane (abbreviation: TPAC), 9,9-bis[4-(diphenylamino)phenyl]fluorene (abbreviation: TPAF), 4-(9H-carbazolyl)-4'-(5-phenyl-1,3,4-oxadiazol-2-yl)triphenylamine (abbreviation: YGAO11), or N-[4-(9-carbazolyl)phenyl]-N-phenyl-9,9-dimethylfluoren-2-amine (abbreviation: YGAF); or a carbazole derivative such as 4,4'-di(N-carbazolyl)biphenyl (abbreviation: CBP), 1,3-bis(N-carbazolyl)benzene (abbreviation: mCP), or 1,3,5-tris(N-carbazolyl)benzene (abbreviation: TCzB).

Examples of organic compounds having an electron-transporting property which can be used as a host material by being mixed together with the carbazole derivative having the heteroaromatic ring of an embodiment of the present invention include a heteroaromatic compound such as 9-[4-(5-phenyl-1,3,4-oxadiazol-2-yl)phenyl]carbazole (abbreviation: CO11), 1,3-bis[5-(p-tert-buthylphenyl)-1,3,4-oxadiazol-2-yl]benzene (abbreviation: OXD-7), 2-(4-biphenylyl)-5-(4-tert-butylphenyl)-1,3,4-oxadiazole (abbreviation: PBD), 2,2',2''-(1,3,5-benzenetriyl)tris(1-phenyl-1H-benzimidazole) (abbreviation: TPBI), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), 9,9',9''-[1,3,5-triazine-2,4,6-triyl]tricarbazole (abbreviation: TCzTRZ), 2,2',2''-(1,3,5-benzenetriyl)tris(6,7-dimethyl-3-phenylquinoxaline) (abbreviation: TriMeQn), 2,3-bis(4-diphenylaminophenyl)quinoxaline (abbreviation: TPAQn), 9,9'-(quinoxaline-2,3-diyldi-4,1-phenylene)di(9H-carbazole) (abbreviation: CzQn), 3,3',6,6'-tetraphenyl-9,9'-(quinoxaline-2,3-diyldi-4,1-phenylene)di(9H-carbazole) (abbreviation: DCzPQ), bathophenanthroline (abbreviation: BPhen), or bathocuproine (abbreviation: BCP), and a metal complex such as tris(8-quinolinolato)aluminum (abbreviation: Almq$_3$), bis(2-methyl-8-quinolinolato)(4-phenylphenolato)aluminum(III) (abbreviation: BAlq), tris[2-(2-hydroxyphenyl)-5-phenyl-1,3,4-oxadiazolato]aluminum(III) (abbreviation: Al(OXD)$_3$), tris(2-hydroxyphenyl-1-phenyl-1H-benzimidazolato)aluminum(III) (abbreviation: Al(BIZ)$_3$), bis[2-(2-hydroxyphenyl)benzothiazolato]zinc(II) (abbreviation: Zn(BTZ)$_2$), bis[2-(2-hydroxyphenyl)benzoxazolato]zinc(II) (abbreviation: Zn(PBO)$_2$), or bis[2-(2-hydroxyphenyl)pyridinato]zinc (abbreviation: Znpp$_2$).

Note that the carbazole derivative having the heteroaromatic ring of an embodiment of the present invention can be used alone as the light-emitting layer in addition to as the host material of the light-emitting layer. Furthermore, it can be used as the light-emitting substance by being dispersed in a host material which has a larger band gap than the carbazole derivative having the heteroaromatic ring.

The light-emitting layer 113 can be formed by, for example, a sputtering method, an evaporation method, or the like.

It is also possible to form the light-emitting layer 113 by applying application liquid, in which the carbazole derivative having the heteroaromatic ring of an embodiment of the present invention and a light-emitting substance are dissolved or dispersed in an appropriate solvent, by means of a wet process such as an ink jet method or a spin coating method.

Examples of the solvents which can be used include, but are not limited to, an organic solvent having an aromatic ring such as toluene and methoxybenzene (anisole), an ether solvent such as diethyl ether, dioxane, and tetrahydrofuran (THF), an alcohol such as methanol, ethanol, isopropanol, butanol, 2-methoxyethanol, and 2-ethoxyethanol, acetonitrile, a mixed solvent thereof, and the like.

In the case where a plurality of organic thin films are stacked by a wet process, application liquid needs to be formed by selecting a solvent which dissolves a material to be deposited but does not dissolve a layer already formed as a base. In addition, the solvent is preferably a volatile organic solvent having a boiling point of from 50° C. to 200° C. so as not to remain in the films.

In the case where organic thin films are stacked by a wet process, a solution in which the light-emitting substance and the carbazole derivative having the heteroaromatic ring of an embodiment of the present invention are mixed may be applied. Moreover, the aforementioned organic compound having a hole-transporting property, the high molecular compound having a hole-transporting property, or the high molecular compound having an electron-transporting property may be added to the solution.

Furthermore, in order to improve properties of the film formed, a binder may be contained. For the binder, use of a high molecular compound that is electrically inactive is preferable. Specifically, poly(methyl methacrylate) (abbreviation: PMMA), polyimide, or the like can be used.

As the high molecular compounds having a hole-transporting property, poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTP- DMA), poly[N,N'-bis(4-butylphenyl)-N,N'-bis(phenyl) benzidine (abbreviation: Poly-TPD), or the like can be used.

Examples of the high molecular compounds having an electron-transporting property which can be used for the host material include poly(2,5-pyridinediyl) (abbreviation: PPy), poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy), and the like.

In FIGS. 1A to 1C, a substrate 100 is used as a base of the light-emitting element. As the substrate 100, for example, a glass substrate, a plastic substrate, or the like may be used. Note that materials other than glass or plastic can be used as long as they can function as a support of a light-emitting element.

Although there is no particular limitation on the first electrode 101, it is preferably formed using a substance having a high work function in the case of functioning as an anode as in this embodiment. Specifically, it is possible to use indium tin oxide (ITO), indium tin oxide containing silicon oxide (ITSO), indium oxide containing zinc oxide at 2 to 20 wt % (IZO), gold (Au), platinum (Pt), nickel (Ni), tungsten (W), chromium (Cr), molybdenum (Mo), iron (Fe), cobalt (Co), copper (Cu), palladium (Pd), or the like. Note that the first electrode 101 can be formed, for example, by a sputtering method, an evaporation method, or the like.

Although there is also no particular limitation on the second electrode 102, it is preferably formed using a substance having a low work function in the case of functioning as a cathode as in this embodiment. Specifically, it is possible to use aluminum (Al), indium (In), an alkali metal such as lithium (Li) or cesium (Cs), an alkaline-earth metal such as magnesium (Mg) or calcium (Ca), a rare-earth metal such as erbium (Er) or ytterbium (Yb), or the like. Alternatively, an alloy such as an aluminum-lithium alloy (AlLi) or a magnesium-silver alloy (MgAg) can be used. Note that the second electrode 102 can be formed by, for example, a sputtering method, an evaporation method, or the like.

Light is extracted outside through at least one of the first electrode 101 and the second electrode 102. Thus, in order to extract emitted light to the outside, at least one of the first electrode 101 and the second electrode 102 is an electrode formed using a conductive film which can transmit visible light, such as ITO, or an electrode with a thickness of several nanometers to several tens nanometers so as to transmit visible light. In a case where only the first electrode 101 is made of a light-transmitting conductive film, emitted light is extracted through the first electrode 101 and the substrate 100 as illustrated in FIG. 1A. In a case where only the second electrode 102 is made of a light-transmitting conductive film, emitted light is extracted through the second electrode 102 as illustrated in FIG. 1B. In a case where both the first electrode 101 and the second electrode 102 are made of a light-transmitting conductive film, emitted light is extracted from both upper and lower sides of the light-emitting element through both the first electrode 101 and the second electrode 102 as shown in FIG. 1C.

In addition, as illustrated in FIGS. 1A to 1C, a hole-transporting layer 112 may be provided between the first electrode 101 and the light-emitting layer 113. Here, a hole-transporting layer is a layer which has a function of transporting holes injected from the first electrode 101 to the light-emitting layer 113. Since thus provided hole-transporting layer 112 is able to separate the first electrode 101 from the light-emitting layer 113, quenching of emitted light due to a metal can be prevented. However, the hole-transporting layer 112 is not necessarily provided.

There is no particular limitation on a substance forming the hole-transporting layer 112, and any of the following substances can be typically used: an aromatic amine compound such as 4,4'-bis[N-(1-naphthyl)-N-phenylamino]biphenyl (abbreviation: NPB), 4,4'-bis[N-(3-methylphenyl)-N-phenylamino]biphenyl (abbreviation: TPD), 4,4'-bis[N-(9,9-dimethylfluoren-2-yl)-N-phenylamino]biphenyl (abbreviation: DFLDPBi), 4,4',4''-tris(N,N-diphenylamino)triphenylamine (abbreviation: TDATA), and 4,4',4''-tris[N-(3-methylphenyl)-N-phenylamino]triphenylamine (abbreviation: m-MTDATA). In addition, a macromolecular compound such as poly(4-vinyltriphenylamine) (abbreviation: PVTPA) or the like can also be used.

Note that the hole-transporting layer 112 may have a multilayer structure in which two or more layers are stacked. In addition, the hole-transporting layer 112 may also be formed by mixing two or more types of substances.

As illustrated in FIGS. 1A to 1C, an electron-transporting layer 114 may be further provided between the second electrode 102 and the light-emitting layer 113. Here, the electron-transporting layer is a layer having a function of transporting electrons injected from the second electrode 102 to the light-emitting layer 113. By thus providing the electron-transporting layer 114 to separate the second electrode 102 from the light-emitting layer 113, quenching of emitted light by a metal in the neighboring second electrode 102 can be prevented. Note that the electron-transporting layer 114 is not necessarily provided.

There is no particular limitation on a substance forming the electron-transporting layer 114, and the following can be typically given: metal complexes such as tris(8-quinolinolato)aluminum (abbreviation: Alq$_3$), tris(4-methyl-8-quinolinolato)aluminum (abbreviation: Almq$_3$), bis(10-hydroxybenzo[h]quinolinato)beryllium (abbreviation: BeBq$_2$), bis(2-methyl-8-quinolinolato)(4-phenylphenolato)aluminum (abbreviation: BAlq), bis[2-(2-hydroxyphenyl)benzoxazolato]zinc (abbreviation: ZnBOX), and bis[2-(2-hydroxyphenyl)benzothiazolato]zinc (abbreviation: Zn(BTZ)$_2$). Further, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tent-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can also be used. A polymer such as poly(2,5-pyridindiyl) (abbreviation: PPy) can be also used. Note that the electron-transporting layer 114 may have a multilayer structure in which two or more layers are stacked and also may be formed by mixing two or more types of substances.

Since the carbazole derivative having the heteroaromatic ring of an embodiment of the present invention is a bipolar material with high electron- and hole-transporting properties, it can be used as a material for the hole-transporting layer or the electron-transporting layer. In particular, since the carbazole derivative having the heteroaromatic ring of an embodiment of the present invention has high excitation energy, an exciton generated in the light-emitting layer can be prevented from diffusing into another layer by using it in a layer adjacent to the light-emitting layer. As a result, a light-emitting element with high luminous efficiency can be obtained.

As illustrated in FIGS. 1A to 1C, a hole-injecting layer 111 may be further provided between the first electrode 101 and the hole-transporting layer 112. Here, the hole-injecting layer refers to a layer having a function of assisting injection of holes from an electrode serving as an anode to the hole-transporting layer 112. Note that the hole-injecting layer 111 is not necessarily provided.

There is no particular limitation on a substance forming the hole-injecting layer 111, and the following can be used: a metal oxide such as vanadium oxide, niobium oxide, tantalum oxide, chromium oxide, molybdenum oxide, tungsten oxide, manganese oxide, rhenium oxide, and ruthenium oxide. In addition, a phthalocyanine compound such as phthalocyanine (abbreviation: $H_2Pc$), copper phthalocyanine (abbreviation: CuPc), or the like can also be used. Alternatively, any of the substances for forming the aforementioned hole-transporting layer 112 can also be used. Further alternatively, a high molecular compound such as a mixture of poly (ethylenedioxythiophene) and poly(styrene sulfonate) (abbreviation: PEDOT/PSS) can be used.

Still alternatively, for the hole-injecting layer 111, a composite material formed by combining an organic compound and an electron acceptor may be used. Such a composite material is superior in hole-injecting property and hole-transporting property, since holes (cation radicals) are generated in the organic compound by the electron acceptor. In this case, the organic compound is preferably a material excellent in transporting the generated holes. Specifically, the above-described substances for following the hole-transporting layer 112 (e.g., an aromatic amine compound) can be used for example.

As the electron acceptor, any substance can be used as long as it shows an electron-accepting property to the organic compound. Specifically, a transition metal oxide is preferable, and examples thereof include vanadium oxide, niobium oxide, tantalum oxide, chromium oxide, molybdenum oxide, tungsten oxide, manganese oxide, rhenium oxide, ruthenium oxide, and the like. Lewis acid such as iron chloride(III) or aluminum chloride(III) can also be used. Alternatively, an organic compound such as 7,7,8,8-tetracyano-2,3,5,6-tetrafluoroquinodimethane (abbreviation: $F_4$-TCNQ) can be used. Note that the hole-injecting layer 111 may have a multilayer structure in which two or more layers are stacked.

As illustrated in FIGS. 1A to 1C, an electron-injecting layer 115 may be further provided between the second electrode 102 and the electron-transporting layer 114. Here, the electron-injecting layer refers to a layer which has the function of assisting injection of electrons from an electrode serving as a cathode to the electron-transporting layer 114. Note that the electron-injecting layer 115 is not necessarily provided.

Although there is no particular limitation on a substance forming the electron-injecting layer 115, and an alkali metal compound or an alkaline earth metal compound such as lithium fluoride (LiF), cesium fluoride (CsF), calcium fluoride ($CaF_2$), or lithium oxide can be used. Alternatively, a rare earth metal compound like erbium fluoride ($ErF_3$) can be used. Furthermore, the above-mentioned substances for forming the electron-transporting layer 114 can also be used.

For the electron-injecting layer 115, a composite material formed by combining an organic compound and an electron donor to the organic compound may also be used. Such a composite material is superior in electron-injecting property and electron-transporting property, since electrons are generated in the organic compound by the electron donor. In this case, the organic compound is preferably a material excellent in transporting the generated electrons. Specifically, the above-described materials for forming the electron-transporting layer 114 (e.g., a metal complex or a heteroaromatic compound) can be used for example. As the electron donor, a substance exhibiting an electron-donating property to the organic compound may be used, and it is preferable to use an alkali metal, an alkaline-earth metal, or a rare earth metal such as lithium, cesium, magnesium, calcium, erbium, or ytterbium. Further, an alkali metal oxide or an alkaline-earth metal oxide is preferable, and lithium oxide, calcium oxide, barium oxide, and the like are exemplified. Alternatively, Lewis base such as magnesium oxide can also be used. Further alternatively, an organic compound such as tetrathiafulvalene (abbreviation: TTF) can be used.

In the foregoing light-emitting element, each of the hole-injecting layer 111, the hole-transporting layer 112, the light-emitting layer 113, the electron-transporting layer 114, and the electron-injecting layer 115 may be formed by any method, for example, an evaporation method, an inkjet method, an application method, or the like. In addition, each of the first electrode 101 and the second electrode 102 may also be formed by any of a sputtering method, an evaporation method, or the like, or a wet process such as an inkjet method or a coating method.

The carbazole derivative having the heteroaromatic ring of an embodiment of the present invention possesses both an oxadiazole moiety or a quinoxaline moiety as the heteroaromatic ring having an electron-transporting property and a carbazole moiety having a hole-transporting property. Thus, it is a bipolar material having a high ability to transport electrons and holes. Additionally, it has a wide energy gap. Therefore, the use of the carbazole derivative having the heteroaromatic ring of an embodiment of the present invention in a light-emitting layer or a carrier-transporting layer enables the formation of a light-emitting element with excellent luminous efficiency.

Note that this embodiment can be freely combined with the other embodiments.

Embodiment 3

In this embodiment, a light-emitting element having a structure different from those described in Embodiment 2 is described with reference to FIGS. 2A and 2B.

Figure 2A:
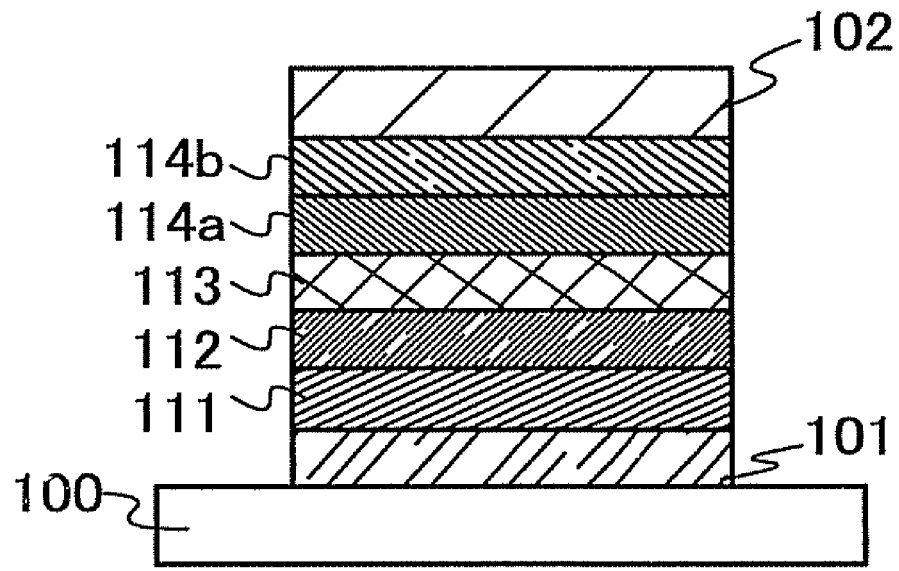
FIGS. 2A and 2B each illustrate a light-emitting element according to an embodiment of the present invention.
Figure 2B:
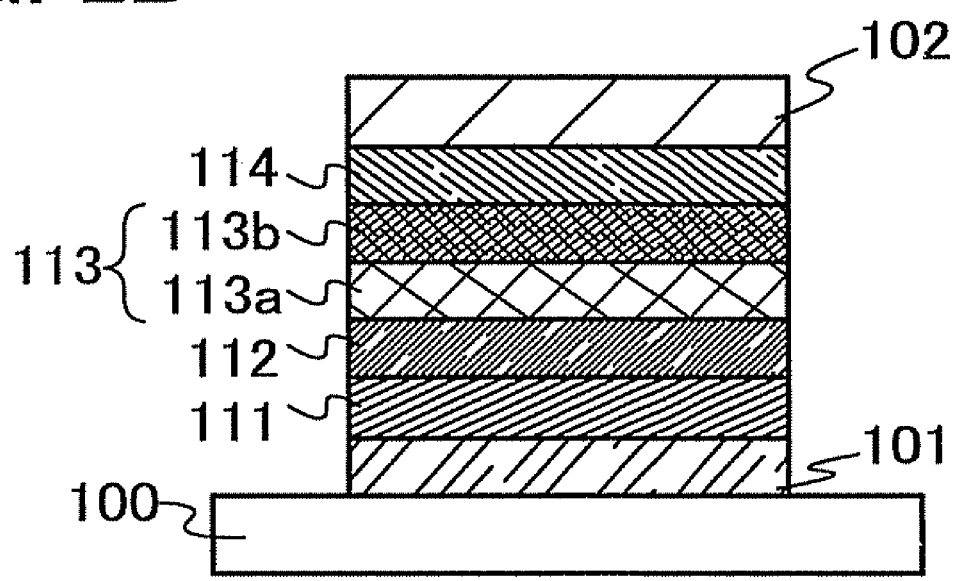

A structure is illustrated in FIG. 2A in which a layer 114a controlling transport of electron carriers is provided between the light-emitting layer 113 and an electron-transporting layer 114b. In the light-emitting layer 113, the carbazole derivative having the heteroaromatic ring of an embodiment of the present invention is used as a host material, and a light-emitting substance is dispersed therein. The layer 114a controlling transport of electron carriers is a layer in which a small amount of a substance having a high electron-trapping property is added to the material with a high electron-transporting property which forms the electron-transporting layer as exemplified in Embodiment 2. Alternatively, it is a layer in which a material having a low LUMO level and a hole-transporting property is added to a material having a high electron-transporting property. The layer 114a controlling transport of electron carriers is able to control transport of electron carriers, which allows the carrier balance to be readily adjusted. Such a structure is very effective in suppressing a problem (such as shortening of element lifetime) caused by a result that an electron passes through the light-emitting layer 113 to reach a layer which is adjacent to the anode side of the light-emitting layer 113.

As another structure, the light-emitting layer 113 may be formed of a plurality of layers. An example is shown in FIG. 2B in which the light-emitting layer 113 is structured using a first light-emitting layer 113a and a second light-emitting layer 113b.

For example, in the case where the light-emitting layer 113 is formed by stacking the first light-emitting layer 113a and the second light-emitting layer 113b in that order from the hole-transporting layer 112 side, the first light-emitting layer 113a may be formed using a substance with a hole-transporting property as the host material and the second light-emitting layer 113b may be formed using a substance with an electron-transporting property as the host material.

The carbazole derivative having the heteroaromatic ring of an embodiment of the present invention possesses both an oxadiazole moiety or a quinoxaline moiety as the heteroaromatic ring having an electron-transporting property and a carbazole moiety having a hole-transporting property. Thus, it is a bipolar material having a high ability to transport electrons and holes. Additionally, it has a wide energy gap. Therefore, the carbazole derivative having the heteroaromatic ring of an embodiment of the present invention can be used as the host material to disperse the light-emitting substance therein, as the light-emitting substance, and as the carrier-transporting material.

Note that selection of the layer to which the carbazole derivative having the heteroaromatic ring of an embodiment of the present invention is applied can be determined depending on the carrier-transporting property thereof. For example, in the case where it is applied to a light-emitting element with the structure illustrated in FIG. 2B, the carbazole derivative having the heteroaromatic ring whose hole-transporting property is superior to the electron-transporting property can be used for the first light-emitting layer 113a. The carbazole derivative having the heteroaromatic ring whose electron-transporting property is superior to the hole-transporting property can be used for the second light-emitting layer 113b.

This embodiment can be arbitrarily combined with other embodiments.

Embodiment 4

In this embodiment, an embodiment of a light-emitting element having a plurality of light-emitting layers is explained with reference to FIG. 3 as an example where the carbazole derivative having the heteroaromatic ring of an embodiment of the present invention is used. The light-emitting element of FIG. 3 has a plurality of light-emitting layers, and light, which is obtained by mixing light emitted from the plurality of light-emitting layers, is attainable. By mixing light emissions from different light-emitting layers, white light can be obtained for example.

Figure 3:
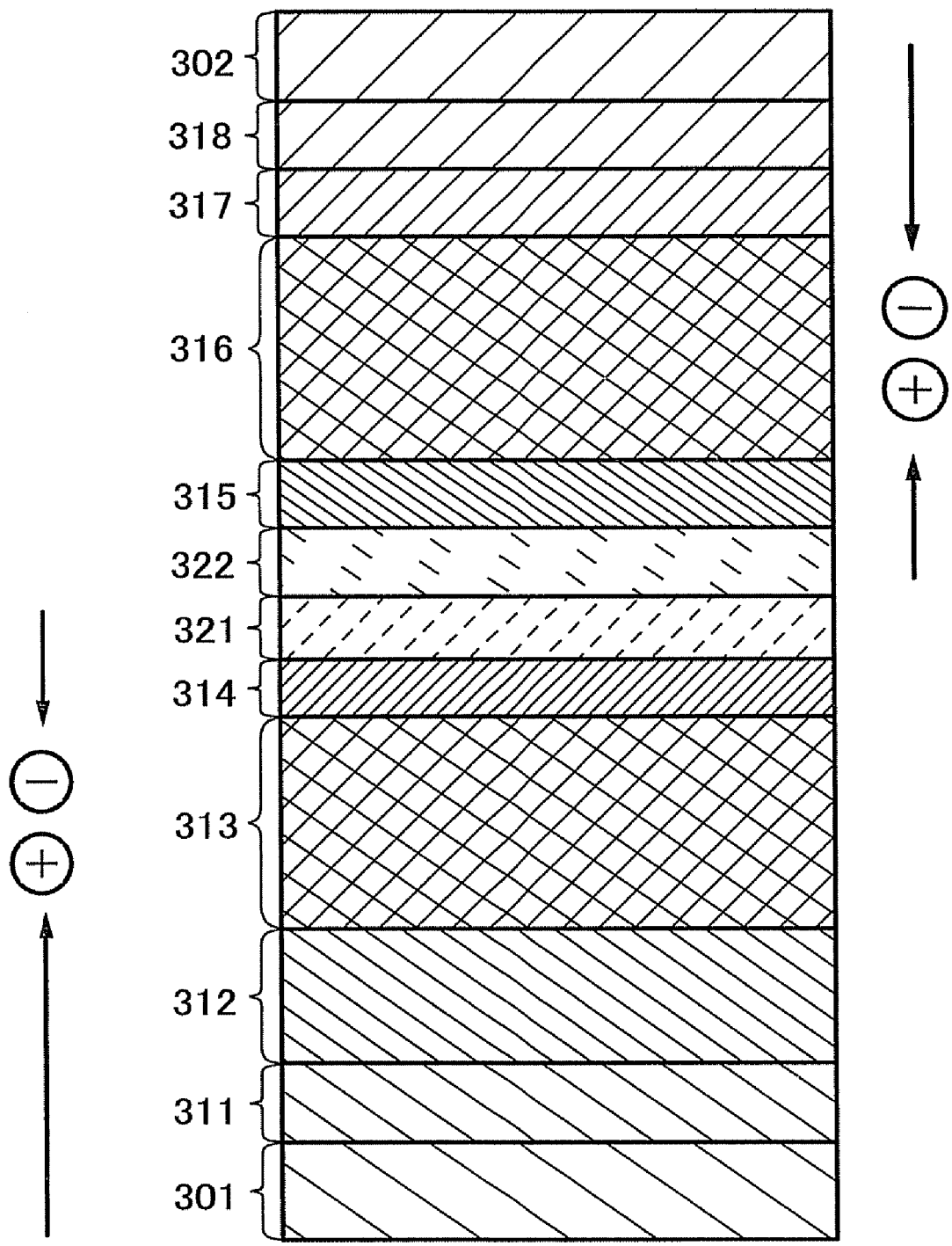
FIG. 3 illustrates a light-emitting element according to an embodiment of the present invention.

In the light-emitting element of FIG. 3, a first light-emitting layer 313 and a second light-emitting layer 316 are provided between a first electrode 301 and a second electrode 302. An N layer 321 and a P layer 322 are provided as a charge-generating layer between the first light-emitting layer 313 and the second light-emitting layer 316.

The N layer 321 generates electrons, and the P layer 322 generates holes. When voltage is applied such that the potential of the first electrode 301 is higher than that of the second electrode 302, holes injected from the first electrode 301 and electrons injected from the N layer 321 are recombined in the first light-emitting layer 313, and thus a first light-emitting substance included in the first light-emitting layer 313 emits light. In a similar manner, electrons injected from the second electrode 302 and holes injected from the P layer 322 are recombined in the second light-emitting layer 316, and thus a second light-emitting substance included in the second light-emitting layer 316 emits light.

A layer such as the light-emitting layer 113 described in the aforementioned Embodiment 2 can be applied to the first light-emitting layer 313 and the second light-emitting layer 316. For example, a layer can be used that is formed by using the carbazole derivative having the heteroaromatic ring of an embodiment of the present invention as the host material in which a light-emitting substance is dispersed.

Here, for the first light-emitting layer 313, a layer is used in which a fluorescent compound having an emission peak in a region from 450 nm to 510 nm (that is, blue to blue green region) is dispersed in the carbazole derivative having the heteroaromatic ring of an embodiment of the present invention. The carbazole derivative having the heteroaromatic ring of an embodiment of the present invention has a large energy gap, and can, therefore, be used as a host material of a blue emissive light-emitting substance.

On the other hand, for the second light-emitting layer 316, a layer is used in which a phosphorescent compound or a fluorescent compound capable of providing red light emission is dispersed in the carbazole derivative having the heteroaromatic ring of an embodiment of the present invention. The carbazole derivative having the heteroaromatic ring of an embodiment of the present invention has a large energy gap, and can, therefore, be used as a host material of a variety of blue to red emissive light-emitting substances.

Since the N layer 321 is a layer that generates electrons, it may be formed using the composite material formed by combining the organic compound and the electron donor which are described in aforementioned Embodiment 2. By adopting such a structure, electrons can be injected to the first light-emitting layer 313 side.

Since the P layer 322 is a layer that generates holes, it may be formed using the composite material formed by combining the organic compound and the electron acceptor which are described in aforementioned Embodiment 2. With such a structure, holes can be injected to the second light-emitting layer 316 side. Further, for the P layer 322, a metal oxide having an excellent hole-injecting property such as molybdenum oxide, vanadium oxide, ITO, or ITSO, can be used.

Although, as shown in FIG. 3, the light-emitting element including two light-emitting layers is described in the present embodiment, the number of the light-emitting layers is not limited to two but may be three, for example. In addition, light emission from each light-emitting layer may be mixed. As a result, white light emission can be obtained, for example.

The first electrode 301 may have a structure similar to that of the first electrode 101 described above in Embodiment 2. The second electrode 302 may also have a structure similar to the second electrode 102 described above in Embodiment 2.

In the present embodiment, as illustrated in FIG. 3, the hole-injecting layer 311, the hole-transporting layers 312 and 315, the electron-transporting layers 314 and 317, and the electron-injecting layer 318 are provided. The structures of the layers described above in Embodiments 2 and 3 may be applied to these layers. However, these layers are not necessarily provided and may be provided as appropriate depending on element characteristics.

Since the carbazole derivative having the heteroaromatic ring of an embodiment of the present invention exhibits an excellent electron-transporting property, the driving voltage of the light-emitting element can be reduced when it is used for the electron-transporting layer in contact with the light-emitting layer. In addition, it has a large energy gap; therefore, energy transfer from excitons in the light-emitting layer scarcely occurs, and thus decrease in luminous efficiency is negligible.

Further, since the carbazole derivative having the heteroaromatic ring of an embodiment of the present invention has a large energy gap, it can be used in the light-emitting layer as a host material of a blue emissive phosphorescent compound with an emission peak as short as 400 nm to 500 nm. As a result, like a stacked type light-emitting element of the present embodiment, only a phosphorescent compound that is superior to a fluorescent compound in terms of emission efficiency can be used as a light-emitting substance, which enables the production of a white emissive light-emitting element having excellent luminous efficiency.

Accordingly, with use of the light-emitting element in which the carbazole derivative having the heteroaromatic ring of an embodiment of the present invention is used, a light-emitting device with low power consumption can be realized.

Arrangement of a plurality of light-emitting units, which are partitioned by a charge generation layer between a pair of electrodes as in the light-emitting element of the present embodiment, makes it possible to provide high luminance at a low current density.

Note that the present embodiment can be freely combined with the other embodiments.

Embodiment 5

Figure 4A:
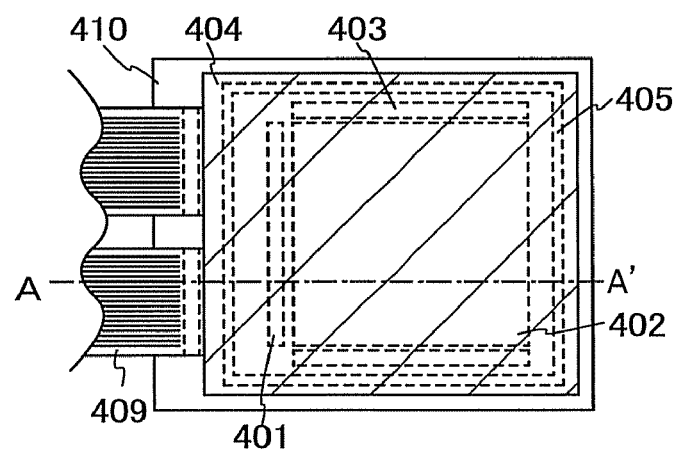
FIGS. 4A and 4B each illustrate a light-emitting device according to an embodiment of the present invention.
Figure 4B:
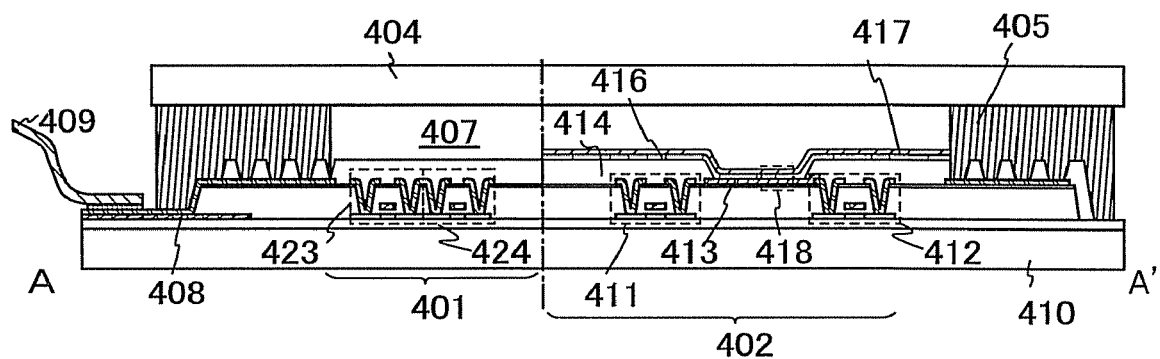

In the present embodiment, a light-emitting device manufactured using the carbazole derivative having the heteroaromatic ring of an embodiment of the present invention will be described with reference to FIGS. 4A, 4B, 5A, and 5B. Note that FIG. 4A is a top view illustrating the light-emitting device, and FIG. 4B is a sectional view taken along the section A-A' of FIG. 4A. A source side driver circuit is denoted by reference numerals 401, 402 and 403, which are shown by a dotted line; denote a driver circuit portion (a source side driver circuit), a pixel portion, and a driver circuit portion (a gate side driver circuit), respectively. Reference numeral 404 denotes a sealing substrate; reference numeral 405 denotes a sealant; and an inner side region enclosed by the sealant 405 is a space 407.

Note that a lead wiring 408 is a wiring for transmitting signals that are to be inputted to the source side driver circuit 401 and the gate side driver circuit 403, and receives a video signal, a clock signal, a start signal, a reset signal, and the like from a flexible printed circuit (FPC) 409 which serves as an external input terminal. Although only the FPCs are illustrated, printed wiring boards (PWBs) may be attached to the FPCs. The light-emitting device in the present specification includes, in its category, not only the light-emitting device itself but also the light-emitting device provided with the FPC or the PWB.

Next, a cross-sectional structure is described with reference to FIG. 4B. Although the driver circuit portions and the pixel portion 402 having a plurality of pixels are formed over a substrate 410, the source side driver circuit 401 which is the driver circuit portion and one of the plurality of pixels in the pixel portion 402 are illustrated here.

Note that as the source side driver circuit 401, a CMOS circuit which is obtained by combining an n-channel TFT 423 and a p-channel TFT 424 is formed. Further, the driver circuit may be formed using a variety of CMOS circuits, PMOS circuits, or NMOS circuits comprising TFTs. In this embodiment, a driver-integrated type in which a driver circuit is formed on a substrate is shown; however, it is not necessary to have such a structure, and the driver circuit can be formed not on the substrate but outside.

The pixel portion 402 includes a plurality of pixels having a switching TFT 411, a current control TFT 412, and a first electrode 413 electrically connected to a drain of the current control TFT 412. An insulator 414 is formed to cover an end portion of the first electrode 413. Here, the insulator 414 is formed using a positive type photosensitive acrylic resin film.

The insulator 414 is formed so as to have a curved surface having curvature at an upper end portion or a lower end portion thereof in order to obtain favorable coverage. For example, when positive type photosensitive acrylic is used as a material for the insulator 414, the insulator 414 preferably has a curved surface with a curvature radius (0.2 to 3 µm) only as the upper end. Alternatively, either a negative type resin which becomes insoluble in an etchant by light-irradiation or a positive type resin which becomes soluble in an etchant by light-irradiation can be used as the insulator 414.

Over the first electrode 413, a layer 416 including a light-emitting substance and a second electrode 417 are formed. Here, as a material for forming the first electrode 413 functioning as the anode, it is preferable to use a material having a high work function. For example, the first electrode 413 can be formed using a stack of a titanium nitride film and a film containing aluminum as its main component; a three-layer structure of a titanium nitride film, a film containing aluminum as its main component, and another titanium nitride film; or the like, as well as a single-layer film such as an indium tin oxide (ITO) film, an indium tin oxide film containing silicon, an indium zinc oxide (IZO) film, a titanium nitride film, a chromium film, a tungsten film, a Zn film, or a Pt film. The use of the multilayer structure results in a wiring with low electric resistance, enables a favorable ohmic contact, and further allows the electrode to function as an anode.

The layer 416 containing a light-emitting substance, which is interposed between the first electrode 413 and the second electrode 417, is formed in a manner similar to that in Embodiments 2 to 4, and the carbazole derivative having the heteroaromatic ring of an embodiment of the present invention described in Embodiment 1 is used for part of the layer 416. As a material which can be used by being combined with the carbazole derivative having the heteroaromatic ring of an embodiment of the present invention, a low molecular material, an oligomer, a dendrimer, or a high molecular material may be used. The layer 416 containing the light-emitting substance is formed as a single layer or a stacked layer of organic compounds in most cases. However, in the present invention, a structure may also be employed in which an organic compound film includes an inorganic compound.

The layer 416 containing a light-emitting substance is formed by a variety of methods such as an evaporation method using an evaporation mask, an ink-jet method, and a spin coating method.

As a material used for the second electrode 417 which is to be formed over the layer 416 including a light-emitting substance, a material having a low work function (e.g., Al, Ag, Li, Ca, or an alloy or a compound of them, such as MgAg, MgIn, AlLi, LiF, $CaF_2$, calcium nitride, or calcium fluoride) is preferably used. Note that, in the case where light emitted from the layer 416 including a light-emitting substance is transmitted through the second electrode 417 which serves as a cathode, a stack of a metal thin film with reduced film thickness and a transparent conductive film (indium tin oxide (ITO), indium oxide-zinc oxide alloy ($In_2O_3$—ZnO), zinc oxide (ZnO), or the like) is preferably used as the second electrode 417.

Attachment of the sealing substrate 404 to the substrate 410 with the sealant 405 makes a structure in which a light-emitting element 418 is provided in the space 407 surrounded by the substrate 410, the sealing substrate 404, and the sealant 405. Note that the space 407 may be filled with an inert gas (e.g., nitrogen or argon) or with the sealant 405.

Note that as the sealant 405, an epoxy-based resin is preferably used. A material used for the sealant 405 is preferably a material which does not transmit moisture or oxygen as much as possible. As the sealing substrate 404, a plastic substrate made of fiberglass-reinforced plastics (FRP), polyvinyl fluoride (PVF), polyester, an acrylic resin, or the like can be used besides a glass substrate or a quartz substrate.

As described above, a light-emitting device fabricated using the carbazole derivative having the heteroaromatic ring of an embodiment of the present invention can be obtained.

Since the carbazole derivative having the heteroaromatic ring described in Embodiment 1 is used for the light-emitting device of an embodiment of the present invention, a high-performance light-emitting device can be obtained. Specifically, a light-emitting device that consumes lower power and can be driven for a long time can be obtained since the light-emitting device possesses the light-emitting element with high luminous efficiency.

Figure 5A:
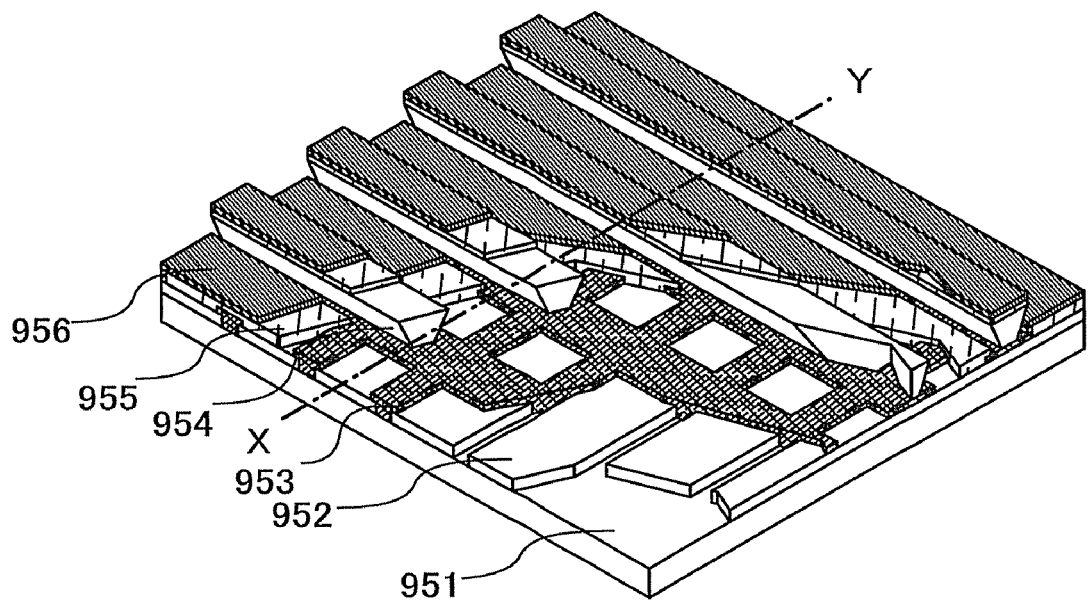
FIGS. 5A and 5B each illustrate a light-emitting device according to an embodiment of the present invention.
Figure 5B:
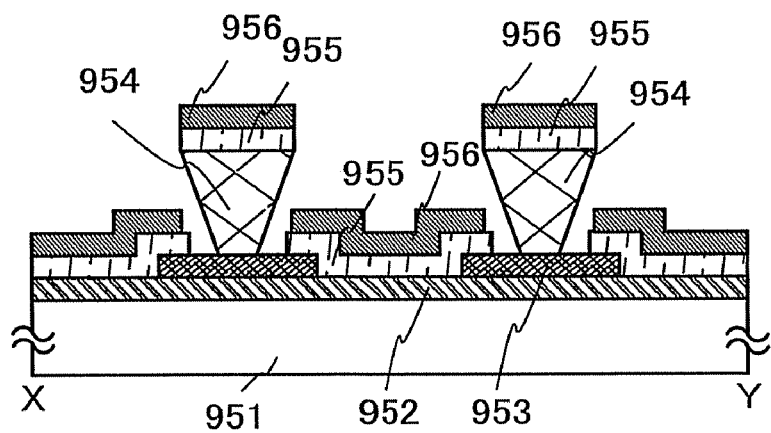

Although an active matrix light-emitting device which controls driving of a light-emitting element with a transistor is described above, the light-emitting device may be a passive matrix light-emitting device. FIGS. 5A and 5B illustrate a passive matrix image display device fabricated according to the present invention. Note that FIG. 5A is a perspective view illustrating the passive matrix image display device and FIG. 5B is a cross sectional view of FIG. 5A taken along a line X-Y. In FIGS. 5A and 5B, an electrode 952 and an electrode 956 are provided over a substrate 951, and a layer 955 including a light-emitting substance is provided between the electrodes 952 and 956. An edge portion of the electrode 952 is covered with an insulating layer 953. A partition layer 954 is provided over the insulating layer 953.

The sidewalls of the partition layer 954 are aslope such that the distance between both sidewalls is gradually narrowed toward the surface of the substrate. That is, a cross section in a short side of the partition layer 954 is a trapezoidal shape, and a lower side (the side is in contact with the insulating layer 953) is shorter than an upper side (the side is not in contact with the insulating layer 953). By providing the partition layer 954 in this manner, defects of the light-emitting element due to the crosstalk and the like can be prevented.

The layer 955 containing a light-emitting substance which is interposed between the electrode 952 and the electrode 956 is formed in a manner similar to that in Embodiments 2 to 4, and the carbazole derivative having the heteroaromatic ring of an embodiment of the present invention which is described in Embodiment 1 is used for part of the layer 955.

Since the carbazole derivative having the heteroaromatic ring described in Embodiment 1 is used for the light-emitting device of an embodiment of the present invention, a high-performance light-emitting device can be obtained. Specifically, a light-emitting device that has reduced power consumption and can be driven for a long time can be obtained since the light-emitting device possesses the light-emitting element with high luminous efficiency.

Embodiment 6

In this embodiment, electronic devices according to the present invention, each of which includes the light-emitting device described in Embodiment 5, are described. The electronic device of an embodiment of the present invention includes the carbazole derivative having the heteroaromatic ring described in Embodiment 1, and thus includes a display portion having high luminous efficiency, low power consumption, and capability of long-time driving. In addition, the electronic device of an embodiment of the present invention includes a display portion having excellent color reproducibility.

As examples of the electronic devices each of which includes a light-emitting element manufactured using the carbazole derivative having the heteroaromatic ring of an embodiment of the present invention, the following are given: cameras such as video cameras or digital cameras; goggle type displays, navigation systems, audio reproducing devices (e.g., car audio components and audio components), computers, game machines, portable information terminals (e.g., mobile computers, cellular phones, portable game machines, and electronic books), and image reproducing devices provided with recording media (specifically, a device capable of reproducing recording media such as digital versatile discs (DVDs) and provided with a display device that can display the image). Specific examples of these electronic devices are shown in FIGS. 6A to 6D.

Figure 6A:
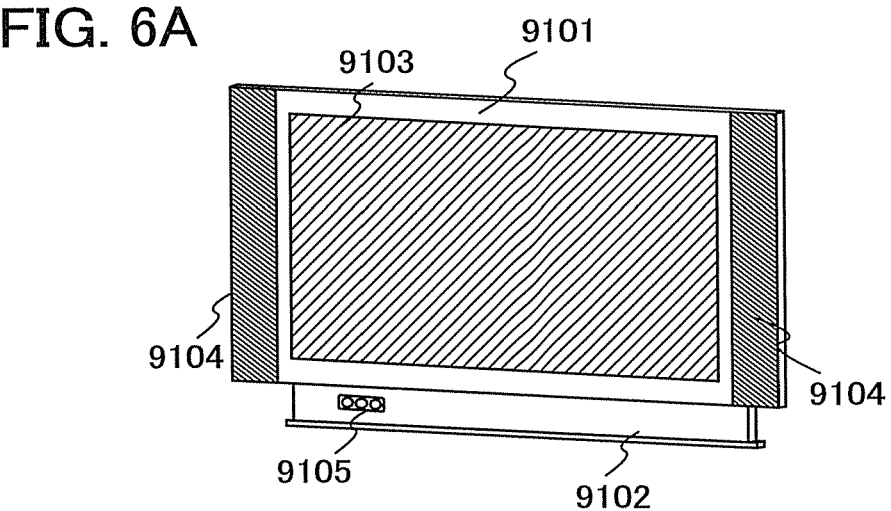
FIGS. 6A to 6D each illustrate an electronic device according to an embodiment of the present invention.

FIG. 6A illustrates a television device according to the present invention, which includes a housing 9101, a support 9102, a display portion 9103, a speaker portion 9104, a video input terminal 9105, and the like. In the display portion 9103 of this television device, light-emitting elements similar to those described in Embodiments 2 to 4 are arranged in a matrix. The light-emitting elements are characterized in high luminous efficiency. The display portion 9103 including the light-emitting elements has similar features, which allows the television device to exhibit light emission with high luminance and consume smaller amount of power. Since the television device according to the present invention consumes reduced amount of power and has improved image quality, a product that is suitable for any residential environment can be provided.

Figure 6B:
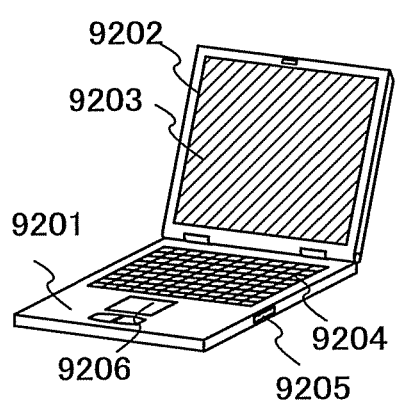

FIG. 6B shows a computer according to the present invention, which includes a main body 9201, a housing 9202, a display portion 9203, a keyboard 9204, an external connection port 9205, a pointing device 9206, and the like. In the display portion 9203 of this computer, light-emitting elements similar to those described in Embodiments 2 to 4 are arranged in a matrix. The light-emitting elements are characterized in high luminous efficiency. The display portion 9203 including the light-emitting elements has similar features, which allows the display portion 9203 to exhibit light emission with high luminance and consume smaller amount of power. Since the computer according to the present invention consumes reduced amount of power and has improved image quality, a product that is suitable for any residential environment can be provided.

Figure 6C:
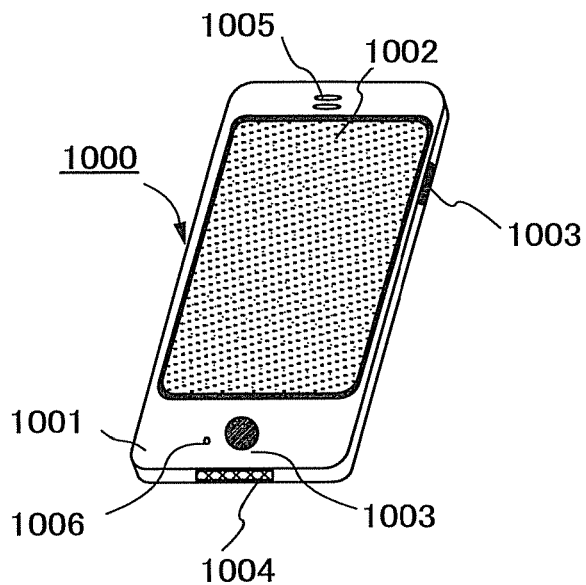

FIG. 6C illustrates a cellular phone 1000 according to the present invention, and a display portion 1002, an operation button 1003, an external connection port 1004, a speaker 1005, a microphone 1006, and the like are incorporated in a housing 1001. Information can be inputted when the display portion 1002 is touched with a finger or the like. In addition, operations such as making calls and composing mails can be also conducted by touching the display portion 1002 with a finger or the like. In the display portion 1002 of this cellular phone, the light-emitting elements similar to those described in Embodiments 2 to 4 are arranged in a matrix. The light-emitting elements are characterized in high luminous efficiency. The display portion 1002 including the light-emitting elements has similar features, which allows the display portion 1002 to exhibit light emission with high luminance and consume smaller amount of power. Since the cellular phone according to the present invention consumes reduced amount of power and has improved image quality, a product that is suitable for any residential environment can be provided.

Figure 6D:
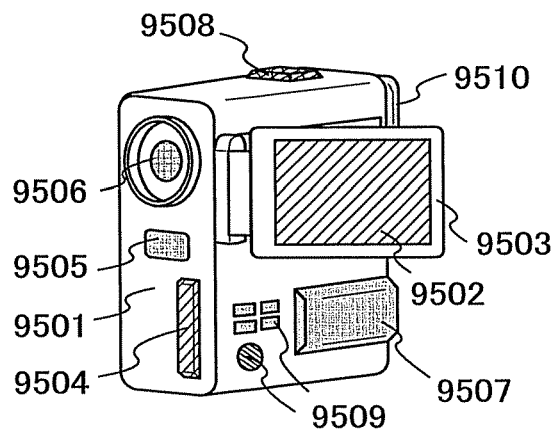

FIG. 6D shows a camera according to the present invention, which includes a main body 9501, a display portion 9502, a housing 9503, an external connection port 9504, a remote control receiving portion 9505, an image receiving portion 9506, a battery 9507, an audio input portion 9508, an operation key 9509, an eyepiece portion 9510, and the like. In the display portion 9502 of this computer, light-emitting elements similar to those described in Embodiments 2 to 4 are arranged in a matrix. The light-emitting elements have the advantage that the luminous efficiency is high and long-time driving is possible. The display portion 9502 including the light-emitting elements has similar features, which allows the display portion 9502 to exhibit light emission with high luminance and consume smaller amount of power. Since the camera according to the present invention consumes reduced amount of power and has improved image quality, a product that is suitable for any residential environment can be provided.

As thus described, application range of the light-emitting device of the present invention is quite wide, and this light-emitting device can be applied to electronic devices of every field. Use of the carbazole derivative having the heteroaromatic ring of an embodiment of the present invention enables the production of the electronic devices each including a display portion having high emission efficiency, capability of long-time driving, and low power consumption to be provided.

Moreover, the light-emitting device of an embodiment of the present invention can be used as a lighting device. An example of using the light-emitting element of an embodiment of the present invention as a lighting device will be described with reference to FIG. 7.

Figure 7:
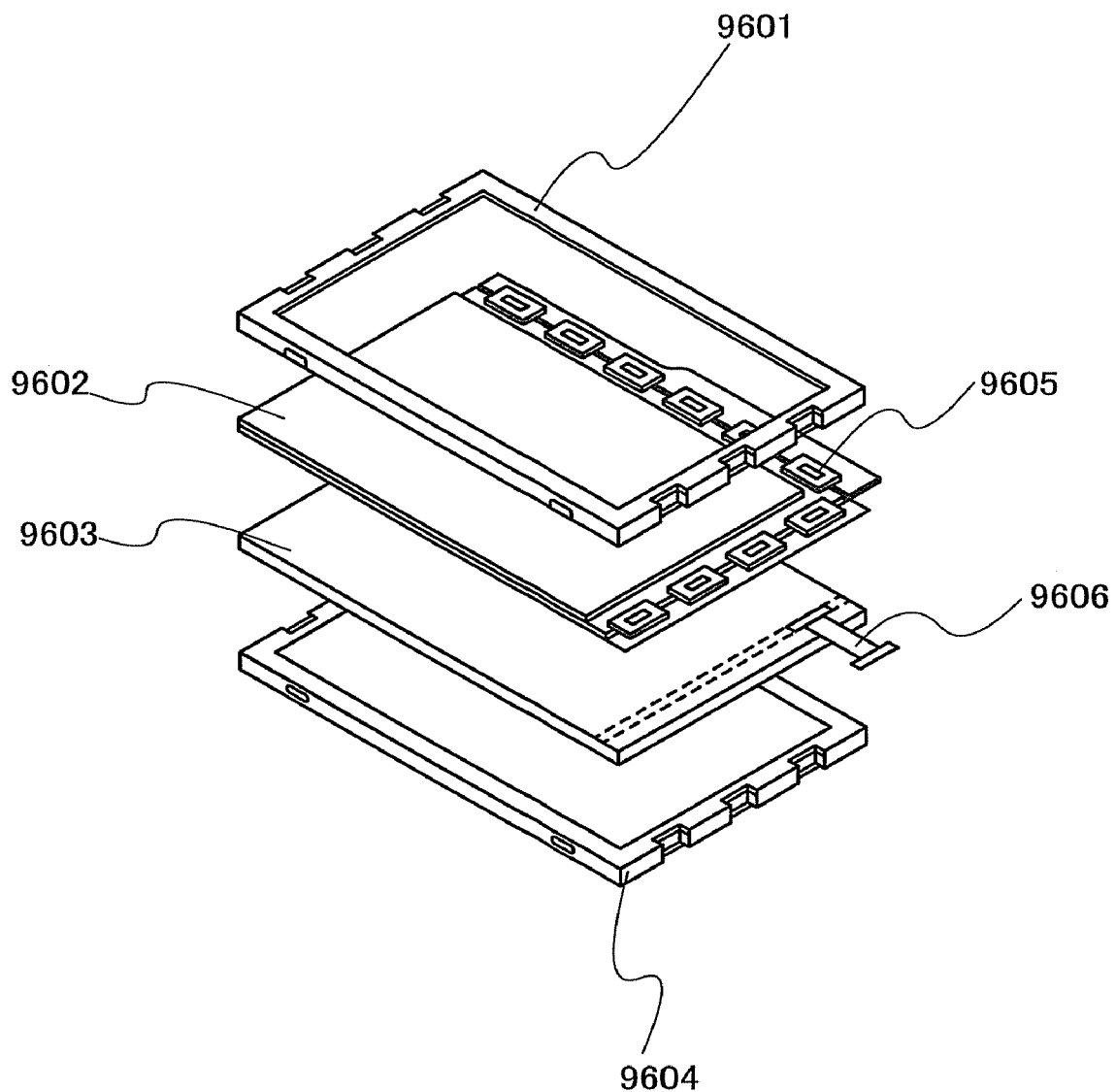
FIG. 7 illustrates an electronic device according to an embodiment of the present invention.

FIG. 7 shows an example of a liquid crystal display device in which the light-emitting device of according to the present invention is used as a backlight. The liquid crystal display device illustrated in FIG. 7 includes a chassis 9601, a liquid crystal layer 9602, a backlight 9603, and a chassis 9604, and the liquid crystal layer 9602 is connected to a driver IC 9605. The light-emitting device of according to the present invention is used as the backlight 9603, and current is supplied through a terminal 9606.

By using the light-emitting device of an embodiment of the present invention as the backlight of the liquid crystal display device, a liquid crystal display device with reduced power consumption can be obtained. Moreover, since the light-emitting device of an embodiment of the present invention is an illumination device of surface light emission and the enlargement of the light-emitting device is possible, the backlight can be made larger and the liquid crystal display device can also have a larger area. Additionally, since the light-emitting device of an embodiment of the present invention is thin, reduction in thickness of the liquid crystal display device is possible. Further, since the light-emitting device of an embodiment of the present invention can exhibit light emission with high luminance, the liquid crystal display device using the light-emitting device of an embodiment of the present invention can also exhibit light emission with high luminance.

Figure 8:
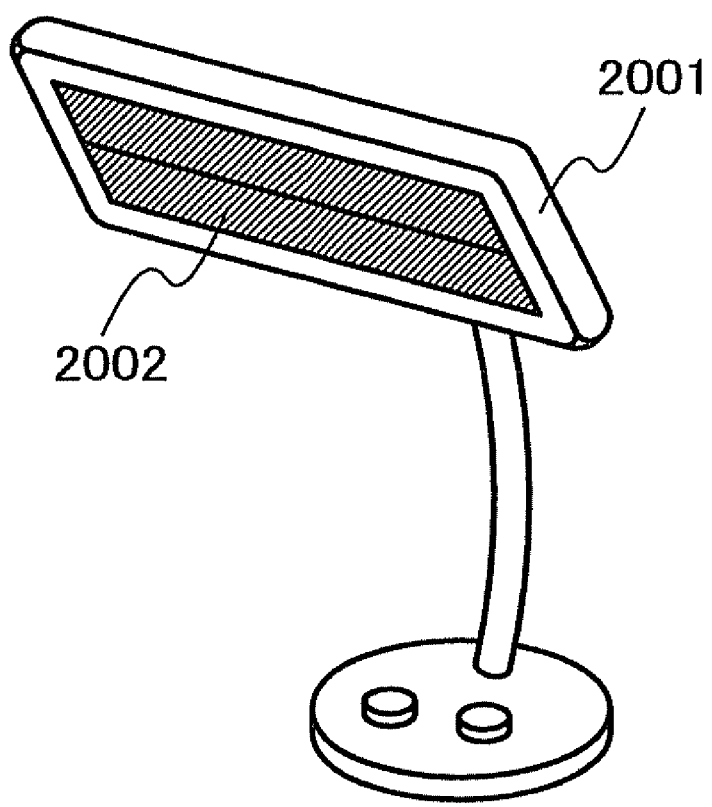
FIG. 8 illustrates a lighting device according to an embodiment of the present invention.

FIG. 8 illustrates an example in which the light-emitting device according to the present invention is used as a desk lamp, which is an illumination device. The desk lamp illustrated in FIG. 8 includes a housing 2001 and a light source 2002. The light-emitting device of an embodiment of the present invention is used as the light source 2002. Since the light-emitting device of an embodiment of the present invention has high luminous efficiency, can be driven for a long time, and has reduced power consumption, the table lamp also has high luminous efficiency, can be driven for a long time, and has reduced power consumption.

Figure 9:
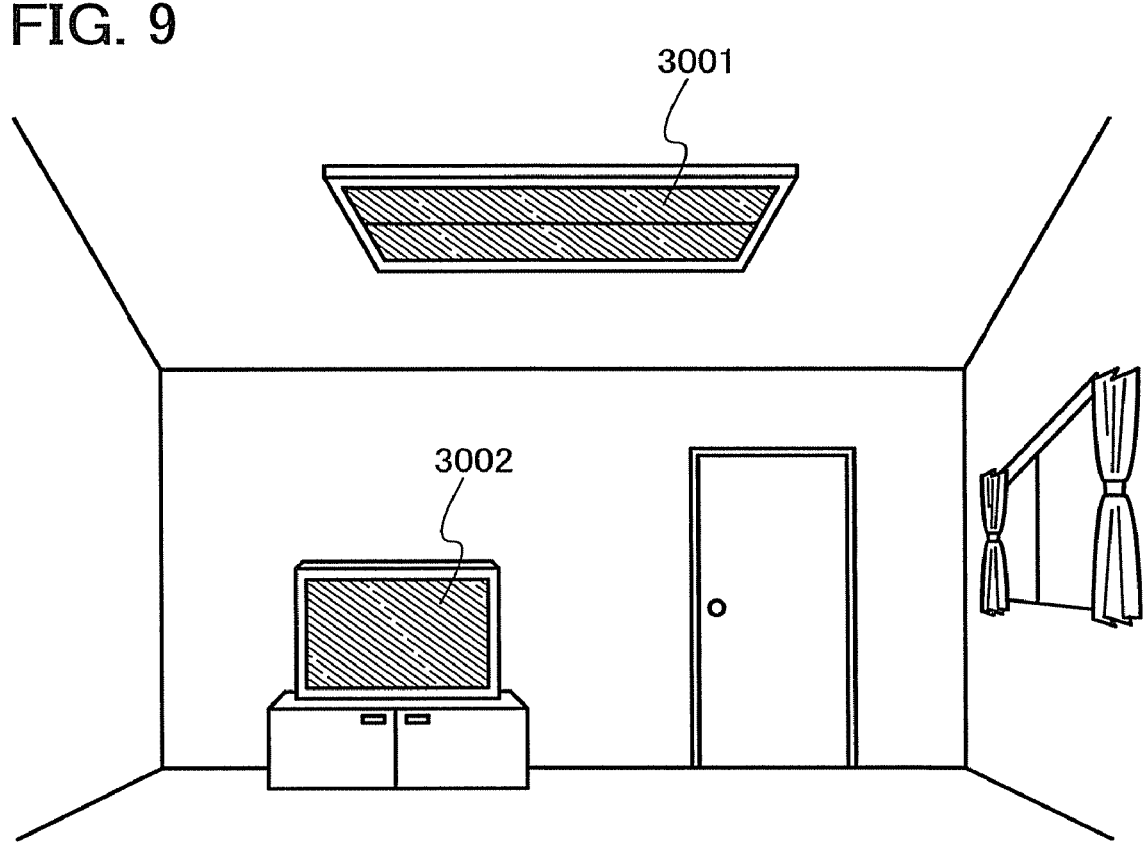
FIG. 9 illustrates a lighting device according to an embodiment of the present invention.

FIG. 9 illustrates an example of using the light-emitting device according to the present invention as an interior illumination device 3001.

Since the light-emitting device of an embodiment of the present invention can be enlarged, the light-emitting device can be used as a large-area illumination device. Further, since the light-emitting device of an embodiment of the present invention has a thin shape and reduced power consumption, it can be used as a lighting device having a thin shape and consuming low power. Accordingly, a television device 3002 according to the present invention explained in FIG. 6A is placed in a room where the light-emitting device to which the present invention is applied is used as the interior lighting device 3001 so that public broadcasting and movies can be watched. In such a case, since both of the devices have reduced power consumption, a powerful image can be watched in a bright room without concern about electricity charges.

Example 1

Synthesis Example 1

In the present example, a synthetic method of 4-(9-phenyl-9H-carbazol-3-yl)-4'-(3-phenylqunoxalin-2-yl)triphenylamine (abbreviation: PCBA1PQ) which is the carbazole derivative having the heteroaromatic ring and represented by the structural formula (1) of Embodiment 1 is explained.

(1)

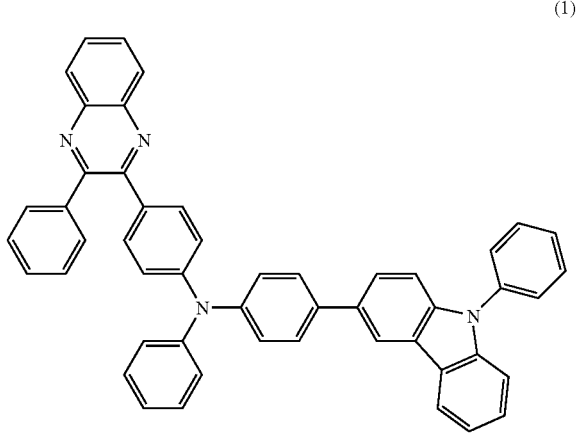

A scheme for the preparation of 4-(9-phenyl-9H-carbazol-3-yl)-4'-(3-phenylquinoxalin-2-yl)triphenylamine is shown in (M2).

(M2)

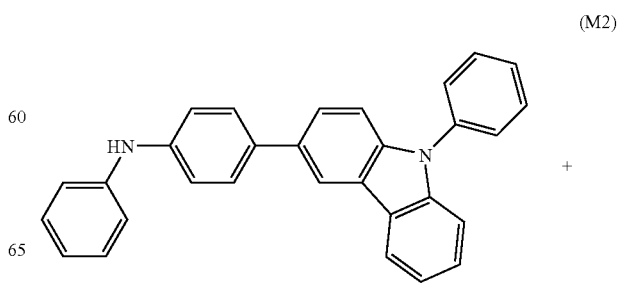

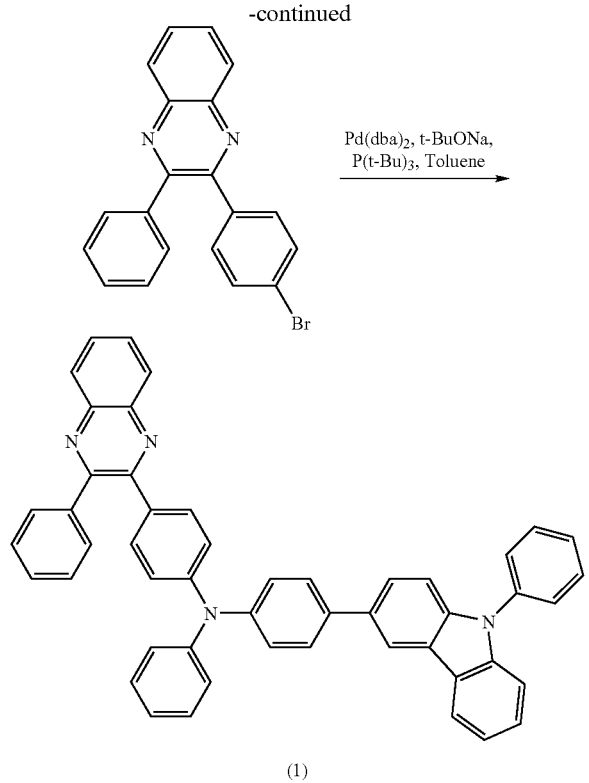

(1)

Into a 100 mL three-neck flask were added 1.7 g (4.2 mmol) of 4-(9-phenyl-9H-carbazol-3-yl)diphenylamine, 1.5 g (4.2 mmol) of 2-(4-bromobiphenyl)-3-phenylqunoxaline, and 1.0 g (10 mmol) of sodium tert-butoxide, and the atmosphere in the flask was substituted with nitrogen. After 15 mL of toluene and 0.10 mL of tri(tert-butyl)phosphine (a 10 wt % hexane solution) were added to the mixture, degassing was carried out with stirring under a reduced pressure, and the atmosphere in the flask was substituted with nitrogen. To the mixture was added 0.020 g (0.035 mmol) of bis(dibenzylideneacetone)palladium(0), which was followed by stirring at 80° C. for 5 hours.

After the reaction, toluene was added to this mixture, and the obtained suspension was subjected to suction filtration through Celite (manufactured by Wako Pure Chemical Industries, Ltd., Catalog No. 531-16855), alumina, and Florisil (manufactured by Wako Pure Chemical Industries, Ltd., Catalog No. 540-00135). The obtained filtrate was washed with a saturated aqueous solution of sodium carbonate and then with brine. The organic layer was dried with magnesium sulfate, and the mixture was suction-filtrated to remove the magnesium sulfate. The resulting filtrate was concentrated, and the obtained residue was purified by silica gel column chromatography.

As the developing solvents in the column chromatography, a mixed solvent of toluene:hexane=1:1 was used first, then toluene was next used, and a mixed solvent of toluene:ethyl acetate=5:1 was used in that order. The fractions obtained were concentrated, and the resulting solid was recrystallized with a mixed solvent of dichloromethane and methanol to give 2.7 g of a yellow powdered solid in 92% yield.

Next, 1.6 g of the obtained yellow solid was purified by train sublimation. The sublimation purification was performed at 310° C. for 18 hours under a reduced pressure of 7 Pa and a flow rate of argon of 3 mL/min. The yield was 1.2 g (75%).

Figure 10A:
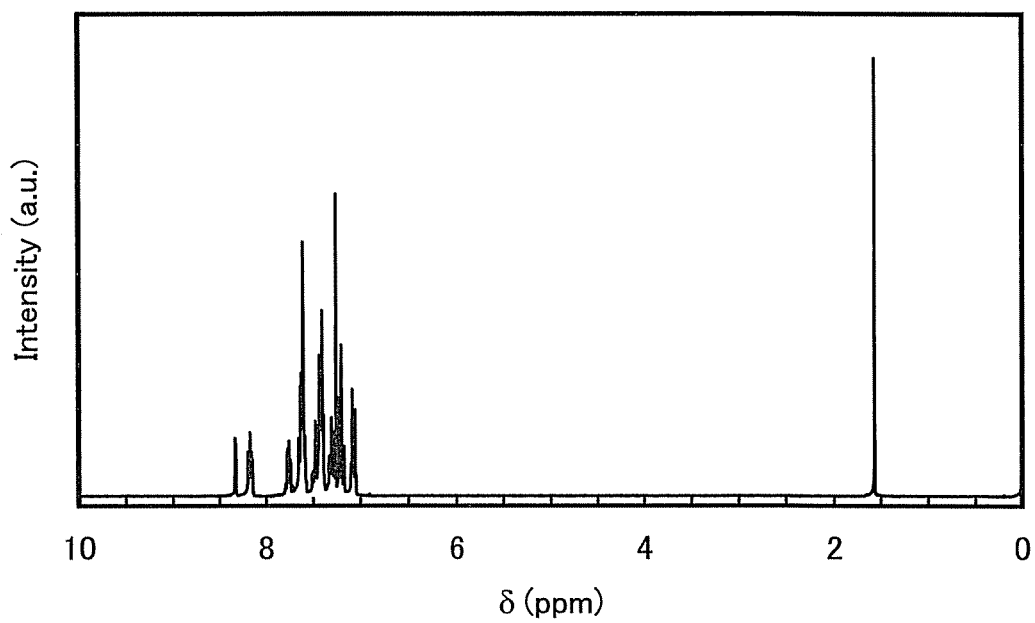
FIGS. 10A and 10B each are a $^1$H NMR chart of PCBA1PQ.
Figure 10B:
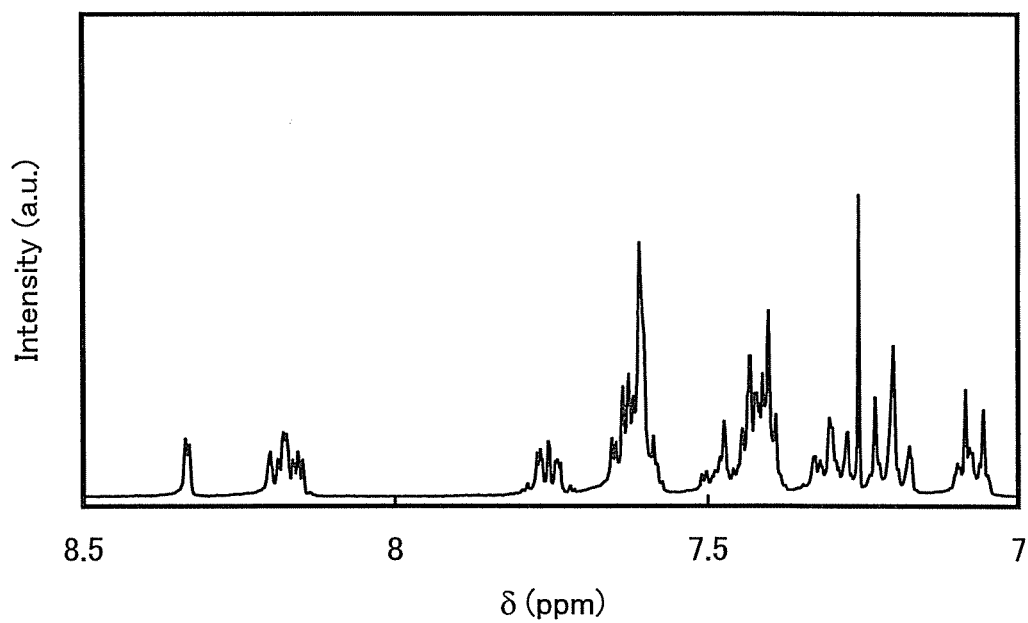

The result of an analysis of thus obtained powder by nuclear magnetic resonance spectrometry ($^1$H-NMR) is shown below. $^1$H-NMR charts are shown in FIGS. 10A and 10B. Note that FIG. 10B is a chart magnifying the range of 7.0 to 8.5 ppm in FIG. 10A.

$^1$H NMR (CDCl$_3$, 300 MHz): δ 7.04-7.10 (m, 3H), 7.17-7.79 (m, 27H), 8.14-8.20 (m, 3H), 8.33 (s, 1H).

From the result of the $^1$H NMR analysis, the compound obtained in this synthesis example was confirmed to be 4-(9-phenyl-9H-carbazol-3-yl)-4'-(3-phenylqunoxalin-2-yl)triphenylamine (abbreviation: PCBA1PQ) which is an embodiment of the present invention and is represented by the structural formula (1).

Next, the ultraviolet-visible absorption spectrum and the emission spectrum of PCBA1PQ were measured. A toluene solution including PCBA1PQ in a quartz cell and a thin film of PCBA1PQ fabricated by vacuum evaporation onto a quartz substrate were used as samples. The absorption spectrum was measured with an ultraviolet-visible spectrophotometer (V-550, manufactured by JASCO Corporation). The emission spectrum was measured using a fluorescence spectrophotometer (FS920, manufactured by Hamamatsu Photonics Corporation).

Figure 11A:
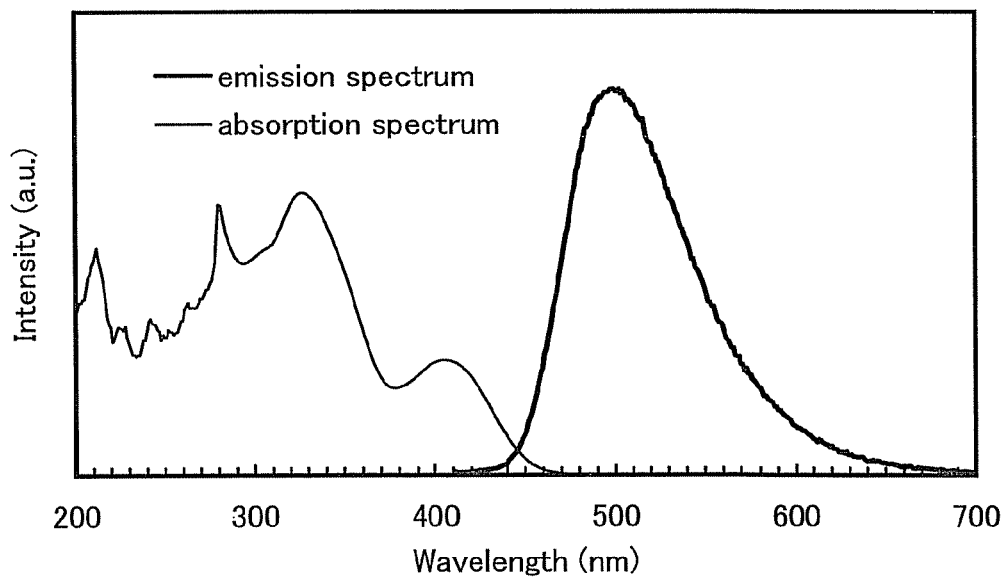
FIGS. 11A and 11B each illustrate UV-vis. absorption spectra and emission spectra of a toluene solution and a thin film of PCBA1PQ, respectively.
Figure 11B:
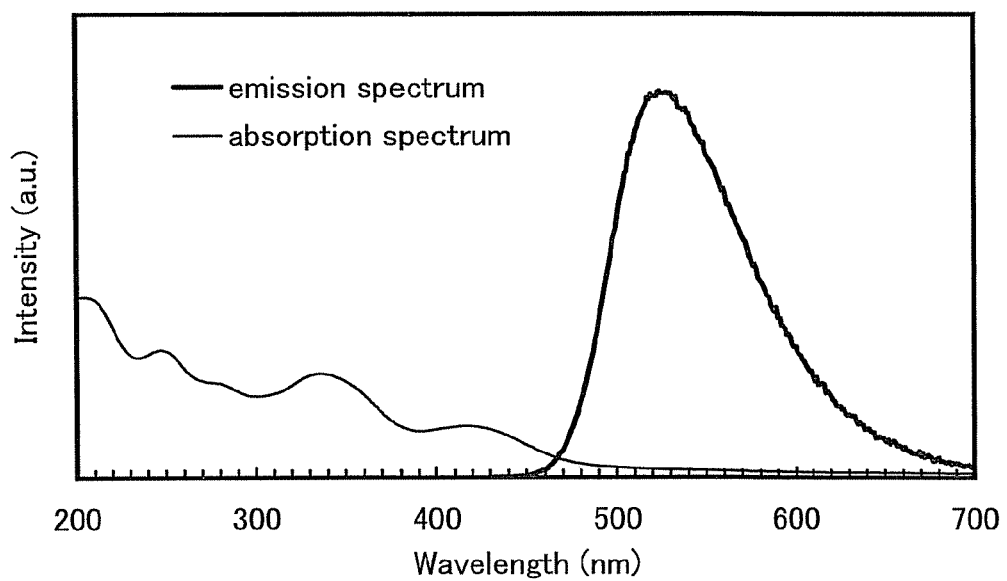

FIGS. 11A and 11B show the measurement results of the toluene solution and the thin film of PCBA1PQ, respectively. The horizontal axis represents wavelength (nm) and the vertical axis represents arbitrary intensity of absorbance and emission intensity. As for the absorption spectrum of the solution sample, the result obtained by subtraction of the absorption spectrum of the quartz cell including only toluene is shown. In the case of the thin film sample, the result obtained by subtraction of the absorption spectrum of the quartz substrate is shown.

The peak wavelength of the absorption spectrum of the toluene solution of PCBA1PQ was 403 nm, and the peak wavelength of the fluorescent spectrum was 500 nm (excitation wavelength: 403 nm). The peak wavelength of the absorption spectrum of the thin film of PCBA1PQ was 417 nm, and the peak wavelength of the fluorescent spectrum was 527 nm (excitation wavelength: 410 nm).

The HOMO level and LUMO level of PCBA1PQ in the state of a thin film were estimated. The value of the HOMO level was obtained by converting the value of the ionization potential obtained with a photoelectron spectrometer (AC-2, manufactured by Riken Keiki Co., Ltd.) into a negative value. The value of the LUMO level was obtained in such a manner that the absorption edge, whish is obtained from Tauc plot with an assumption of direct transition using data on the absorption spectrum of the thin film of PCBA1PQ, is regarded as an optical energy gap and is added to the value of the HOMO level. As a result, the HOMO level, the energy gap, and the LUMO level of PCBA1PQ were −5.42 eV, 2.66 eV, and −2.76 eV, respectively. Thus, it was proven that PCBA1PQ is an organic substance having a band gap greater than 0.2 eV.

The oxidation-reduction reaction characteristics of PCBA1PQ were evaluated. The oxidation-reduction characteristics were evaluated by cyclic voltammetry (CV) measurement. An electrochemical analyzer (ALS model 600A, manufactured by BAS Inc.) was used for the measurement.

As for a solution used for the CV measurement, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was dissolved in the solution such that the concentration thereof was 1 mmol/L. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. The measurement was carried out at room temperature.

The oxidation characteristic of PCBA1PQ was evaluated as follows. A scan for changing the potential of the working electrode with respect to the reference electrode from 0.28 V to 0.65 V and then from 0.65 V to 0.28 V was regarded as one cycle, and the measurement was performed for 100 cycles. The scanning speed of the CV measurement was 0.1 V/s.

The reduction characteristics of PCBA1PQ were evaluated as follows. A scan for changing the potential of the working electrode with respect to the reference electrode from −1.40 V to −2.24 V and then from −2.24 V to −1.40 V was regarded as one cycle, and the measurement was performed for 100 cycles. The scanning speed of the CV measurement was adjusted at 0.1 V/s.

Figure 12A:
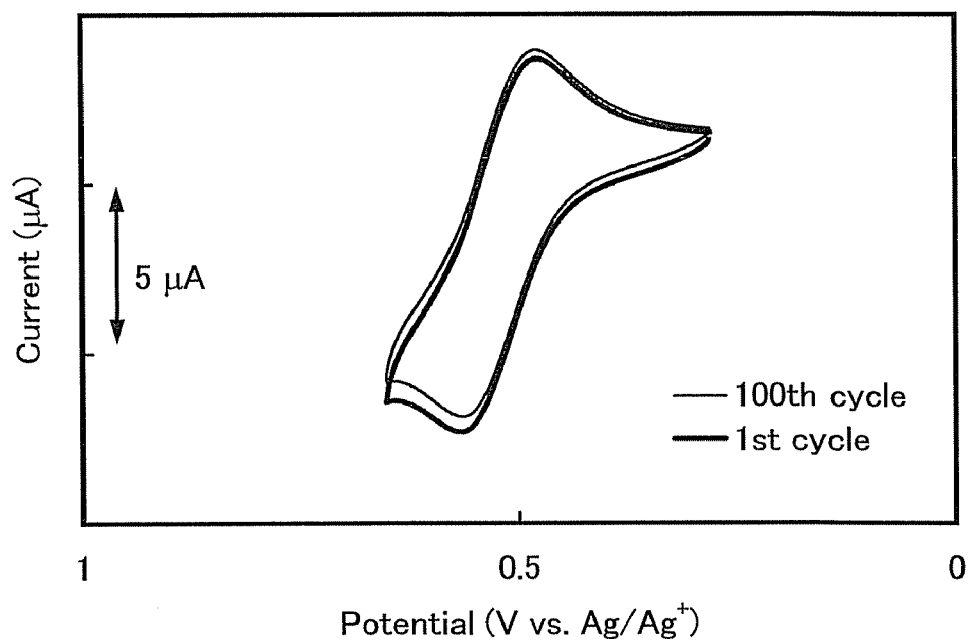
FIGS. 12A and 12B each illustrate a result of CV measurement of PCBA1PQ.
Figure 12B:
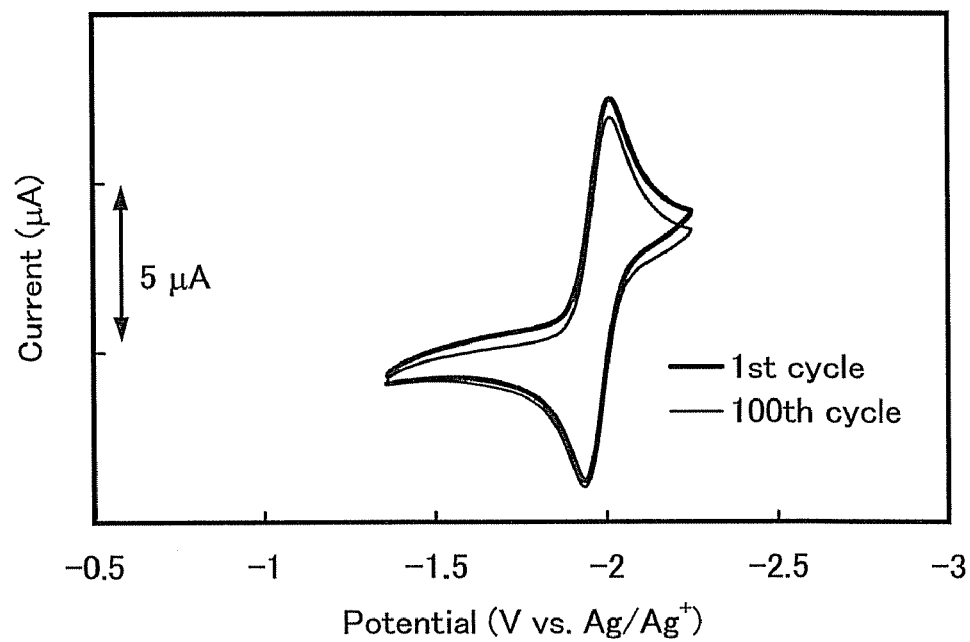

FIGS. 12A and 12B show CV measurement results on the oxidation side and the reduction side of PCBA1PQ, respectively. In FIGS. 12A and 12B, the horizontal axis shows potential (V) of the work electrode with respect to the reference electrode, and the vertical axis shows a value (μA) of current flowing between the work electrode and the auxiliary electrode. In FIG. 12A, a current indicating oxidation is observed at around +0.52 V (vs. Ag/Ag$^+$). In FIG. 12B, a current indicating reduction is observed at around −1.98 V (vs. Ag/Ag$^+$).

Although the scan was performed as many as 100 cycles, no significant change in the peak position and peak intensity of the CV curves was observed in both the oxidation and the reduction, which proves that the carbazole derivative having the heteroaromatic ring according to the present invention is stable when oxidation and reduction are repeatedly performed.

The molecular structure of PCBA1PQ in the ground state was optimized using the density functional theory (DFT). In the DFT, the total energy is represented as the sum of potential energy, electrostatic energy between electrons, kinetic energy of electrons, and exchange-correlation energy including all the complicated interactions between electrons. Since, in the DFT, an exchange-correlation interaction is approximated by a functional (a function of another function) of one electron potential represented in terms of electron density, the calculations are very rapid and highly accurate. Here, B3LYP which was a hybrid functional was used to specify the weight of each parameter related to exchange-correlation energy. In addition, as a basis function, 6-311 (a basis function of a triple-split valence basis set using three contraction functions for each valence orbital) was applied to all the atoms. By the above basis function, for example, orbits of 1s to 3s are considered in the case of hydrogen atoms while orbits of 1s to 4s and 2p to 4p are considered in the case of carbon atoms. Furthermore, to improve calculation accuracy, the p function and the d function as polarization basis sets were added respectively to hydrogen atoms and atoms other than hydrogen atoms.

Note that Gaussian 03 was used as a quantum chemistry computational program. The calculation was performed using a high performance computer (Altix3700 DX, manufactured by SGI).

Figure 27A:
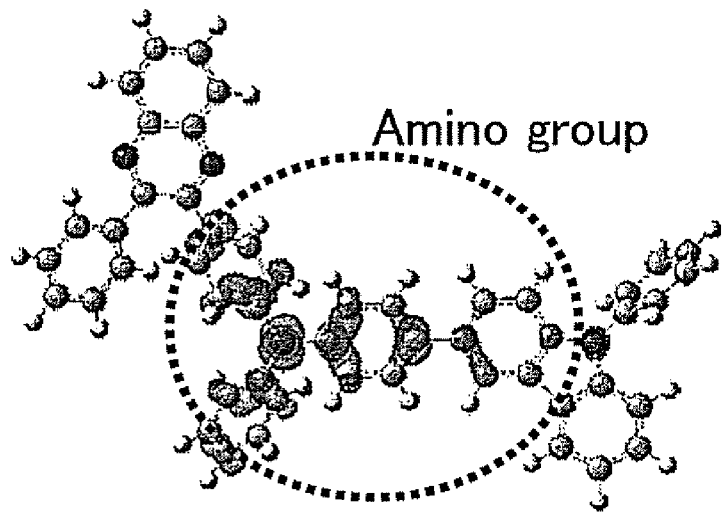
FIGS. 27A and 27B illustrate the highest occupied molecular orbital (HOMO) and the lowest unoccupied molecular orbital (LUMO) of an optimal molecular structure of PCBA1PQ, respectively.
Figure 27B:
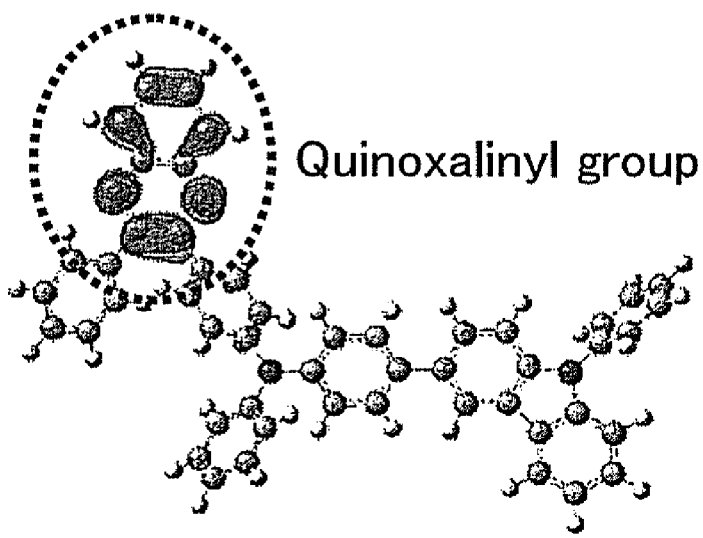

The highest occupied molecular orbital (HOMO) and the lowest unoccupied molecular orbital (LUMO) of the optimal molecular structure of PCBA1PQ obtained by the calculation are visualized using Gauss View 4.1 and shown in FIGS. 27A and 27B. FIG. 27A shows the highest occupied molecular orbital (HOMO), and FIG. 27B shows the lowest unoccupied molecular orbital (LUMO). The spheres in FIGS. 27A and 27B represent atoms which form PCBA1PQ, and cloud-like objects located around atoms represent the highest occupied molecular orbital (HOMO) or the lowest unoccupied molecular orbital (LUMO).

From FIGS. 27A and 27B, it is revealed that the highest occupied molecular orbital is localized around the amino group, which indicates that the amino group significantly contributes to the hole-transporting property of PCBA1PQ. Moreover, the lowest unoccupied molecular orbital is localized around the quinoxaline group, which proves that the quinoxalinyl group significantly contributes to the electron-transporting property of PCBA1PQ. Therefore, it can be understood that a bipolar material can be realized because both the quinoxaline moiety having a heteroaromatic ring with an electron-transporting property and the carbazole moiety having a hole-transporting property are incorporated to PCBA1PQ.

Example 2

Synthesis Example 2

In this example, a synthetic method of 4-(5-phenyl-1,3,4-oxadiazol-2-yl)-4'-(9-phenyl-9H-carbazol-3-yl)triphenylamine (abbreviation: PCBAO11) which is the carbazole derivative having the heteroaromatic ring and represented by the structural formula (67) of Embodiment 1 is explained.

(67)

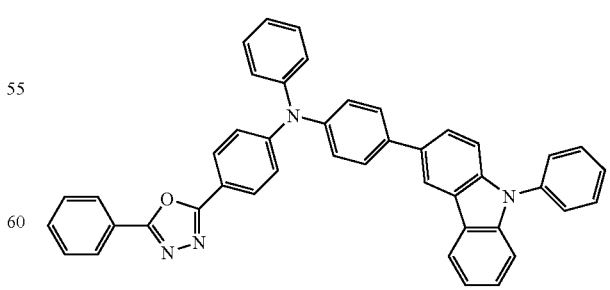

A scheme for the preparation of 4-(5-phenyl-1,3,4-oxadiazol-2-yl)-4'-(9-phenyl-9H-carbazol-3-yl)triphenylamine (abbreviation: PCBAO11) is shown in (M3).

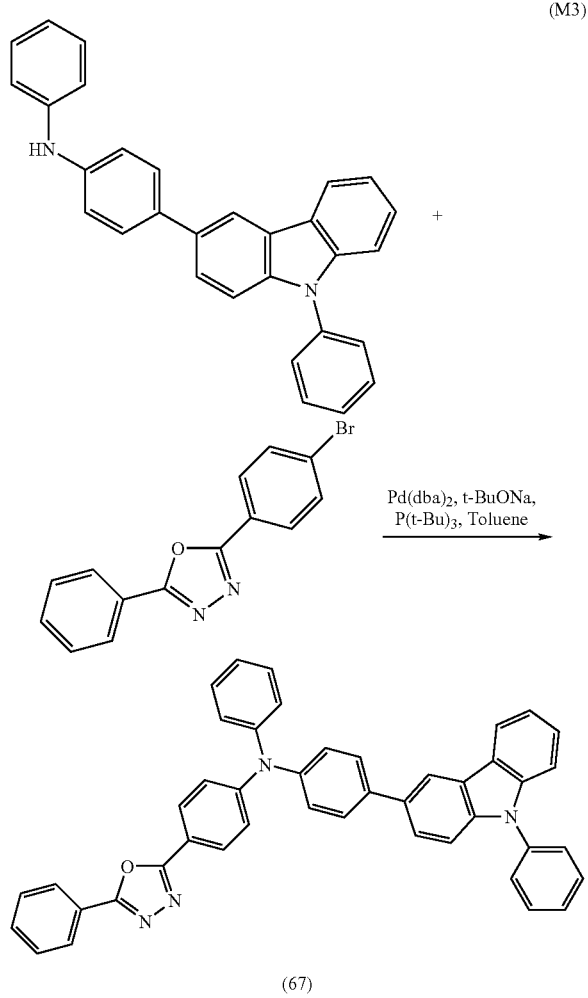

Into a 100 mL three-neck flask were added 1.8 g (4.3 mmol) of 4-(9-phenyl-9H-carbazol-3-yl)diphenylamine, 1.3 g (4.3 mmol) of 2-(4-bromobiphenyl)-5-phenyl-1,3,4-oxadiazole, and 1.0 g (10 mmol) of sodium tert-butoxide, and the atmosphere in the flask was substituted with nitrogen. After 15 mL of toluene and 0.10 mL of tri(tert-butyl)phosphine (a 10 wt % hexane solution) were added to the mixture, degassing was carried out with stirring under a reduced pressure, which was followed by the addition of 0.020 g (0.035 mmol) of bis(dibenzylideneacetone)palladium(0). This mixture was then heated with stirring at 80° C. for 5 hours.

After the reaction, toluene was added to this mixture, and the obtained suspension was subjected to suction filtration through Celite (manufactured by Wako Pure Chemical Industries, Ltd., Catalog No. 531-16855), alumina, and Florisil (manufactured by Wako Pure Chemical Industries, Ltd., Catalog No. 540-00135). The obtained filtrate was washed with a saturated aqueous solution of sodium carbonate and then with brine. The resulting organic layer was dried with magnesium sulfate, and the mixture was suction-filtrated to remove the magnesium sulfate. The resulting filtrate was concentrated, and the obtained residue was purified by silica gel column chromatography.

As the developing solvents in the column chromatography, toluene was used first, then a mixed solvent of toluene:ethyl acetate=20:1 was used in that order. The fractions obtained were concentrated, and the resulting solid was recrystallized with a mixed solvent of chloroform and hexane to give 2.5 g of a pale yellow powdered solid in 92% yield.

Sublimation purification of the solid obtained was performed by a train sublimation method. The sublimation purification was performed for 12 hours at 300° C. under the condition of 7 Pa and a flow rate of argon of 3 mL/min. The sublimation purification of 2.5 g of PCBAO11 gave a yield of 2.2 g (88% yield).

Figure 13A:
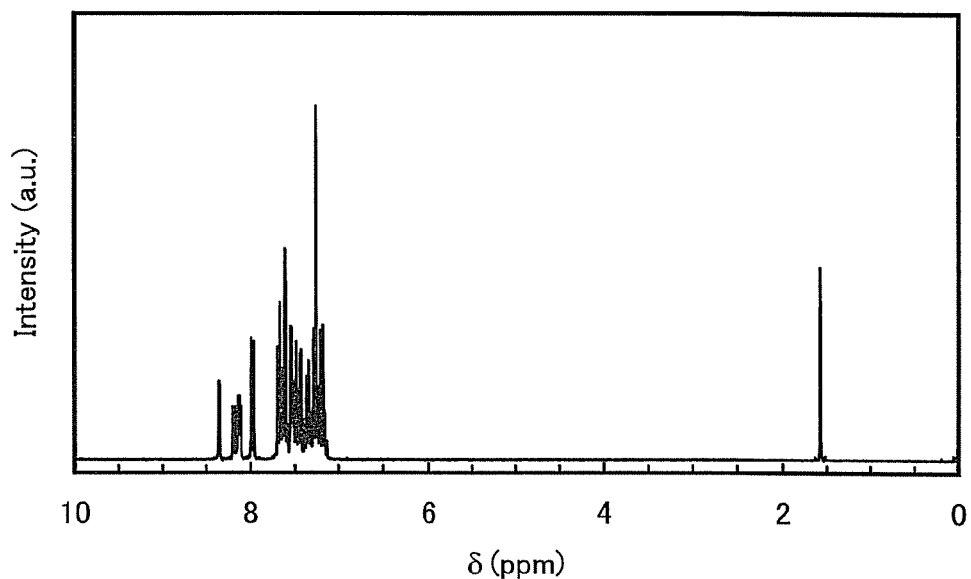
FIGS. 13A and 13B each are a $^1$H NMR chart of PCBAO11.
Figure 13B:
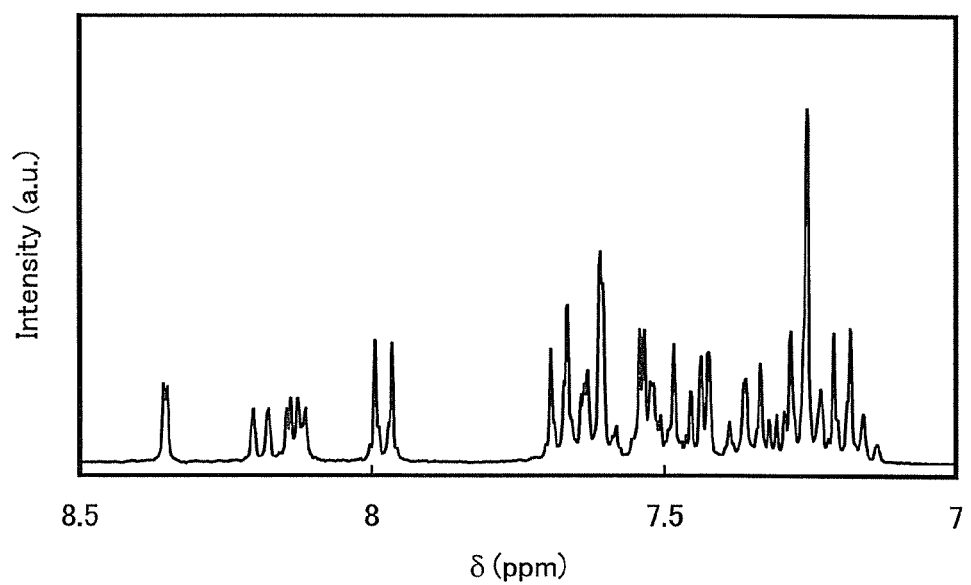

The result of an analysis of thus obtained powder by nuclear magnetic resonance spectrometry ($^1$H-NMR) is shown below. $^1$H-NMR charts are shown in FIGS. 13A and 13B. Note that FIG. 13B is a chart in which the range of 7.0 ppm to 8.5 ppm in FIG. 13A is enlarged.

$^1$H NMR (CDCl$_3$, 300 MHz): δ 7.13-7.70 (m, 24H), 7.98 (d, J=8.8 Hz, 2H), 8.11-8.15 (m, 2H), 8.19 (d, J=7.8 Hz, 1H), 8.35 (sd, J=2.0, 1H).

From the result of the $^1$H NMR analysis, the compound obtained in the present synthesis example was confirmed to be 4-(5-phenyl-1,3,4-oxadiazol-2-yl)-4'-(9-phenyl-9H-carbazol-3-yl)triphenylamine (abbreviation: PCBAO11) which is an embodiment of the present invention and is represented by the structural formula (67).

The glass transition temperature of PCBAO11, which was measured using a differential scanning calorimetry (Pyris 1 DSC, manufactured by Perkin Elmer Co., Ltd.), was 118° C. This result reveals that PCBAO11 is a material having favorable heat resistance.

Next, ultraviolet-visible absorption spectrum and the emission spectrum of PCBAO11 were measured. A toluene solution including PCBAO11 in a quartz cell and a thin film of PCBAO11 fabricated by vacuum evaporation onto a quartz substrate were used as samples. The absorption spectrum was measured with an ultraviolet-visible spectrophotometer (V-550, manufactured by JASCO Corporation). The emission spectrum was measured using a fluorescence spectrophotometer (FS920, manufactured by Hamamatsu Photonics Corporation).

Figure 14A:
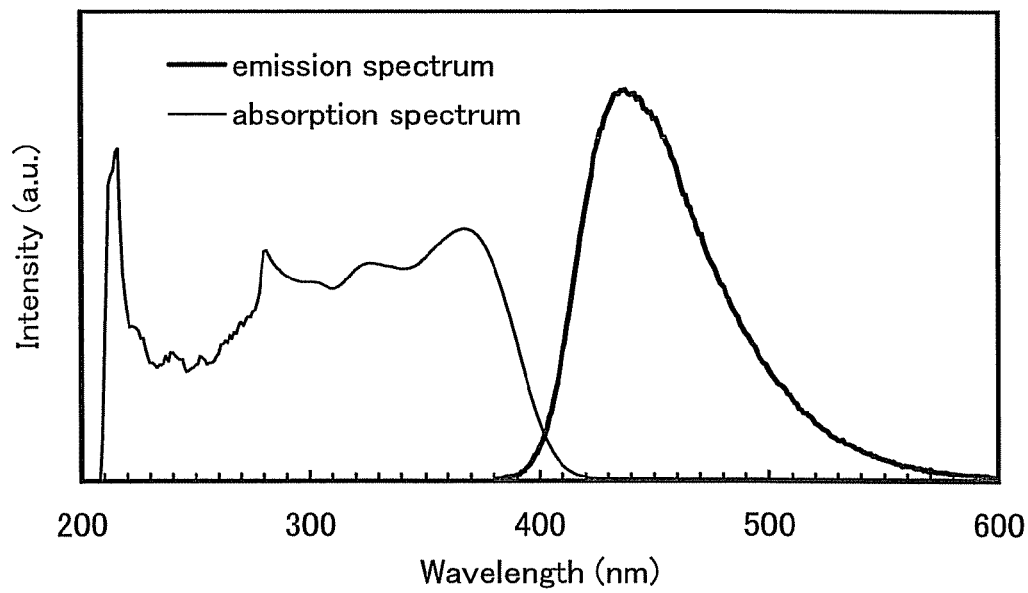
FIGS. 14A and 14B each illustrate UV-vis. absorption spectra and emission spectra of a toluene solution and a thin film of PCBAO11, respectively.
Figure 14B:
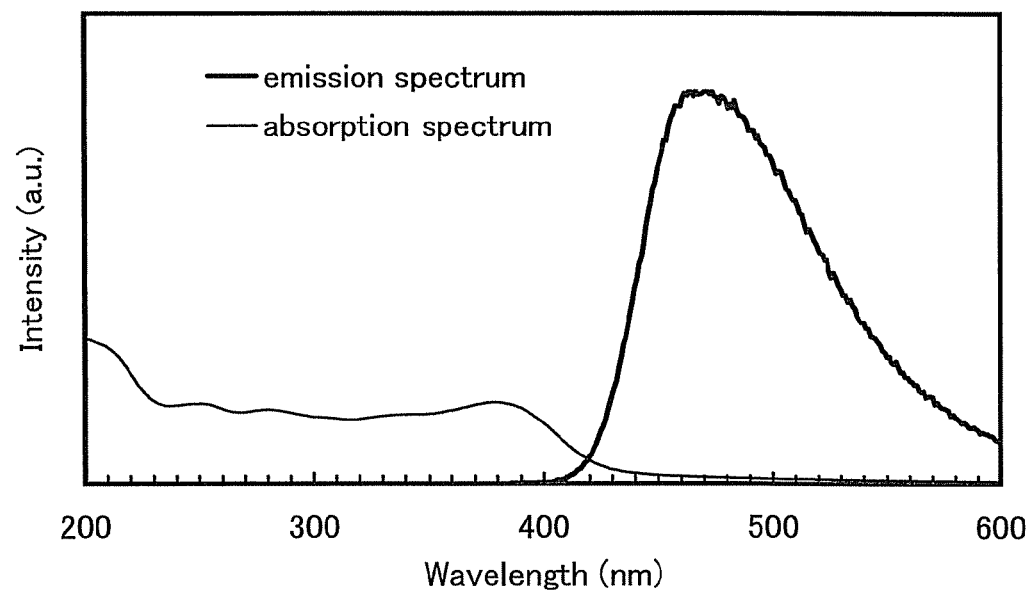

FIGS. 14A and 14B show the measurement results of the toluene solution and the thin film of PCBAO11, respectively. The horizontal axis represents wavelength (nm) and the vertical axis represents arbitrary intensity of absorbance and emission intensity. As for the absorption spectrum of the solution sample, the result obtained by subtraction of the absorption spectrum of the quartz cell including only toluene is shown. In the case of the thin film sample, the result obtained by subtraction of the absorption spectrum of the quartz substrate is shown.

The peak wavelength of the absorption spectrum of the toluene solution of PCBAO11 was 366 nm, and the peak wavelength of the fluorescent spectrum was 439 nm (excitation wavelength: 366 nm). The peak wavelength of the absorption spectrum of the thin film of PCBAO11 was 379 nm, and the peak wavelength of the fluorescent spectrum was 471 nm (excitation wavelength: 368 nm).

The HOMO level and LUMO level of PCBAO11 in the state of a thin film were estimated. The value of the HOMO level was obtained by converting the value of the ionization potential obtained with a photoelectron spectrometer (AC-2, manufactured by Riken Keiki Co., Ltd.) into a negative value. The value of the LUMO level was obtained in such a manner that the absorption edge, whish is obtained from Tauc plot with an assumption of direct transition using data on the absorption spectrum of the thin film of PCBAO11, is regarded as an optical energy gap and is added to the value of the HOMO level. As a result, the HOMO level, the energy gap, and the LUMO level of PCBAO11 were −5.39 eV, 2.98 eV, and −2.41 eV, respectively. Thus, it is proven that PCBA1PQ is an organic substance having a band gap of approximately 3 eV.

The oxidation-reduction reaction characteristics of PCBAO11 were evaluated. The oxidation-reduction characteristics were evaluated by cyclic voltammetry (CV) measurement. An electrochemical analyzer (ALS model 600A, manufactured by BAS Inc.) was used for the measurement.

As for a solution used for the CV measurement, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was dissolved in the solution such that the concentration thereof was 1 mmol/L. A platinum electrode (manufactured by BAS Inc., PIE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. The measurement was carried out at room temperature.

The oxidation characteristic of PCBAO11 was evaluated as follows. A scan for changing the potential of the working electrode with respect to the reference electrode from 0.214 V to 0.900 V and then from 0.900 V to 0.214 V was regarded as one cycle, and the measurement was performed for 100 cycles. The scanning speed of the CV measurement was 0.1 V/s.

The reduction characteristics of PCBAO11 were evaluated as follows. A scan for changing the potential of the working electrode with respect to the reference electrode from −1.25 V to −2.65 V and then from −2.65 V to −1.25 V was regarded as one cycle, and the measurement was performed for 100 cycles. The scanning speed of the CV measurement was 0.1 V/s.

Figure 15A:
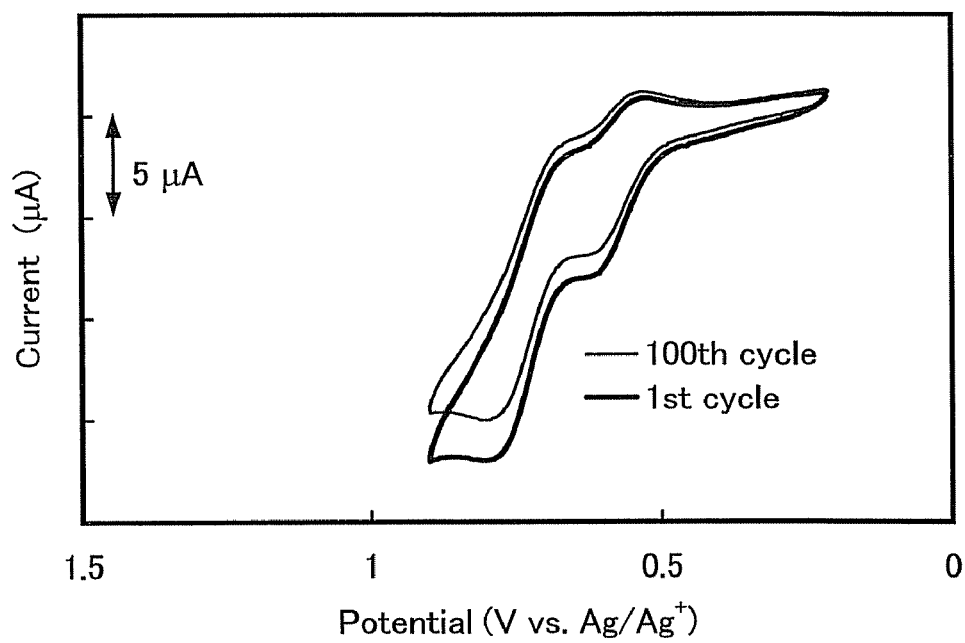
FIGS. 15A and 15B each illustrate a result of CV measurement of PCBAO11.
Figure 15B:
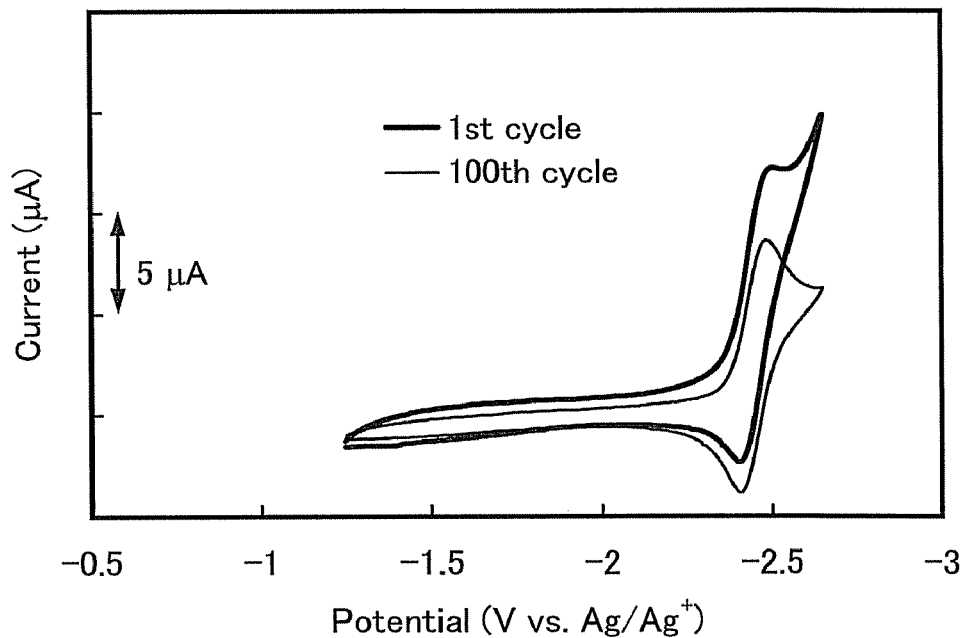

FIGS. 15A and 15B show CV measurement results on the oxidation side and the reduction side of PCBAO11, respectively. In FIGS. 15A and 15B, the horizontal axis shows potential (V) of the work electrode with respect to the reference electrode, and the vertical axis shows a value (μA) of current flowing between the working electrode and the auxiliary electrode. In FIG. 15A, a current indicating oxidation is observed at around +0.58 V (vs. Ag/Ag$^+$). In FIG. 12B, a current indicating reduction is observed at around −2.46 V (vs. Ag/Ag$^+$).

Although the scan was repeated as many as 100 cycles, no significant change in the peak position and peak intensity of the CV curves was observed in both the oxidation and the reduction, which proves that the carbazole derivative having the heteroaromatic ring according to the present invention is stable even if oxidation and reduction are repeatedly performed.

Example 3

Synthesis Example 3

In the present example, a synthetic method of 9-phenyl-9'-[4-(3-phenylqunoxalin-2-yl)phenyl]-3,3'-bi(9H-carbazol) (abbreviation: PCC1PQ) which is the carbazole derivative having the heteroaromatic ring and represented by the structural formula (35) of Embodiment 1 is explained.

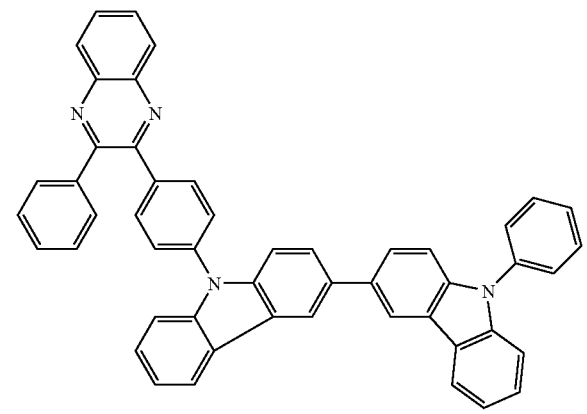

(35)

A scheme for the preparation of 9-phenyl-9'-[4-(3-phenylqunoxalin-2-yl)phenyl]-3,3'-bi(9H-carbazol) (abbreviation: PCC1PQ) is shown in (M4).

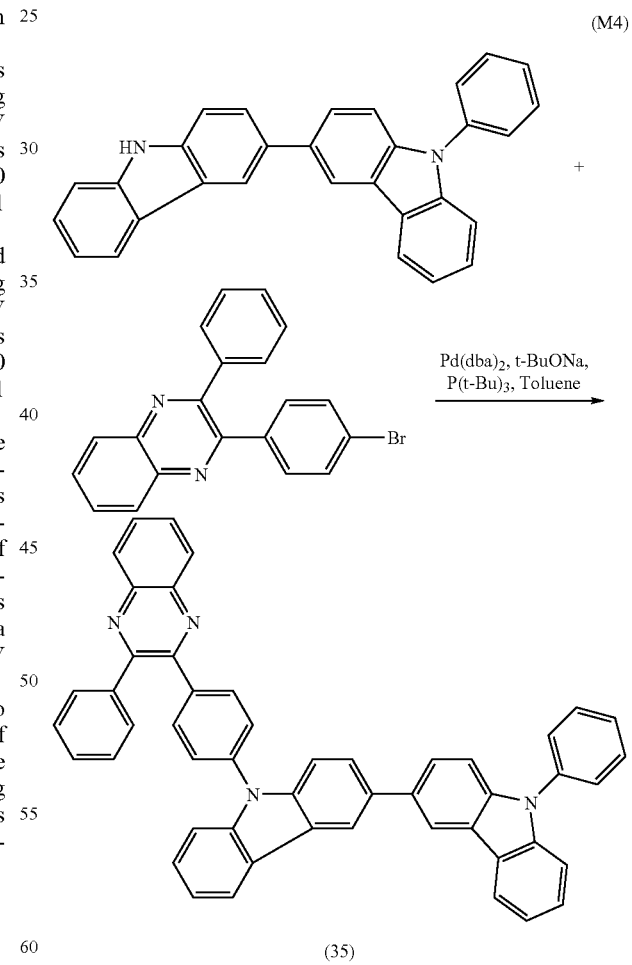

(M4)

(35)

Into a 100 mL three-neck flask were added 1.7 g (4.2 mmol) of 9-phenyl-3,3'-bi(9H-carbazol), 1.5 g (4.2 mmol) of 2-(4-bromobiphenyl)-3-phenylqunoxaline, and 1.0 g (10 mmol) of sodium tert-butoxide, and the atmosphere in the flask was substituted with nitrogen. After 15 mL, of toluene and 0.10 mL of tri(tert-butyl)phosphine (a 10 wt % hexane solution) were added to the mixture, degassing was carried out with stirring under a reduced pressure, which was followed by the addition of 0.020 g (0.035 mmol) of bis(dibenzylideneacetone)palladium(0). This mixture was then heated with stirring at 80° C. for 5 hours.

After the reaction, toluene was added to this mixture, and the obtained suspension was subjected to suction filtration through Celite (manufactured by Wako Pure Chemical Industries, Ltd., Catalog No. 531-16855), Florisil (manufactured by Wako Pure Chemical Industries, Ltd., Catalog No. 540-00135), and alumina. The obtained filtrate was washed with water, and the organic layer was dried with magnesium sulfate. The mixture was suction-filtrated to remove the magnesium sulfate. The resulting filtrate was concentrated, and the obtained residue was purified by silica gel column chromatography.

As the developing solvents in the column chromatography, a mixed solvent of toluene:hexane=1:1 was used first, then toluene was next used, and a mixed solvent of toluene:ethyl acetate=5:1 was used in that order. The fractions obtained were concentrated, and the resulting solid was recrystallized with a mixed solvent of dichloromethane and methanol to give 2.2 g of a pale yellow powdered solid in 75% yield.

Sublimation purification of the solid obtained was performed by a train sublimation method. The sublimation purification was performed for 22 hours at 320° C. under the condition of 7 Pa and a flow rate of argon of 3 mL/min. The sublimation purification of 1.7 g of PCC1PQ gave a yield of 0.85 g (50% yield).

Figure 16A:
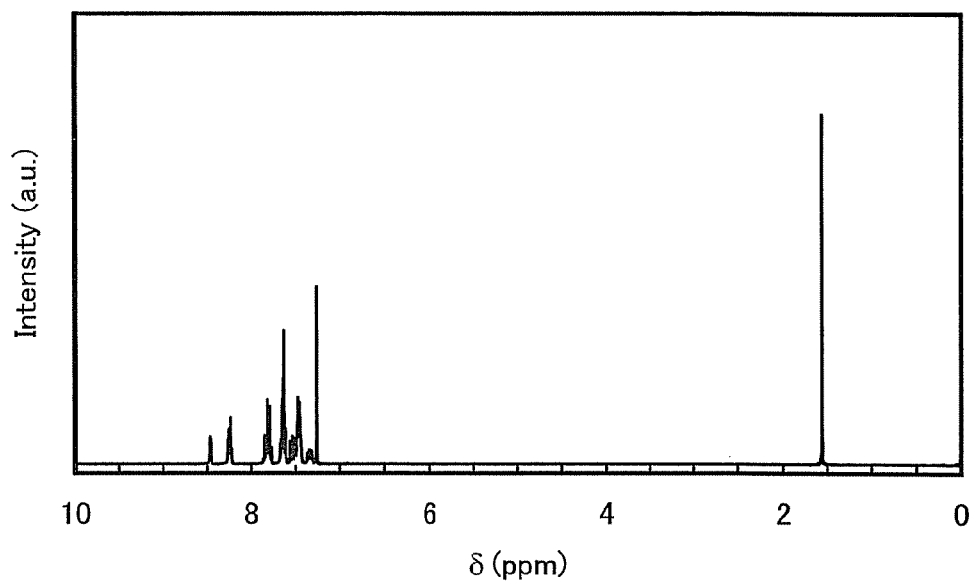
FIGS. 16A and 16B each are a $^1$H NMR chart of PCC1PQ.
Figure 16B:
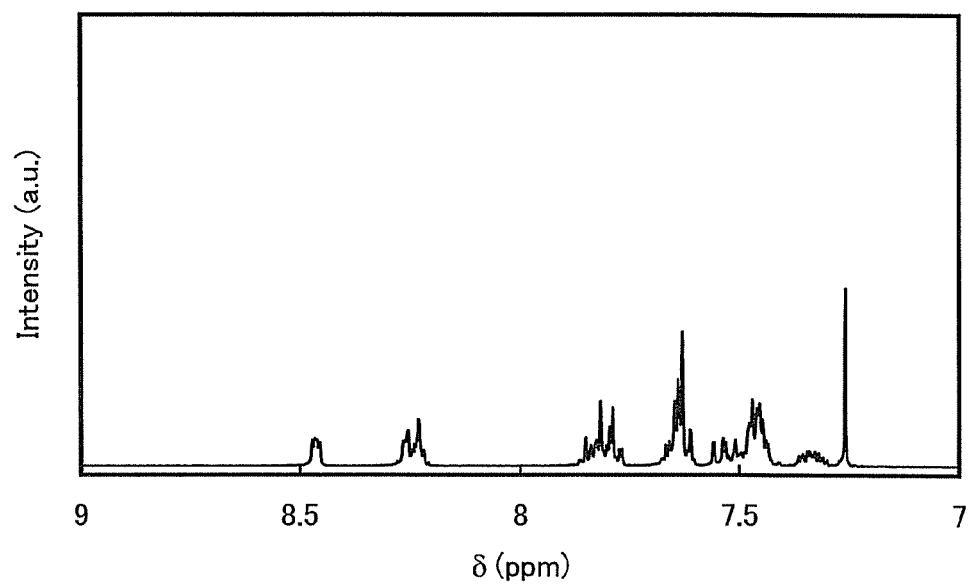

The result of an analysis of thus obtained powder by nuclear magnetic resonance spectrometry ($^1$H-NMR) is shown below. $^1$H-NMR charts are shown in FIGS. 16A and 16B. Note that FIG. 16B is a chart in which the range of 7.0 ppm to 9.0 ppm in FIG. 16A is enlarged.

$^1$H NMR (CDCl$_3$, 300 MHz): δ 7.29-7.36 (m, 2H), 7.44-7.86 (m, 24H), 8.22-8.27 (m, 4H), 8.45-8.48 (m, 2H).

From the result of the $^1$H NMR analysis, the compound obtained in the present synthesis example was confirmed to be 9-phenyl-9'-[4-(3-phenylqunoxalin-2-yl)phenyl]-3,3'-bi(9H-carbazol) (abbreviation: PCC1PQ) which is an embodiment of the present invention and is represented by the structural formula (35).

Next, the ultraviolet-visible absorption spectrum and the emission spectrum of PCC1PQ were measured. A toluene solution including PCC1PQ in a quartz cell and a thin film of PCC1PQ fabricated by vacuum evaporation onto a quartz substrate were used as samples. The absorption spectrum was measured with an ultraviolet-visible spectrophotometer (V-550, manufactured by JASCO Corporation). The emission spectrum was measured using a fluorescence spectrophotometer (FS920, manufactured by Hamamatsu Photonics Corporation).

Figure 17A:
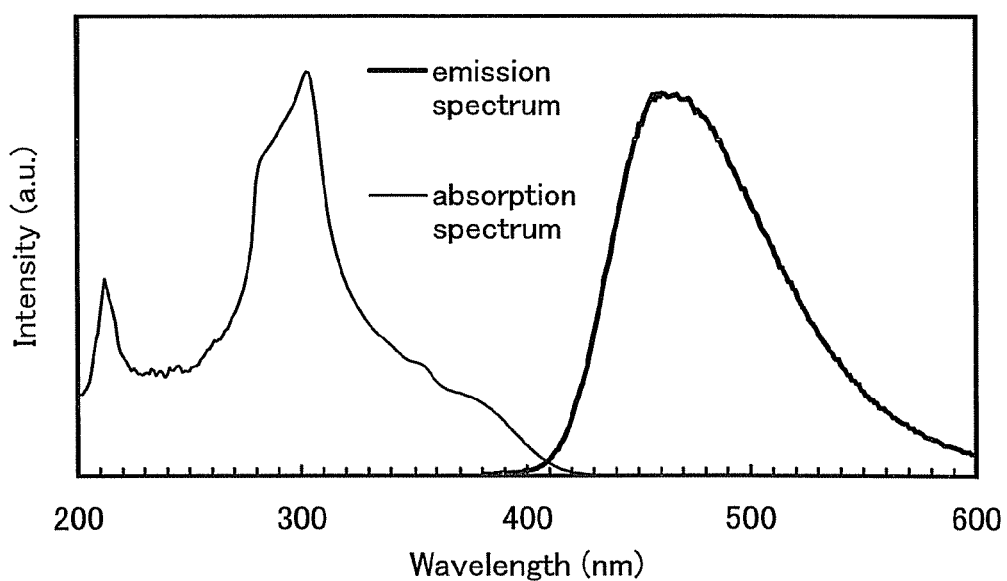
FIGS. 17A and 17B each illustrate UV-vis. absorption spectra and emission spectra of a toluene solution and a thin film of PCC1PQ, respectively.
Figure 17B:
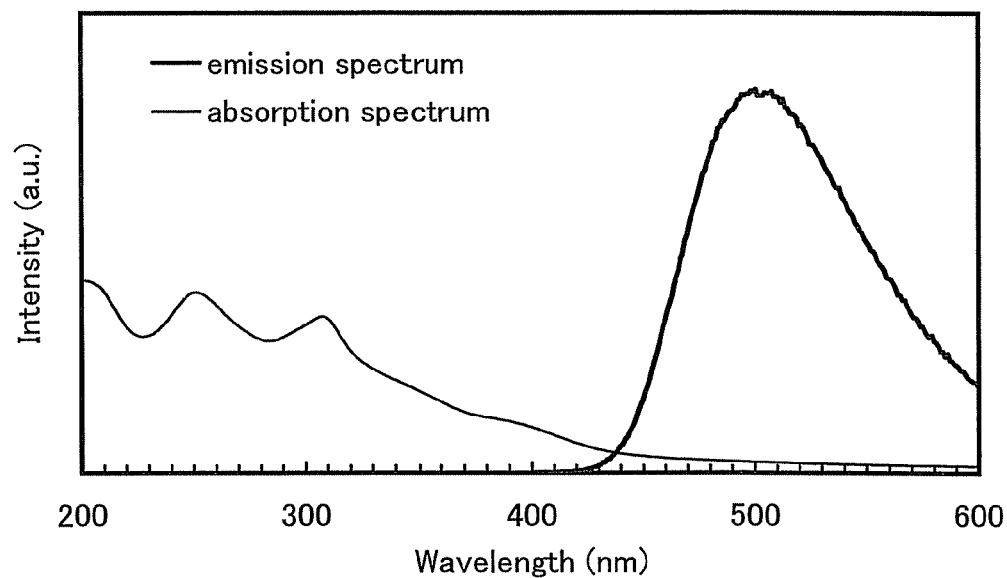

FIGS. 17A and 17B show the measurement results of the toluene solution and the thin film of PCC1PQ, respectively. The horizontal axis represents wavelength (nm) and the vertical axis represents arbitrary intensity of absorbance and emission intensity. As for the absorption spectrum of the solution sample, the result obtained by subtraction of the absorption spectrum of the quartz cell including only toluene is shown. In the case of the thin film sample, the result obtained by subtraction of the absorption spectrum of the quartz substrate is shown.

The peak wavelength of the absorption spectrum of the toluene solution of PCC1PQ was 371 nm, and the peak wavelength of the fluorescent spectrum was 466 nm (excitation wavelength: 371 nm). The peak wavelength of the absorption spectrum of the thin film of PCC1PQ was 386 nm, and the peak wavelength of the fluorescent spectrum was 503 nm (excitation wavelength: 307 nm).

Further, the HOMO level and LUMO level of PCzPCN1 in a state of a thin film were estimated. The HOMO level and LUMO level of PCC1PQ in the state of a thin film were measured. The value of the HOMO level was obtained by converting the value of the ionization potential obtained with a photoelectron spectrometer (AC-2, manufactured by Riken Keiki Co., Ltd.) into a negative value. The value of the LUMO level was obtained in such a manner that the absorption edge, whish is obtained from Tauc plot with an assumption of direct transition using data on the absorption spectrum of the thin film of PCC1PQ, is regarded as an optical energy gap and is added to the value of the HOMO level. As a result, the HOMO level, the energy gap, and the LUMO level of PCC1PQwere −5.55 eV, 2.88 eV, and −2.67 eV, respectively. Thus, it was proven that PCC1PQ is a compound having a band gap greater than 2 eV.

The oxidation-reduction reaction characteristics of PCC1PQ were evaluated. The oxidation-reduction characteristics were evaluated by cyclic voltammetry (CV) measurement. An electrochemical analyzer (ALS model 600A, manufactured by BAS Inc.) was used for the measurement.

As for a solution used for the CV measurement, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was dissolved in the solution such that the concentration thereof was 1 mmol/L. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. The measurement was carried out at room temperature.

The oxidation characteristic of PCC1PQ was evaluated as follows. A scan for changing the potential of the working electrode with respect to the reference electrode from 0.026 V to 0.839 V and then from 0.839 V to 0.026 V was regarded one cycle, and the measurement was performed for 100 cycles. The scanning speed of the CV measurement was 0.1 V/s.

The reduction characteristics of PCC1PQ were evaluated as follows. A scan for changing the potential of the working electrode with respect to the reference electrode from −1.37 V to −2.19 V and then from −2.19 V to −1.37 V was regarded as one cycle, and the measurement was performed for 100 cycles. The scanning speed of the CV measurement was 0.1 V/s.

Figure 18A:
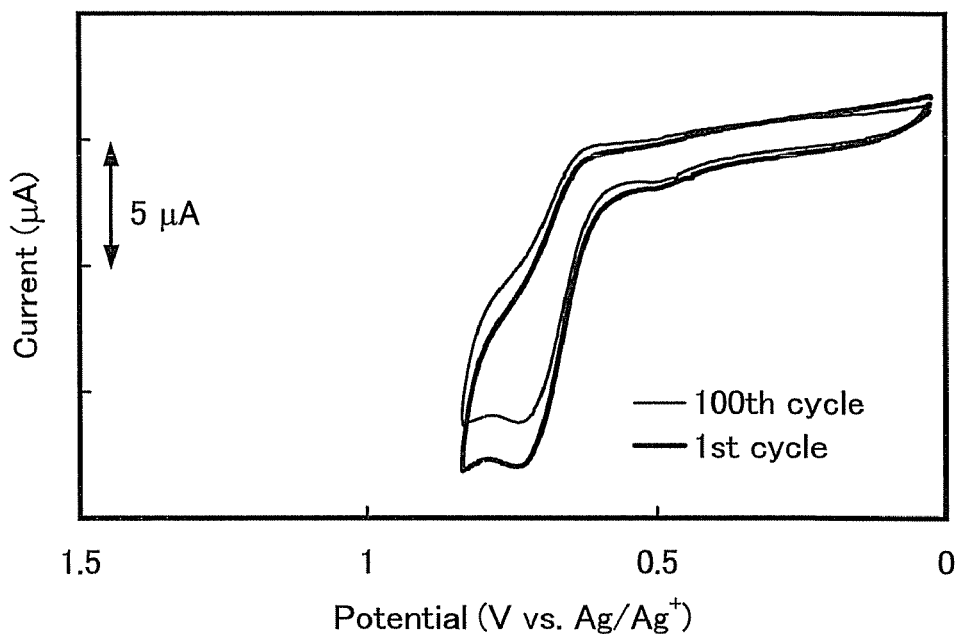
FIGS. 18A and 18B each illustrate a result of CV measurement of PCC1PQ.
Figure 18B:
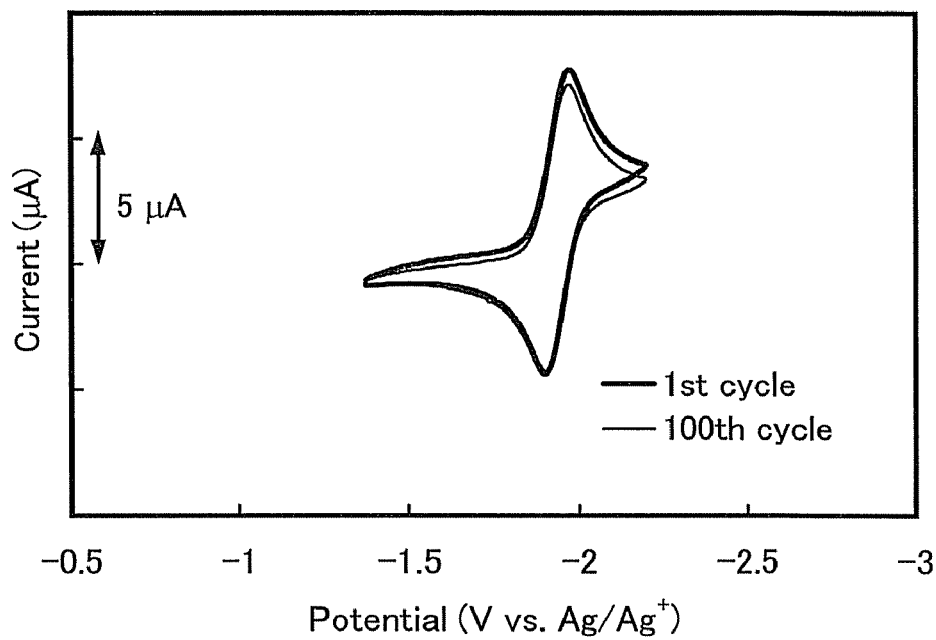

FIGS. 18A and 18B show CV measurement results on the oxidation side and the reduction side of PCC1PQ, respectively. In FIGS. 18A and 18B, the horizontal axis shows potential (V) of the work electrode with respect to the reference electrode, and the vertical axis shows a value (μA) of current flowing between the work electrode and the auxiliary electrode. In FIG. 18A, a current indicating oxidation is observed at around +0.67 V (vs. Ag/Ag$^+$). In FIG. 18B, a current indicating reduction is observed at around −1.93 V (vs. Ag/Ag$^+$).

Although the scan was repeated as many as 100 cycles, no significant change in the peak position and peak intensity of the CV curves was observed in both the oxidation and the reduction, which proves that the carbazole derivative having the heteroaromatic ring according to the present invention is stable even if oxidation and reduction are repeatedly performed.

Example 4

Synthesis Example 4

In the present example, a synthetic method of 9-phenyl-9'-[4-(5-phenyl-1,3,4-oxadiazole-2-yl)phenyl]-3,3'-bi(9H-carbazole) (abbreviation: PCCO11) which is the carbazole derivative having the heteroaromatic ring and represented by the structural formula (99) of Embodiment 1 is explained.

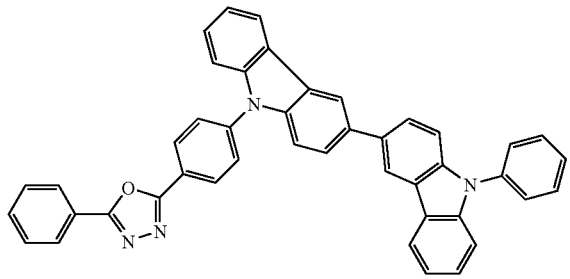

(99)

A scheme for the preparation of 9-phenyl-9'-[4-(5-phenyl-1,3,4-oxadiazole-2-yl)phenyl]-3,3'-bi(9H-carbazole) (abbreviation: PCCO11) is shown in (M5).

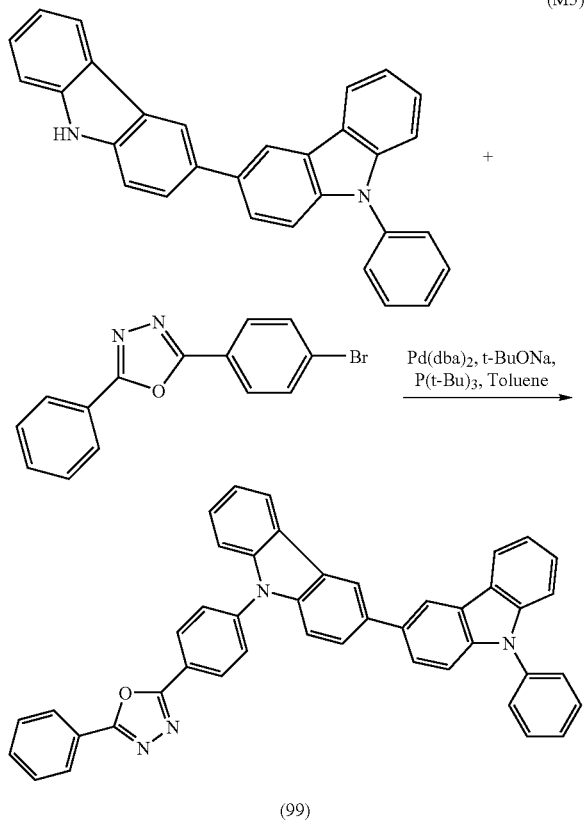

(M5)

(99)

Into a 100 mL three-neck flask were added 1.8 g (4.3 mmol) of 9-phenyl-3,3'-bi(9H-carbazole), 1.3 g (4.3 mmol) of 2-(4-bromobiphenyl)-5-phenyl-1,3,4-oxadiazole, and 1.0 g (10 mmol) of sodium tert-butoxide were put, and the atmosphere in the flask was substituted with nitrogen. After 15 mL of toluene and 0.1 mL of tri(tert-butyl)phosphine (a 10 wt % hexane solution) were added to the mixture, degassing was carried out with stirring under a reduced pressure. After degassing, 0.020 g (0.035 mmol) of bis(dibenzylideneacetone)palladium(0) was added to the mixture, and the mixture was heated with stirring at 80° C. for 5 hours.

After the reaction, toluene was added to this mixture, and the obtained suspension was subjected to suction filtration through Celite (manufactured by Wako Pure Chemical Industries, Ltd., Catalog No. 531-16855), alumina, and Florisil (manufactured by Wako Pure Chemical Industries, Ltd., Catalog No. 540-00135). The obtained filtrate was washed with a saturated aqueous solution of sodium carbonate and then with brine. The organic layer was dried with magnesium sulfate, and the mixture was suction-filtrated to remove the magnesium sulfate. The resulting filtrate was concentrated, and the obtained solid was purified by silica gel column chromatography.

As the developing solvents in the column chromatography, toluene was used first, then a mixed solvent of toluene:ethyl acetate=20:1 was used in that order. The fractions obtained were concentrated, and the resulting solid was recrystallized with a mixed solvent of chloroform and hexane to give 2.1 g of a pale yellow powdered solid in 78% yield.

Sublimation purification of the solid obtained was performed by a train sublimation method. The sublimation purification was performed for 12 hours at 320° C. under the condition of 7 Pa and a flow rate of argon of 3 mL/min. The sublimation purification of 1.8 g of PCCO11 gave a yield of 1.1 g (61% yield).

Figure 19A:
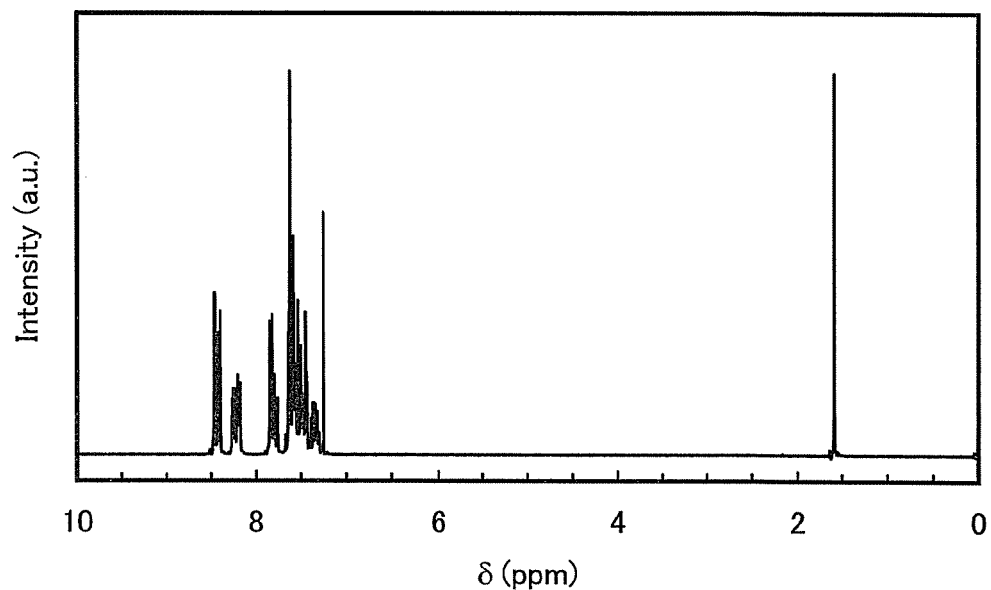
FIGS. 19A and 19B each are a $^1$H NMR chart of PCCO11.
Figure 19B:
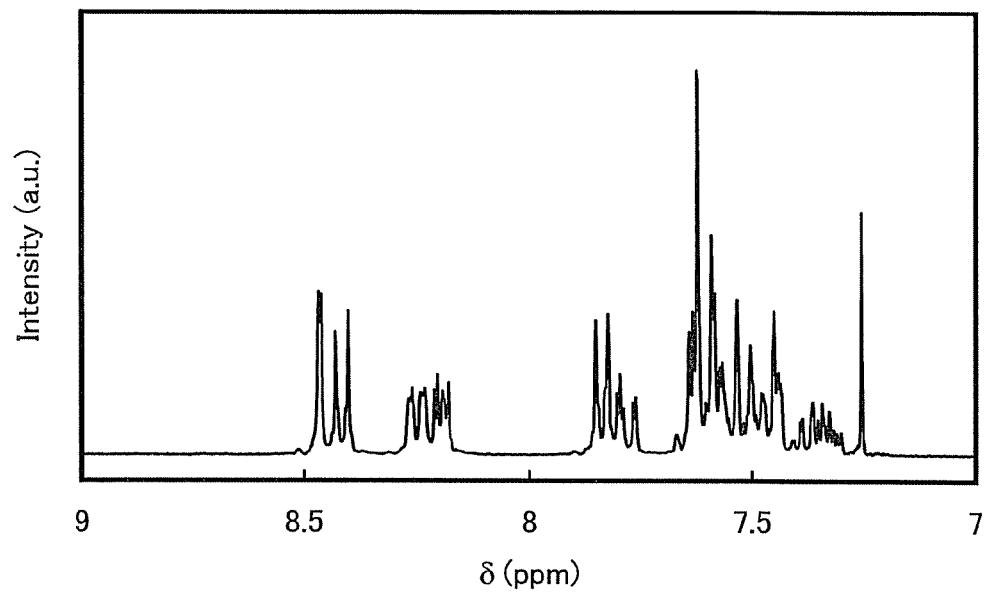

The result of an analysis of thus obtained powder by nuclear magnetic resonance spectrometry ($^1$H-NMR) is shown below. $^1$H-NMR charts are shown in FIGS. 19A and 19B. Note that FIG. 19B is a chart in which the range of 7.0 ppm to 9.0 ppm in FIG. 19A is enlarged.

$^1$H NMR (CDCl$_3$, 300 MHz): δ 7.30-7.65 (m, 16H), 7.75-7.86 (m, 4H), 8.18-8.28 (m, 4H), 8.42 (d, J=8.8 Hz, 2H), 8.47 (sd, J=1.5 Hz, 2H).

From the result of the $^1$H NMR analysis, the compound obtained in the present synthesis example was confirmed to be 9-phenyl-9'-[4-(5-phenyl-1,3,4-oxadiazole-2-yl)phenyl]-3,3'-bi(9H-carbazole) (abbreviation: PCCO11) which is an embodiment of the present invention and is represented by the structural formula (99).

The glass transition temperature of PCCO11, which was measured using a differential scanning calorimetry (Pyris 1 DSC, manufactured by Perkin Elmer Co., Ltd.), was 138° C. From these results, it was found that PCCO11 was a material having favorable heat resistance.

Next, ultraviolet-visible absorption spectrum and the emission spectrum of PCCO11 were measured. A toluene solution including PCCO11 in a quartz cell and a thin film of PCCO11 fabricated by vacuum evaporation onto a quartz substrate were used as samples. The absorption spectrum was measured with an ultraviolet-visible spectrophotometer (V-550, manufactured by JASCO Corporation). The emission spectrum was measured using a fluorescence spectrophotometer (FS920, manufactured by Hamamatsu Photonics Corporation).

Figure 20A:
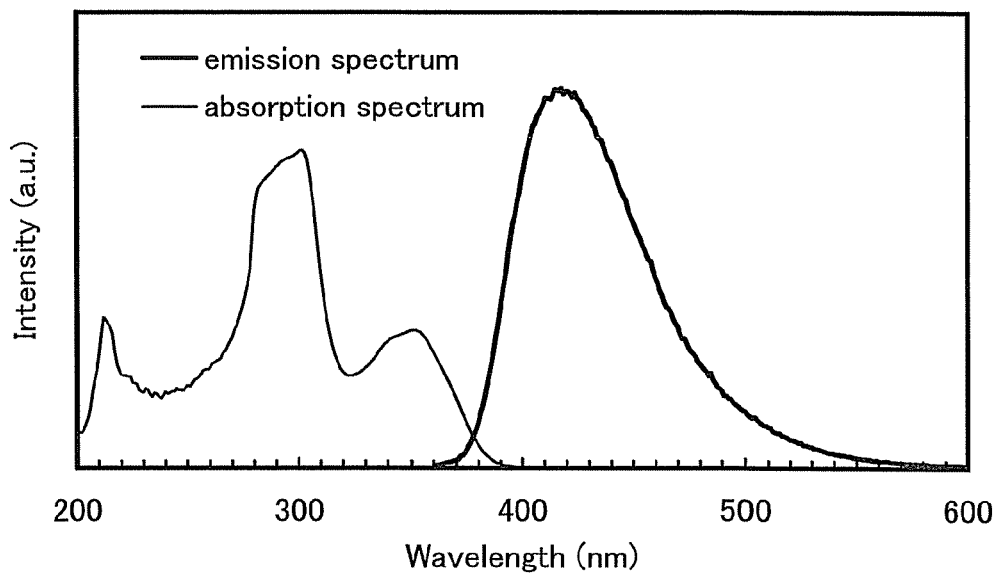
FIGS. 20A and 20B each illustrate UV-vis. absorption spectra and emission spectra of a toluene solution and a thin film of PCCO11, respectively.
Figure 20B:
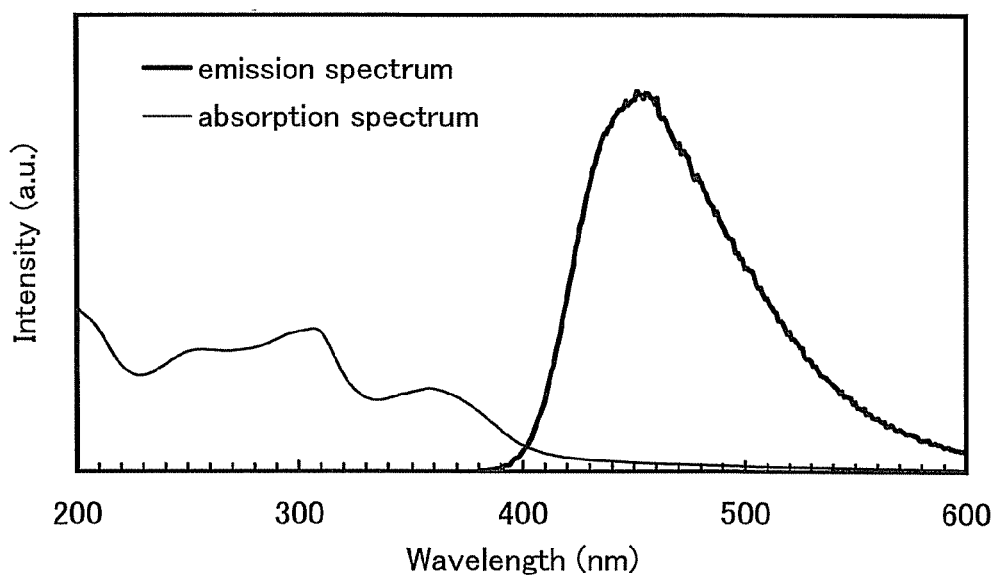

FIGS. 20A and 20B show the measurement results of the toluene solution and the thin film of PCCO11, respectively. The horizontal axis represents wavelength (nm) and the vertical axis represents arbitrary intensity of absorbance and emission intensity. As for the absorption spectrum of the solution sample, the result obtained by subtraction of the absorption spectrum of the quartz cell including only toluene is shown. In the case of the thin film sample, the result obtained by subtraction of the absorption spectrum of the quartz substrate is shown.

The peak wavelength of the absorption spectrum of the toluene solution of PCCO11 was 350 nm, and the peak wavelength of the fluorescent spectrum was 418 nm (excitation wavelength: 350 nm). The peak wavelength of the absorption spectrum of the thin film of PCCO11 was 358 nm, and the peak wavelength of the fluorescent spectrum was 456 nm (excitation wavelength: 355 nm).

The HOMO level and LUMO level of PCCO11 in the state of a thin film were estimated. The value of the HOMO level was obtained by converting the value of the ionization potential obtained with a photoelectron spectrometer (AC-2, manufactured by Riken Keiki Co., Ltd.) into a negative value. The value of the LUMO level was obtained in such a manner that the absorption edge, whish is obtained from Tauc plot with an assumption of direct transition using data on the absorption spectrum of the thin film of PCCO11, is regarded as an optical energy gap and is added to the value of the HOMO level. As a result, the HOMO level, the energy gap, and the LUMO level of PCCO11 were −5.47 eV, 3.02 eV, and −2.45 eV, respectively. Thus, it was proven that PCCO11 is an organic substance having a band gap greater than 3 eV.

The oxidation-reduction reaction characteristics of PCCO11 were evaluated. The oxidation-reduction characteristics were evaluated by cyclic voltammetry (CV) measurement. An electrochemical analyzer (ALS model 600A, manufactured by BAS Inc.) was used for the measurement.

As for a solution used for the CV measurement, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was dissolved in the solution such that the concentration thereof was 1 mmol/L. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. The measurement was carried out at room temperature.

The oxidation characteristic of PCCO11 was evaluated as follows. A scan for changing the potential of the working electrode with respect to the reference electrode from 0.324 V to 0.800 V and then from 0.800 V to 0.324 V was regarded as one cycle, and the measurement was performed for 100 cycles. The scanning speed of the CV measurement was 0.1 V/s.

The reduction characteristics of PCCO11 were evaluated as follows. A scan for changing the potential of the working electrode with respect to the reference electrode from −1.59 V to −2.49 V and then from −2.49 V to −1.59 V was regarded as one cycle, and the measurement was performed for 100 cycles. The scanning speed of the CV measurement was 0.1 V/s.

Figure 21A:
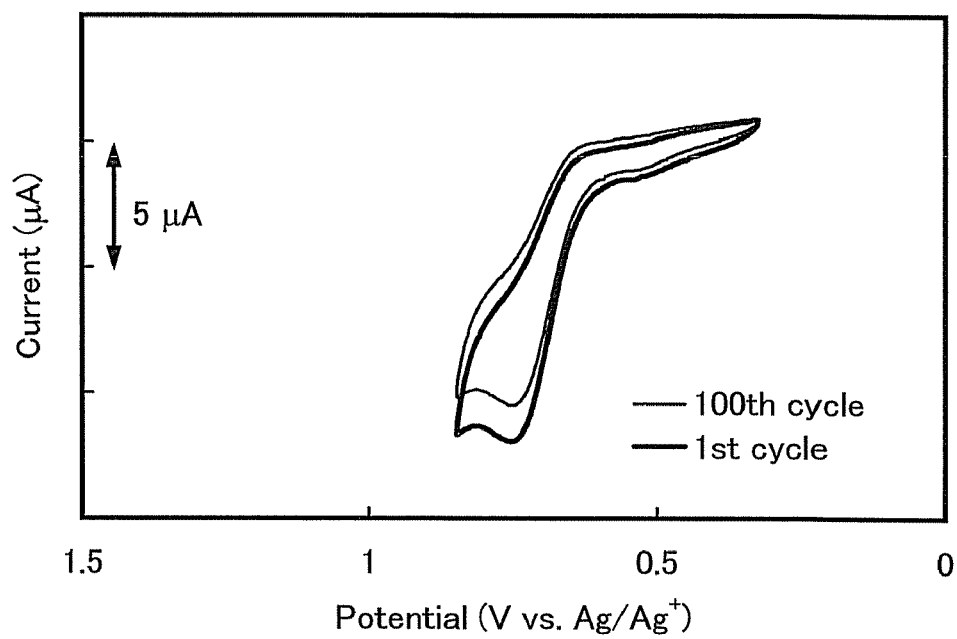
FIGS. 21A and 21B each illustrate a result of CV measurement of PCCO11.
Figure 21B:
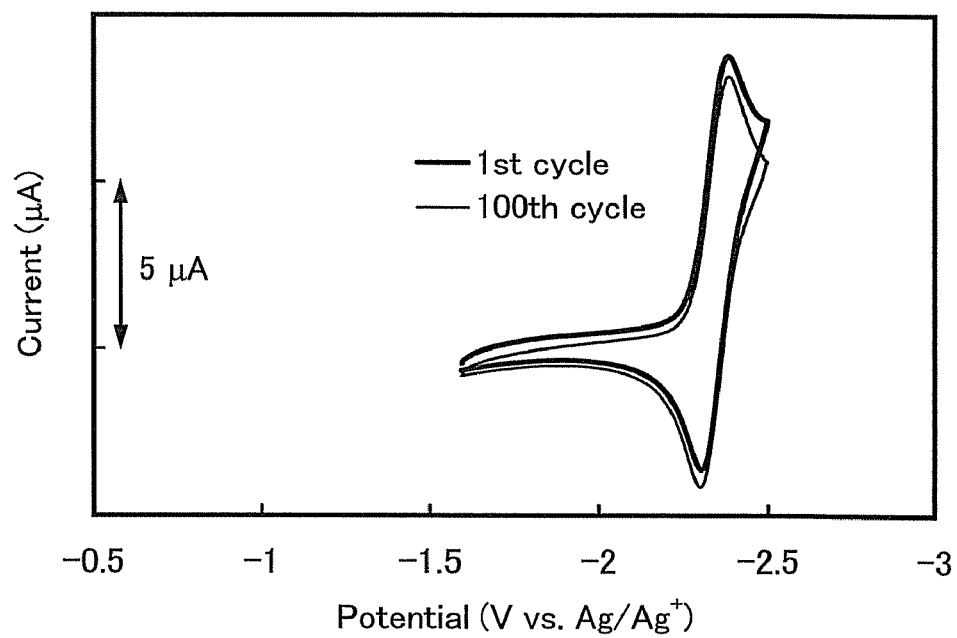
Figure 22:
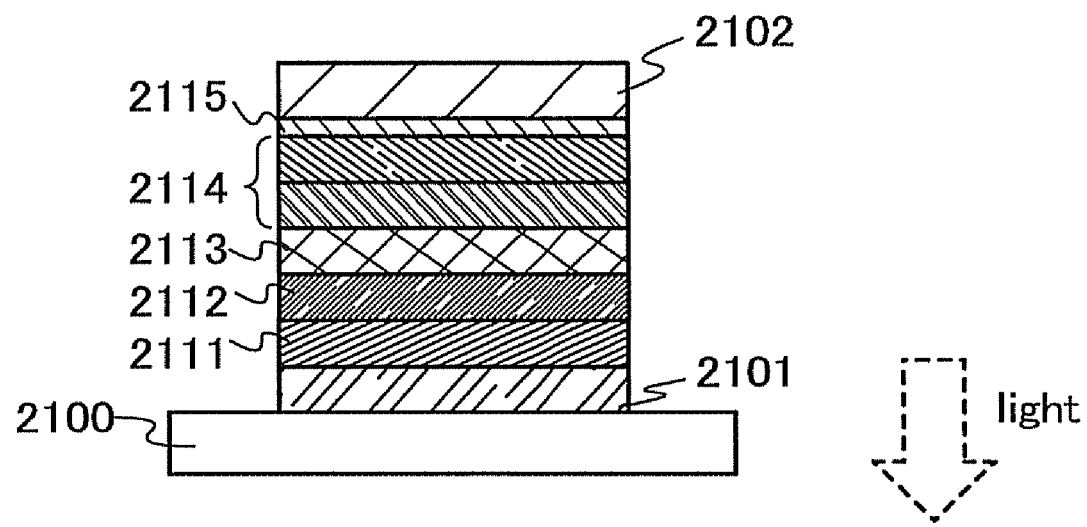
FIG. 22 illustrates the light-emitting element fabricated in Example.

FIGS. 21A and 21B show CV measurement results on the oxidation side and the reduction side of PCCO11, respectively. In FIGS. 21A and 21B, the horizontal axis shows potential (V) of the work electrode with respect to the reference electrode, and the vertical axis shows a value (μA) of current flowing between the work electrode and the auxiliary electrode. In FIG. 21A, a current indicating oxidation is observed at around +0.69 V (vs. Ag/Ag$^+$). In FIG. 21B, a current indicating reduction is observed at around −2.34 V (vs. Ag/Ag$^+$).

Although the scan was repeated as many as 100 cycles, no significant change in the peak position and peak intensity of the CV curves was observed in both the oxidation and the reduction, which proves that the carbazole derivative having the heteroaromatic ring according to the present invention is stable even if oxidation and reduction are repeatedly performed.

The molecular structure of PCCO11 in the ground state was optimized by a similar method as that for the aforementioned PCBA1PQ.

Figure 28A:
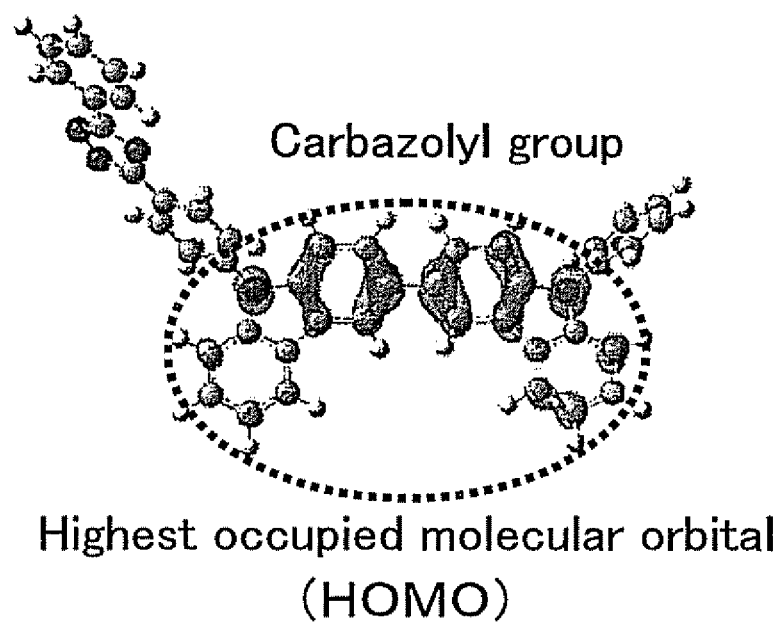
FIGS. 28A and 28B illustrate the highest occupied molecular orbital (HOMO) and the lowest unoccupied molecular orbital (LUMO) of an optimal molecular structure of PCCO11, respectively.
Figure 28B:
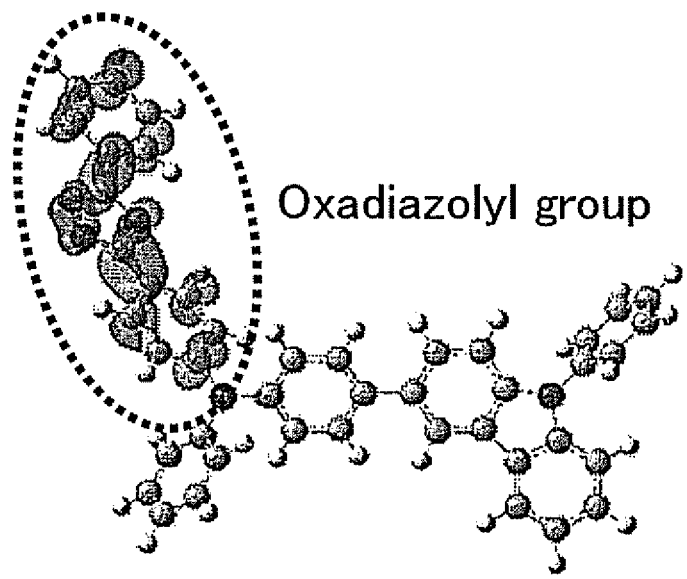

The highest occupied molecular orbital (HOMO) and the lowest unoccupied molecular orbital (LUMO) of the optimal molecular structure of PCCO11 obtained by the calculation are visualized using Gauss View 4.1 and shown in FIGS. 28A and 28B. FIG. 28A shows the highest occupied molecular orbital (HOMO), and FIG. 28B shows the lowest unoccupied molecular orbital (LUMO). The spheres in FIGS. 28A and 28B represent atoms which form PCCO11, and cloud-like objects located around atoms represent the highest occupied molecular orbital (HOMO) or the lowest unoccupied molecular orbital (LUMO).

From FIGS. 28A and 28B, it is revealed that the highest occupied molecular orbital is localized around the carbazole group, which indicates that the carbazolyl group significantly contributes to the hole-transporting property of PCCO11. Moreover, the lowest unoccupied molecular orbital is localized around the oxadiazole group, which proves that the oxadiazole group significantly contributes to the electron-transporting property of PCCO11. Therefore, it can be understood that a bipolar material can be realized because both the oxadiazole moiety having a heteroaromatic ring with an electron-transporting property and the carbazole moiety having a hole-transporting property are incorporated to PCCO11.

Example 5

In this example, a light-emitting element of an embodiment of the present invention will be described with reference to FIGS. 22, 23A, 23B, 24A, and 24B. Chemical formulae of the materials used in this example are shown below.

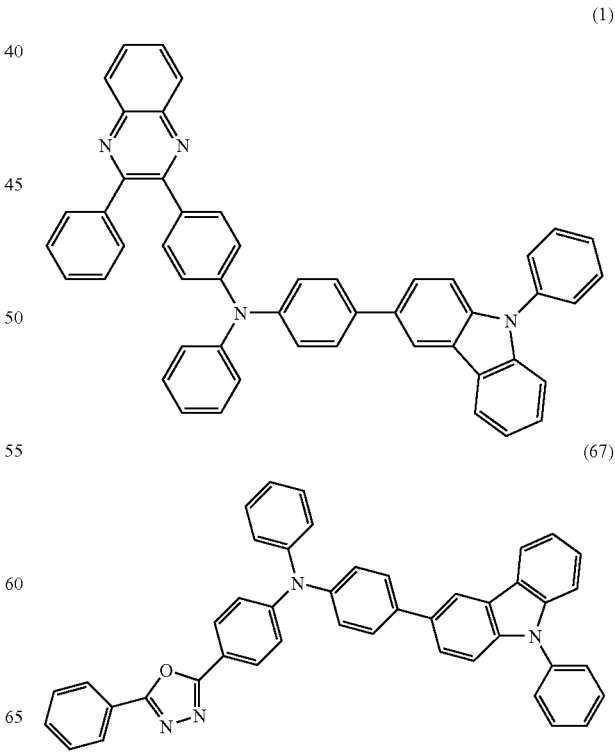

(35)

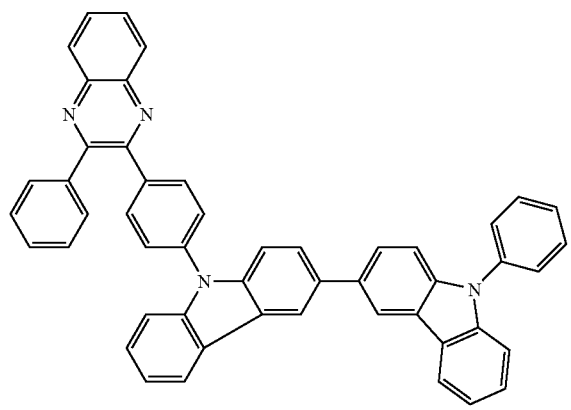

(99)

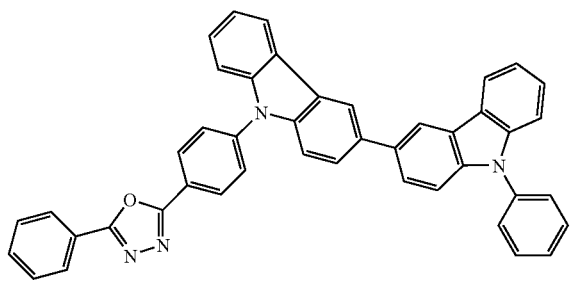

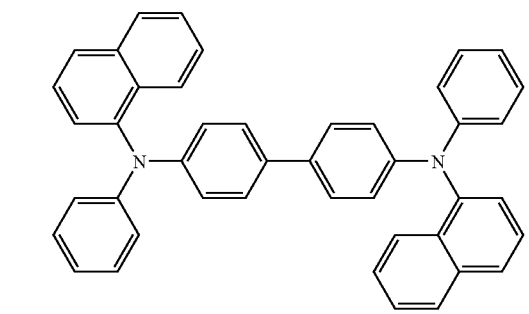

NPB

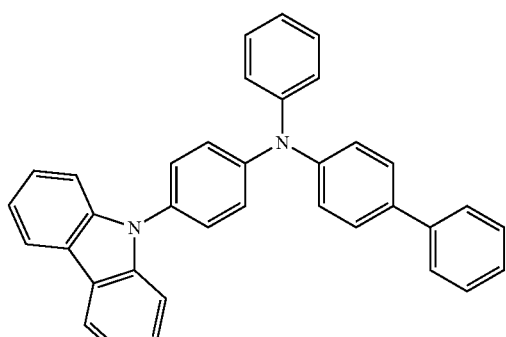

YGA1BP

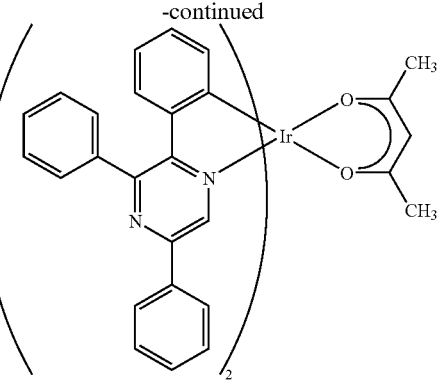

Ir(tppy)₂acac

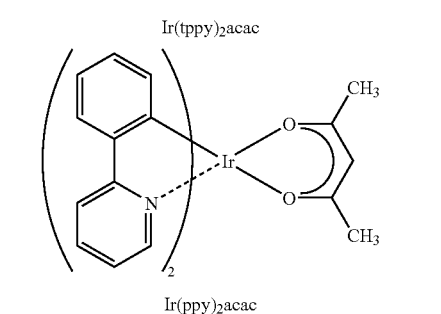

Ir(ppy)₂acac

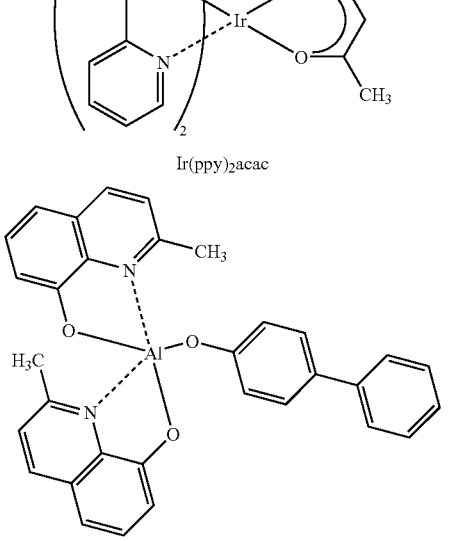

BAlq

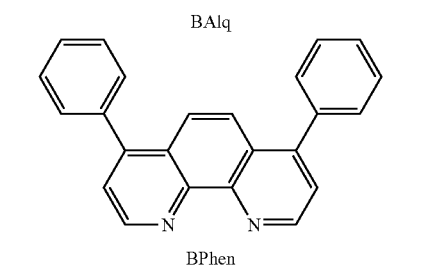

BPhen

A method for fabricating a light-emitting element of this example is described below.

[Light-Emitting Element 1]

First, indium tin oxide containing silicon oxide (ITSO) was deposited over a glass substrate 2100 by a sputtering method to form a first electrode 2101. The thickness and area of the first electrode 2101 were 110 nm and 2 mm×2 mm, respectively.

Next, the substrate provided with the first electrode 2101 was fixed to a substrate holder provided in a vacuum evaporation apparatus so that a surface on which the first electrode 2101 was formed faced downward. After the pressure of the vacuum evaporation apparatus was reduced to approximately $10^{-4}$ Pa, 4,4'-bis[N-(1-naphthyl)-N-phenylamino]biphenyl (abbreviation: NPB) was co-evaporated with molybdenum (VI) oxide to result in a first layer 2111 as a hole-injecting layer which contains a composite material of an organic compound and an inorganic compound. The thickness of the first layer 2111 was 50 nm, and the weight ratio of NPB to molybdenum(VI) oxide was adjusted to be 4:1 NPB molybdenum oxide). Note that the co-evaporation method refers to an evaporation method in which evaporation is carried out from a plurality of evaporation sources at the same time in one treatment chamber.

Next, a 10-nm-thick film of 4,4'-bis[N-(1-naphthyl)-N-phenylamino]biphenyl (abbreviation: NPB) was formed on the first layer 2111 including the composite material by an evaporation method using resistance heating, whereby a second layer 2112 was formed as a hole-transporting layer.

Then, co-evaporation of 4-(9-phenyl-9H-carbazol-3-yl)-4'-(3-phenylqunoxalin-2-yl)triphenylamine (abbreviation: PCBA1PQ) represented by the structural formula (1) with (acetylacetonato)bis(2,3,5-triphenylpyrazinato)iridium(III) (abbreviation: Ir(tppr)$_2$acac) was carried out to form a third layer 2113 as a light-emitting layer over the second layer 2112. Here, the weight ratio between PCBA1PQ and Ir(tppr)$_2$acac was adjusted to be 1:0.01 (=PCBA1PQ:Ir(tppr)$_2$acac). The thickness of the third layer 2113 was 40 nm.

After that, a fourth layer 2114 was formed, over the third layer 2113, as an electron-transporting layer by forming a layer of bis(2-methyl-8-quinolinolato)(4-phenylphenolato)aluminum (abbreviation: BAlq) in a thickness of 10 nm and then a layer of bathophenanthroline (Abbreviation: BPhen) in a thickness of 20 nm by evaporation. Further, lithium fluoride (LiF) was evaporated over the fourth layer 2114 to form a fifth layer 2115 with a thickness of 1 nm as an electron-injecting layer. Finally, aluminum was evaporated to form a second electrode 2102 with a thickness of 200 nm, which functions as a cathode, by which the light-emitting element 1 of the present example was completed.

Note that, in the above evaporation process, evaporation was all performed by a resistance heating method.

[Light-Emitting Element 2]

As to the light-emitting element 2, 4-(5-phenyl-1,3,4-oxadiazol-2-yl)-4'-(9-phenyl-9H-carbazol-3-yl)triphenylamine (abbreviation: PCBAO11) represented by the structural formula (67) was employed as a host material instead of PCBA1PQ which was used as the host material of the third layer 2113 of the light-emitting element 1. Specifically, the third layer 2113 was formed over the second layer 2112 as the light-emitting layer by co-evaporating PCBAO11 with Ir(tppr)$_2$acac. Here, the weight ratio of PCBAO11 to Ir(tppr)$_2$acac was adjusted to be 1:0.08 (=PCBAO11:Ir(tppr)$_2$acac). The thickness of the third layer 2113 was 40 nm. The layers other than the third layer 2113 were formed in a similar manner as those of the light-emitting element 1.

[Light-Emitting Element 3]

As to the light-emitting element 3, 9-phenyl-9'-[4-(3-phenylqunoxalin-2-yl)phenyl]-3,3'-bi(9H-carbazol) (abbreviation: PCC1PQ) represented by the structural formula (35) was employed as a host material instead of PCBA1PQ which was used as the host material of the third layer 2113 of the light-emitting element 1. Specifically, the third layer 2113 was formed over the second layer 2112 as the light-emitting layer by co-evaporating PCC1PQ with Ir(tppr)$_2$acac. Here, the weight ratio of PCC1PQ to Ir(tppr)$_2$acac was adjusted to be 1:0.08 (=PCC1PQ:Ir(tppr)$_2$acac). The thickness of the third layer 2113 was 40 nm. The layers other than the third layer 2113 were fanned in a similar manner as those of the light-emitting element 1.

[Light-Emitting Element 4]

As to the light-emitting element 4, 9-phenyl-9'-[4-(5-phenyl-1,3,4-oxadiazole-2-yl)phenyl]-3,3'-bi(9H-carbazole) (abbreviation: PCCO11) represented by the structural formula (99) was employed as a host material instead of PCBA1PQ which was used as the host material of the third layer 2113 of the light-emitting element 1. Specifically, the third layer 2113 was formed over the second layer 2112 as the light-emitting layer by co-evaporating PCCO11 with Ir(tppr)$_2$acac. Here, the weight ratio of PCCO11 to Ir(tppr)$_2$acac was adjusted to be 1:0.08 (=PCCO11:Ir(tppr)$_2$acac). The thickness of the third layer 2113 was 40 nm. The layers other than the third layer 2113 were faulted in a similar manner as those of the light-emitting element 1.

The light-emitting elements 1 to 4 thus obtained were sealed in a glove box under a nitrogen atmosphere without being exposed to atmospheric air. Then, the operating characteristics of the light-emitting elements were measured. The measurement was carried out at room temperature (in an atmosphere kept at 25° C.).

Figure 23A:
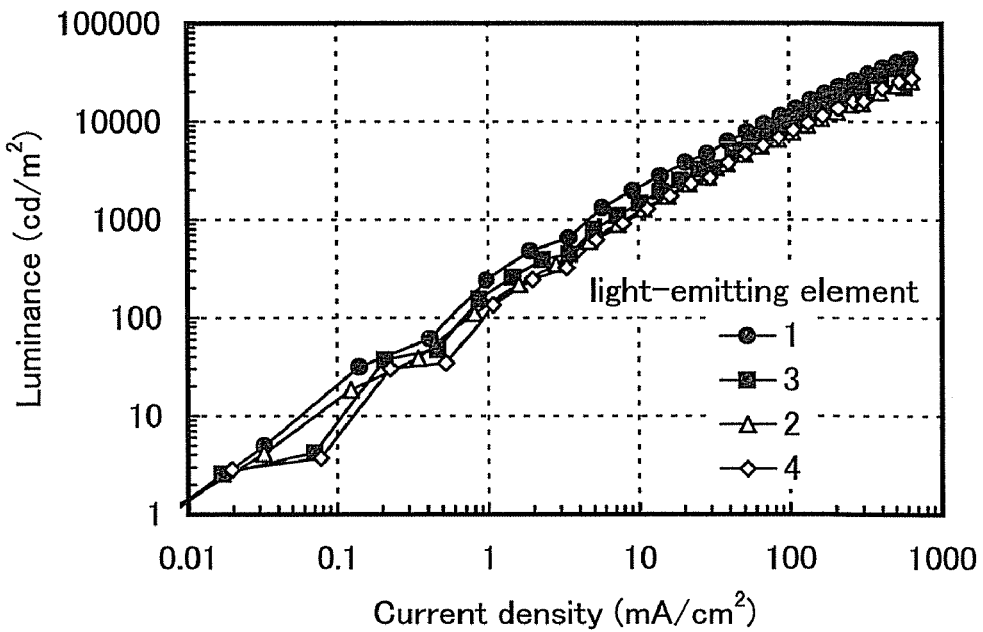
FIGS. 23A and 23B show current density vs. luminance characteristics and voltage vs. luminance characteristics of the light-emitting elements fabricated in Embodiment 5, respectively.
Figure 23B:
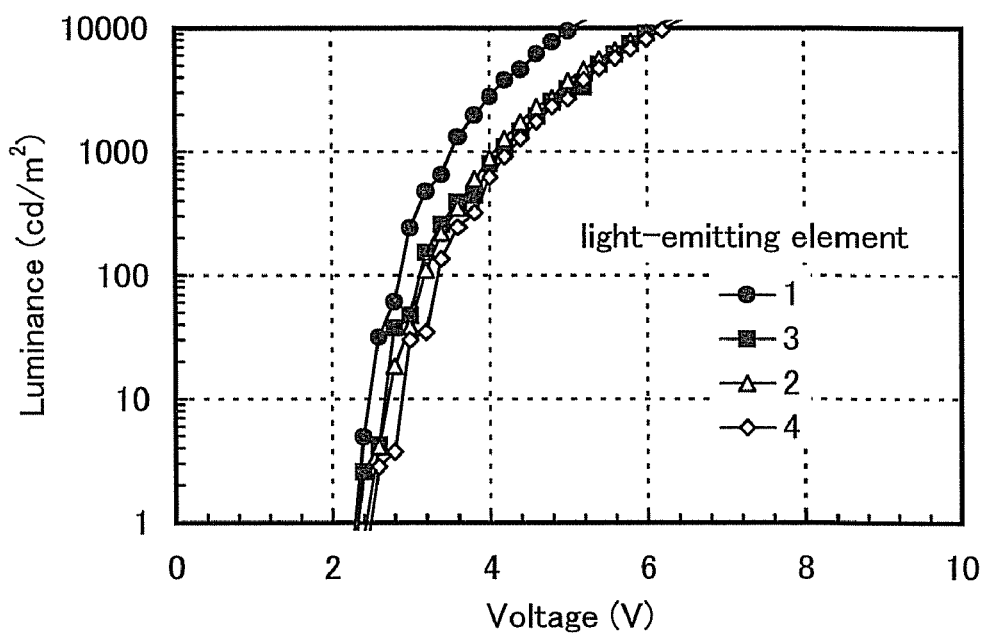
Figure 24A:
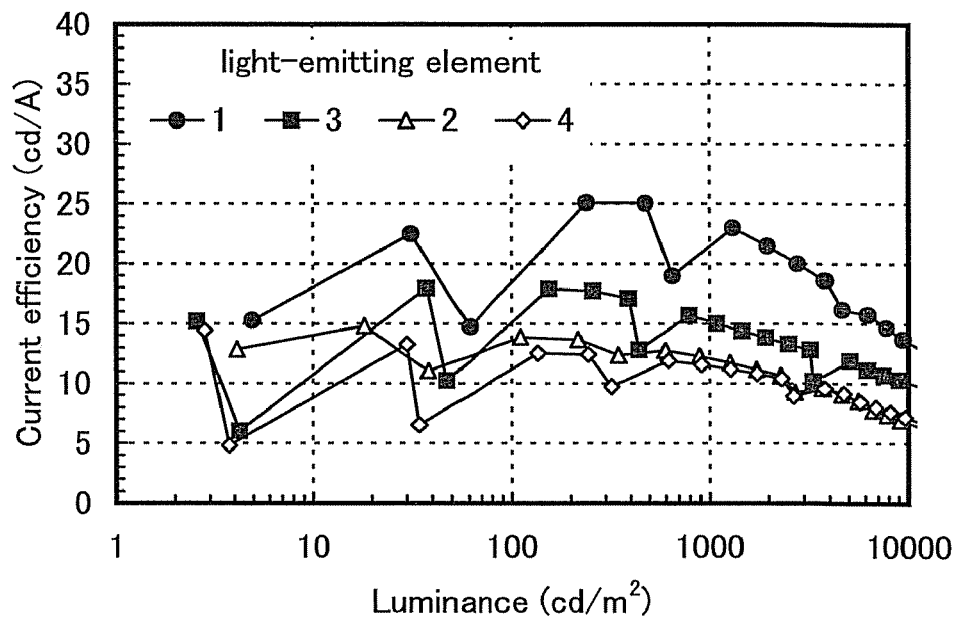
FIGS. 24A and 24B show luminance vs. current efficiency characteristics and emission spectra of the light-emitting elements fabricated in Embodiment 5, respectively.

The current density-luminance characteristics of the light-emitting elements 1 to 4 are shown in FIG. 23A. In FIG. 23A, the horizontal axis represents current density (mA/cm$^2$) and the vertical axis represents luminance (cd/m$^2$). The voltage-luminance characteristics are shown in FIG. 23B. In FIG. 23B, the horizontal axis represents voltage (V) applied to the light-emitting elements, and the vertical axis represents emission luminance (cd/m$^2$). The luminance vs. current efficiency characteristics are shown in FIG. 24A. In FIG. 24A, the horizontal axis represents luminance (cd/m$^2$) and the vertical axis represents current efficiency (cd/A).

The light-emitting element 1 shows CIE color coordinates of x and y of 0.65 and 0.35, respectively, a current efficiency of 23.0 cd/A, and an external quantum efficiency of 16.8% at a voltage of 3.6 V. The light-emitting element 2 shows CIE color coordinates of x and y of 0.65 and 0.35, respectively, a current efficiency of 12.3 cd/A, and an external quantum efficiency of 8.5% at a voltage of 4.0 V. The light-emitting element 3 shows CIE color coordinates of x and y of 0.66 and 0.34, respectively, a current efficiency of 15.0 cd/A, and an external quantum efficiency of 11.8% at a voltage of 4.2 V. The light-emitting element 4 shows CIE color coordinates of x and y of 0.65 and 0.35, respectively, a current efficiency of 11.6 cd/A, and an external quantum efficiency of 8.3% at a voltage of 4.2 V.

Figure 24B:
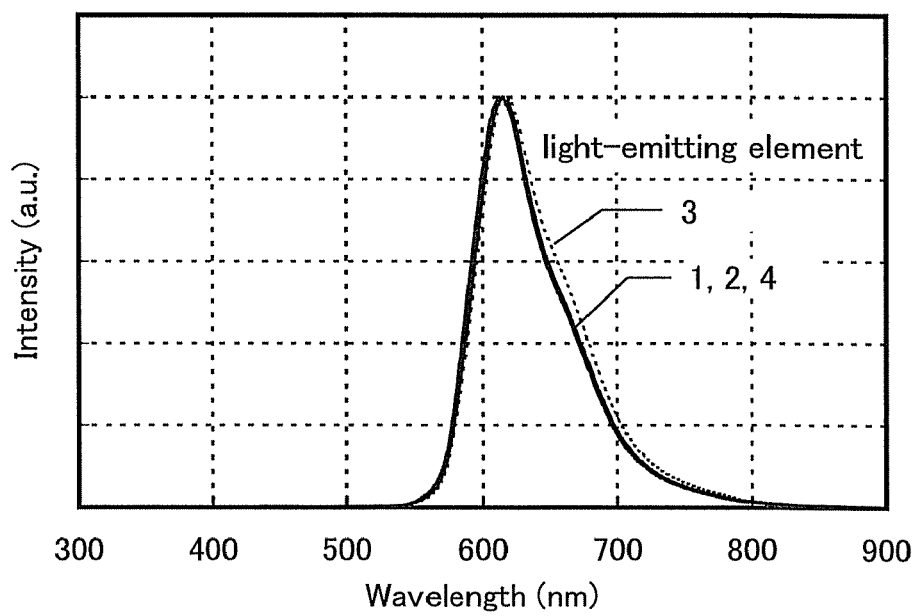

Emission spectra of the light-emitting elements 1 to 4 at a current of 0.5 mA are shown in FIG. 24B. In FIG. 24B, a horizontal axis represents a wavelength (nm) and a longitudinal axis represents the intensity (arbitrary unit). As demonstrated in FIG. 24B, red light emission originating from Ir(tppr)$_2$acac was observed from each of the fabricated light-emitting elements 1 to 4.

As shown in the aforementioned results, the use of the carbazole derivative having the heteroaromatic ring of an embodiment of the present invention as a host material allows the formation of a light-emitting element which can be operated at a low voltage and emit deeply red light in high efficiency.

Example 6

In this example, a light-emitting element having different structure from that shown in Example 5 will be explained.

A method for fabricating the light-emitting element of this example is described below.

[Light-Emitting Element 5]

First, indium tin oxide containing silicon oxide (ITSO) was deposited over the glass substrate 2100 by the sputtering method to faun the first electrode 2101. The thickness and area of the first electrode 2101 were 110 nm and 2 mm×2 mm, respectively.

Next, the substrate provided with the first electrode 2101 was fixed to the substrate holder provided in the vacuum evaporation apparatus so that the surface on which the first electrode 2101 was formed faced downward. After the pressure of the vacuum evaporation apparatus was reduced to approximately $10^{-4}$ Pa, 4,4'-bis[N-(1-naphthyl)-N-phenylamino]biphenyl (abbreviation: NPB) was co-evaporated with molybdenum(VI) oxide to result in the first layer 2111 as the hole-injecting layer which contains the composite material of the organic compound and the inorganic compound. The thickness of the first layer 2111 was 40 nm, and the weight ratio of NPB to molybdenum(VI) oxide was adjusted to be 4:1 (=NPB:molybdenum oxide). Note that the co-evaporation method refers to an evaporation method in which evaporation is carried out from a plurality of evaporation sources at the same time in one treatment chamber.

Next, a 20-nm-thick film of 4-(9H-carbazol-9-yl)phenyl-4'-phenyltriphenylamine (abbreviation: YGA1BP) was formed on the first layer 2111 including the composite material by the evaporation method using resistance heating, whereby the second layer 2112 was formed as the hole-transporting layer.

Then, co-evaporation of 9-phenyl-9'-[4-(5-phenyl-1,3,4-oxadiazole-2-yl)phenyl]-3,3'-bi(9H-carbazole) (abbreviation: PCCO11) represented by the structural formula (99) with bis[2-phenylpyridinato-N,C$^{2'}$]iridium(III) acetylacetonate (abbreviation: Ir(ppy)$_2$acac) was carried out to form the third layer 2113 as the light-emitting layer over the second layer 2112. Here, the weight ratio between PCCO11 and Ir(ppy)$_2$acac was adjusted to be 1:0.01 (=PCCO11:Ir(ppy)$_2$acac). The thickness of the third layer 2113 was 40

After that, a fourth layer 2114 was formed, over the third layer 2113, as an electron-transporting layer by forming a layer of bis(2-methyl-8-quinolinolato)(4-phenylphenolato)aluminum (abbreviation: BAlq) in a thickness of 10 nm and then a layer of bathophenanthroline (Abbreviation: BPhen) in a thickness of 20 nm by evaporation. Further, lithium fluoride (LiF) was evaporated over the fourth layer 2114 to form the fifth layer 2115 with a thickness of 1 nm as the electron-injecting layer. Finally, aluminum was evaporated to form the second electrode 2102 with a thickness of 200 nm, which functions as the cathode, by which the light-emitting element 5 of the present example was completed.

Note that, in the above evaporation process, evaporation was all performed by a resistance heating method.

The light-emitting element 5 thus obtained was sealed in a glove box under a nitrogen atmosphere without being exposed to atmospheric air. Then, the operating characteristics of the light-emitting element were measured. The measurement was carried out at room temperature (in an atmosphere kept at 25° C.).

Figure 25A:
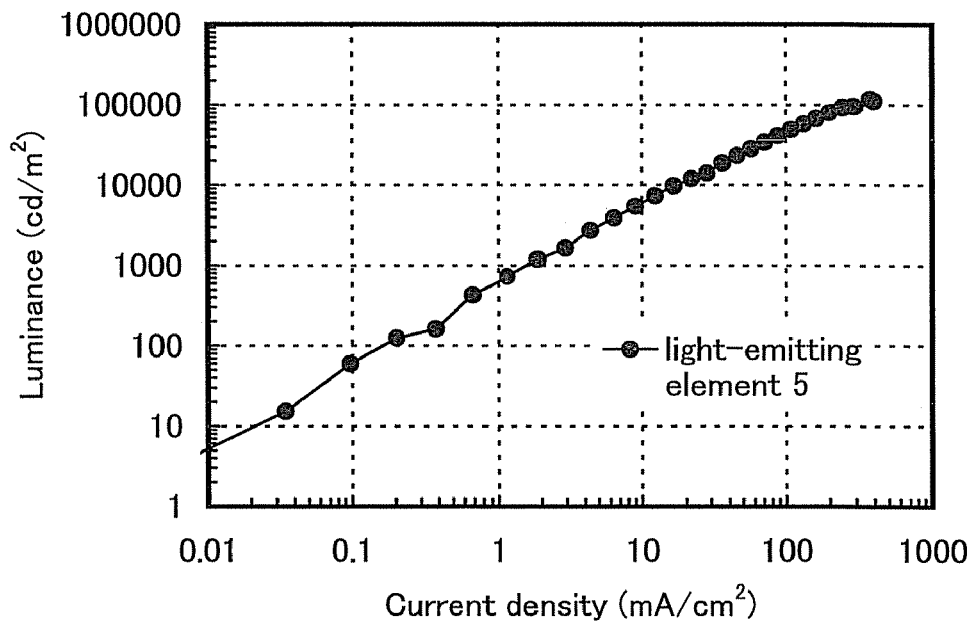
FIGS. 25A and 25B show current density vs. luminance characteristic and voltage vs. luminance characteristic of the light-emitting element fabricated in Embodiment 6, respectively.
Figure 25B:
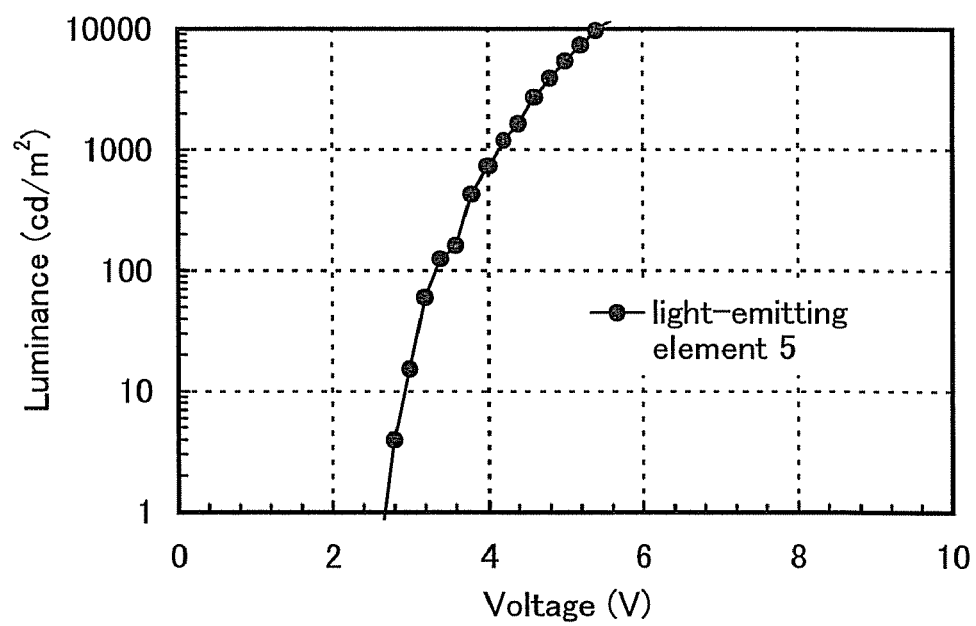
Figure 26A:
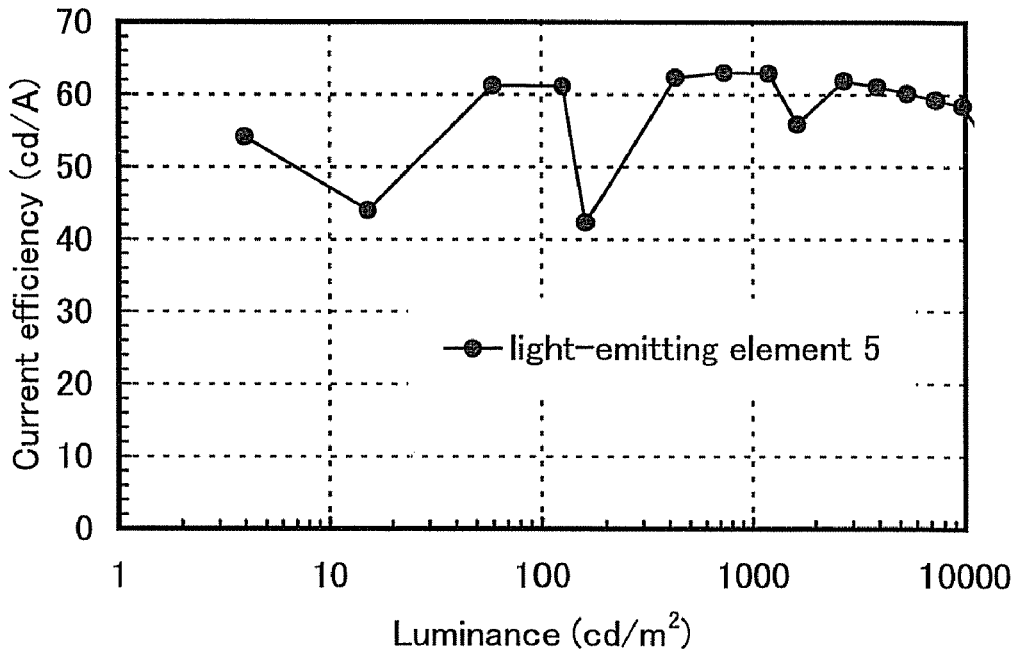
FIGS. 26A and 26B show luminance vs. current efficiency characteristics and emission spectrum of the light-emitting element fabricated in Embodiment 6, respectively.

The current density-luminance characteristics of the light-emitting element 5 are shown in FIG. 25A. In FIG. 25A, the horizontal axis represents current density (mA/cm$^2$) and the vertical axis represents luminance (cd/m$^2$). The voltage-luminance characteristics are shown in FIG. 25B. In FIG. 25B, the horizontal axis represents voltage (V) applied to the light-emitting elements, and the vertical axis represents emission luminance (cd/m$^2$). The luminance vs. current efficiency characteristics are shown in FIG. 26A. In FIG. 26A, the horizontal axis represents luminance (cd/m$^2$) and the vertical axis represents current efficiency (cd/A).

The light-emitting element 5 shows CIE color coordinates of x and y of 0.35 and 0.62, respectively, a current efficiency of 62.9 cd/A, and an external quantum efficiency of 17.6% at a voltage of 4.2 V.

Figure 26B:
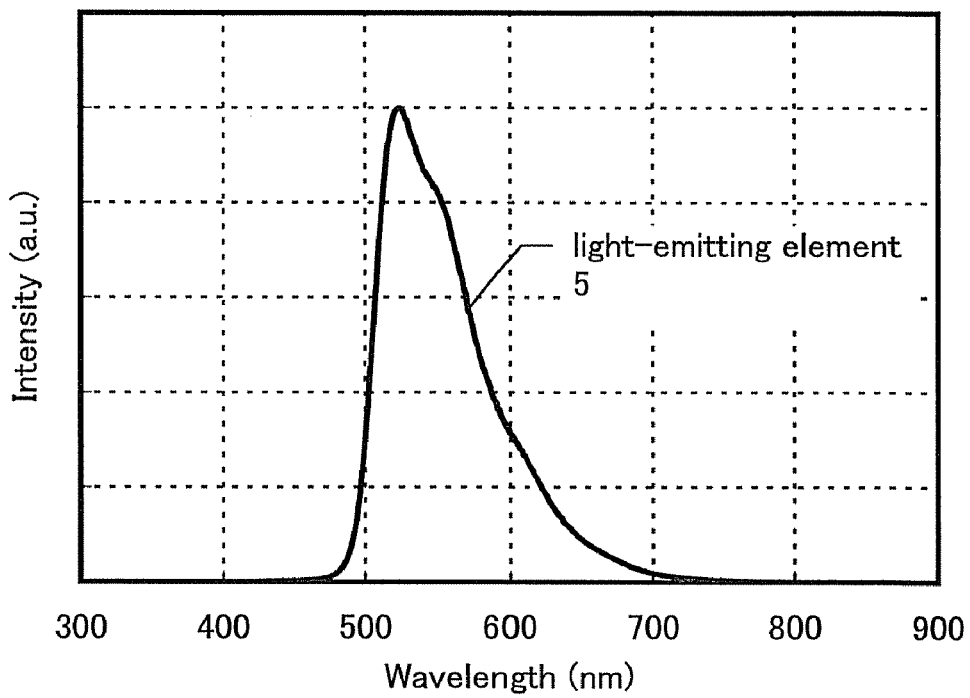

Emission spectrum of the light-emitting element 5 at a current of 0.1 mA is shown in FIG. 26B. In FIG. 26B, the horizontal axis represents a wavelength (nm) and a longitudinal axis represents the intensity (arbitrary unit). As demonstrated in FIG. 26B, green light emission originating from Ir(ppy)$_2$acac was observed from the fabricated light-emitting element 5.

As shown in the aforementioned results, the use of the carbazole derivative having the heteroaromatic ring of an embodiment of the present invention as a host material allows the formation of a light-emitting element which can be operated at a low voltage and emit light with bright green color in high efficiency.

This application is based on Japanese Patent Application serial no. 2009-069177 filed with Japan Patent Office on Mar. 30, 2009, the entire contents of which are hereby incorporated by reference.

What is claimed is:

1. A carbazole derivative represented by a formula (G1),

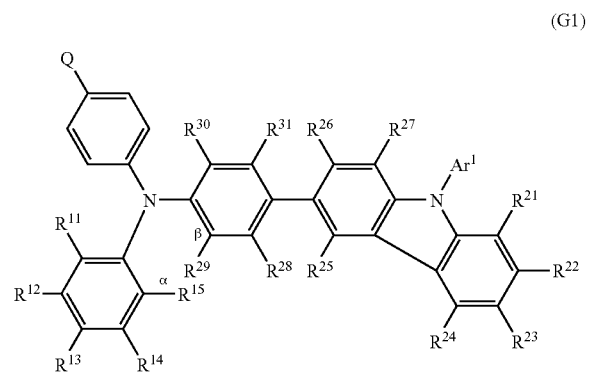

(G1)

wherein:

Q is a substituent represented by a formula (Q2)

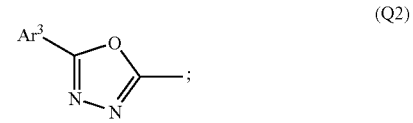

(Q2)

Ar$^1$ and Ar$^3$ each are an aryl group having 6 to 10 carbon atoms in a ring;

R$^{11}$ to R$^{15}$ and R$^{21}$ to R$^{27}$ each are a hydrogen atom, an alkyl group having 1 to 4 carbon atoms, or an aryl group having 6 to 10 carbon atoms in a ring; and R$^{28}$ to R$^{31}$ each are a hydrogen atom or an alkyl group having 1 to 4 carbon atoms.

2. The carbazole derivative according to claim 1, wherein the carbon at the α position and the carbon at the β position are bonded to each other to form a carbazole ring.

3. The carbazole derivative according to claim 1, wherein:

the carbazole derivative is represented by a formula (G2)

(G2)

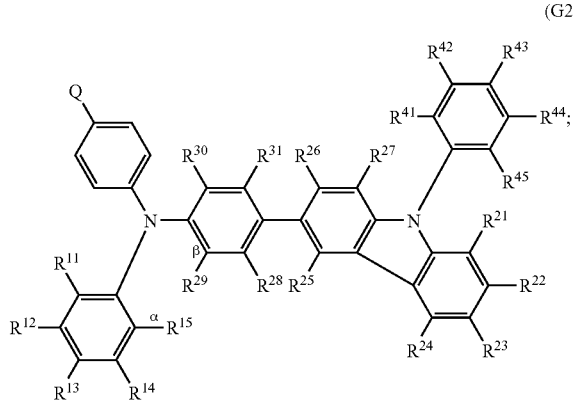

and $R^{41}$ to $R^{45}$ each are a hydrogen atom, an alkyl group having 1 to 4 carbon atoms, or an aryl group having 6 to 10 carbon atoms in a ring.

4. The carbazole derivative according to claim 3, wherein $R^{11}$, $R^{12}$, $R^{14}$, $R^{15}$, and $R^{28}$ to $R^{31}$ each are a hydrogen atom.

5. The carbazole derivative according to claim 3, wherein $R^{11}$, $R^{12}$, $R^{14}$, $R^{15}$, $R^{21}$ to $R^{31}$, and $R^{41}$ to $R^{45}$ each are a hydrogen atom.

6. The carbazole derivative according to claim 3, wherein:

$R^{11}$, $R^{12}$, $R^{14}$, $R^{15}$, $R^{21}$ to $R^{31}$, and $R^{41}$ to $R^{45}$ each are a hydrogen atom;

Q is a substituent represented by a formula (Q2-1)

(Q2-1)

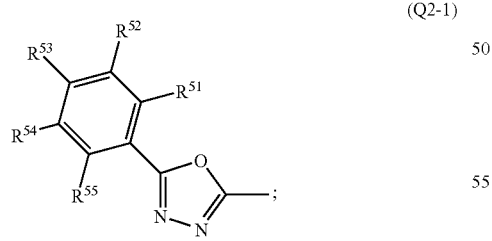

and $R^{51}$ to $R^{55}$ each are a hydrogen atom, an alkyl group having 1 to 4 carbon atoms, or an aryl group having 6 to 10 carbon atoms in a ring.

7. The carbazole derivative according to claim 6, wherein $R^{51}$ to $R^{55}$ each are a hydrogen atom.

8. A light-emitting device having a light-emitting element, the light-emitting element comprising a carbazole derivative between a pair of electrodes, wherein:

the carbazole derivative is represented by a formula (G1)

(G1)

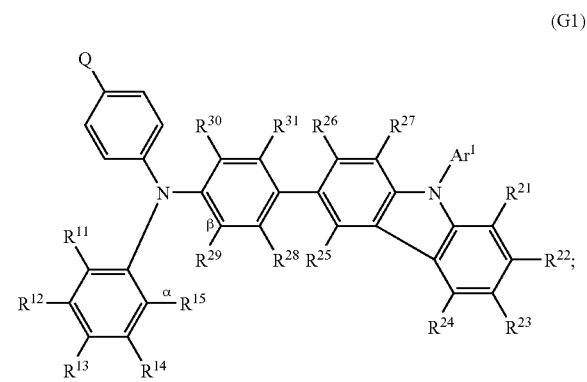

Q is a substituent represented by a formula (Q2)

(Q2)

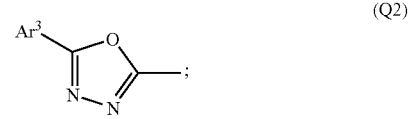

$Ar^1$ and $Ar^3$ each are an aryl group having 6 to 10 carbon atoms in a ring;

$R^{11}$ to $R^{15}$ and $R^{21}$ to $R^{27}$ each are a hydrogen atom, an alkyl group having 1 to 4 carbon atoms, or an aryl group having 6 to 10 carbon atoms in a ring; and $R^{28}$ to $R^{31}$ each are a hydrogen atom or an alkyl group having 1 to 4 carbon atoms.

9. The light-emitting device according to claim 8, wherein:

the light-emitting element comprises a light-emitting layer between the pair of electrodes; and the carbazole derivative is included in the light-emitting layer.

10. The light-emitting device according to claim 8, wherein:

the light-emitting element comprises a light-emitting layer between the pair of electrodes; and a light-emitting substance and the carbazole derivative are included in the light-emitting layer.

11. The light-emitting device according to claim 8, wherein:

the light-emitting element comprises a light-emitting layer between the pair of electrodes; and a phosphorescent substance and the carbazole derivative are included in the light-emitting layer.

12. An electric device having a pixel portion, the pixel portion comprising a light-emitting element,
wherein:
the light-emitting element comprises a carbazole derivative between a pair of electrodes;
the carbazole derivative is represented by a formula (G1)

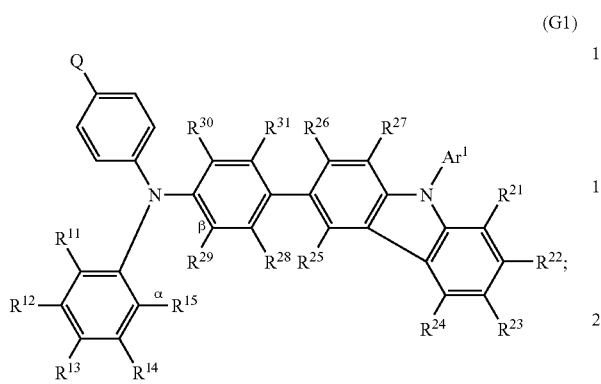

(G1)

Q is a substituent represented by a formula (Q2)

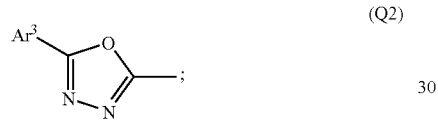

(Q2)

$Ar^1$ and $Ar^3$ each are an aryl group having 6 to 10 carbon atoms in a ring;
$R^{11}$ to $R^{15}$ and $R^{21}$ to $R^{27}$ each are a hydrogen atom, an alkyl group having 1 to 4 carbon atoms, or an aryl group having 6 to 10 carbon atoms in a ring; and
$R^{28}$ to $R^{31}$ each are a hydrogen atom or an alkyl group having 1 to 4 carbon atoms.

13. The electric device according to claim 12, wherein:
the light-emitting element comprises a light-emitting layer between the pair of electrodes; and
the carbazole derivative is included in the light-emitting layer.

14. The electric device according to claim 12, wherein:
the light-emitting element comprises a light-emitting layer between the pair of electrodes; and
a light-emitting substance and the carbazole derivative are included in the light-emitting layer.

15. The electric device according to claim 12, wherein:
the light-emitting element comprises a light-emitting layer between the pair of electrodes; and
a phosphorescent substance and the carbazole derivative are included in the light-emitting layer.

16. A lighting device comprising a light-emitting element, wherein:
the light-emitting element comprises a carbazole derivative between a pair of electrodes;
the carbazole derivative is represented by a formula (G1)

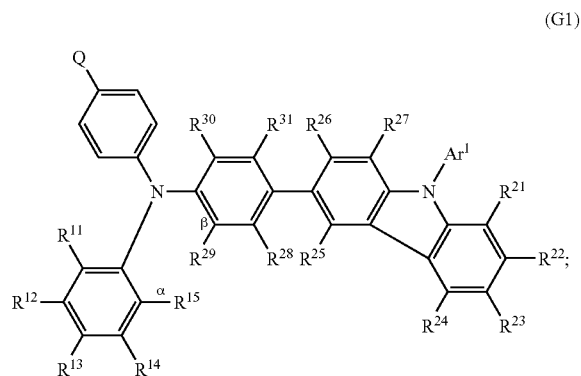

(G1)

Q is a substituent represented by the formula (Q2)

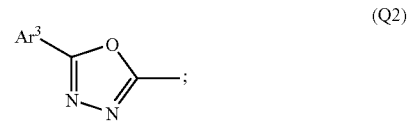

(Q2)

$Ar^1$ and $Ar^3$ each are an aryl group having 6 to 10 carbon atoms in a ring;
$R^{11}$ to $R^{15}$ and $R^{21}$ to $R^{27}$ each are a hydrogen atom, an alkyl group having 1 to 4 carbon atoms, or an aryl group having 6 to 10 carbon atoms in a ring; and
$R^{28}$ to $R^{31}$ each are a hydrogen atom or an alkyl group having 1 to 4 carbon atoms.

17. The lighting device according to claim 16, wherein:
the light-emitting element comprises a light-emitting layer between the pair of electrodes; and
the carbazole derivative is included in the light-emitting layer.

18. The lighting device according to claim 16, wherein:
the light-emitting element comprises a light-emitting layer between the pair of electrodes; and
a light-emitting substance and the carbazole derivative are included in the light-emitting layer.

19. The lighting device according to claim 16, wherein:
the light-emitting element comprises a light-emitting layer between the pair of electrodes; and
a phosphorescent substance and the carbazole derivative are included in the light-emitting layer.

* * * * *